(12) United States Patent
Chanduszko et al.

(10) Patent No.: US 9,204,956 B2
(45) Date of Patent: *Dec. 8, 2015

(54) IVC FILTER WITH TRANSLATING HOOKS

(75) Inventors: Andrzej J. Chanduszko, Chandler, AZ (US); Scott L. Randall, Mesa, AZ (US); William R. Bratt, Tempe, AZ (US)

(73) Assignee: C. R. Bard, Inc., Murray Hill, NJ (US)

(*) Notice: Subject to any disclaimer, the term of this patent is extended or adjusted under 35 U.S.C. 154(b) by 342 days.

This patent is subject to a terminal disclaimer.

(21) Appl. No.: 13/584,586

(22) Filed: Aug. 13, 2012

(65) Prior Publication Data

US 2013/0006295 A1 Jan. 3, 2013

Related U.S. Application Data

(63) Continuation-in-part of application No. 12/299,300, filed as application No. PCT/US2007/009215 on Apr. 16, 2007, now Pat. No. 8,333,785, and a continuation-in-part of application No. 13/009,727, (Continued)

(51) Int. Cl.
*A61F 2/01* (2006.01)

(52) U.S. Cl.
CPC ............ *A61F 2/01* (2013.01); *A61F 2002/016* (2013.01); *A61F 2002/018* (2013.01); *A61F 2230/005* (2013.01); *A61F 2230/008* (2013.01)

(58) Field of Classification Search
CPC ............... A61F 2/01; A61F 2002/018; A61F 2230/0067; A61F 2230/005; A61F 2230/008; A61F 2002/016; A61M 29/00
USPC ................. 606/108, 151–157, 191–200, 213; 604/104–109
See application file for complete search history.

(56) References Cited

U.S. PATENT DOCUMENTS

| | | | |
|---|---|---|---|
| 893,055 | A | 7/1908 | Conner |
| 2,212,334 | A | 8/1940 | Wallerich |
| 2,767,703 | A | 10/1956 | Nieburgs |

(Continued)

FOREIGN PATENT DOCUMENTS

| | | |
|---|---|---|
| CA | 2173118 A1 | 4/1995 |
| CA | 2648325 A1 | 4/2000 |

(Continued)

OTHER PUBLICATIONS

WO96_17634, Nott et al., date: 1996.*

(Continued)

*Primary Examiner* — Manuel Mendez
(74) *Attorney, Agent, or Firm* — Buchalter Nemer

(57) ABSTRACT

A filter with translating hooks is described. The filter can include strut members having first and second struts connected by a connecting portion. A translating hook is disposed adjacent the connecting portion of the strut members, the hook including a first elongate member attached at one end to the first strut and a second elongate member attached at one end to a second strut, the opposite ends of the elongate members connected together to define a tip. The translating hooks are configured to bend toward a central axis of the filter when the filter is in a collapsed configuration for delivery to a blood vessel and recovery from a blood vessel, and away from the central axis of the filter when the filter is in an expanded configuration within a blood vessel such that the hooks engage a vessel wall.

20 Claims, 3 Drawing Sheets

Related U.S. Application Data filed on Jan. 19, 2011, now Pat. No. 8,241,350, which is a continuation of application No. 11/966,203, filed on Dec. 28, 2007, now Pat. No. 7,887,580, which is a continuation of application No. 10/079,155, filed on Feb. 20, 2002, now Pat. No. 7,331,992.

(60) Provisional application No. 60/797,006, filed on May 2, 2006.

(56) References Cited

U.S. PATENT DOCUMENTS

| | | |
|---|---|---|
| 3,334,629 A | 8/1967 | Cohn |
| 3,472,230 A | 10/1969 | Fogarty |
| 3,540,431 A | 11/1970 | Mobin-Uddia |
| 3,579,798 A | 5/1971 | Henderson |
| 3,620,212 A | 11/1971 | Fannon, Jr. et al. |
| 3,657,744 A | 4/1972 | Ersek |
| 3,875,928 A | 4/1975 | Angelchik |
| 3,885,562 A | 5/1975 | Lampkin |
| 3,952,747 A | 4/1976 | Kimmell, Jr. |
| 4,000,739 A | 1/1977 | Stevens |
| 4,041,931 A | 8/1977 | Elliott et al. |
| 4,198,960 A | 4/1980 | Utsugi et al. |
| 4,256,132 A | 3/1981 | Gunter |
| 4,282,876 A | 8/1981 | Flynn |
| 4,283,447 A | 8/1981 | Flynn |
| 4,317,446 A | 3/1982 | Ambrosio et al. |
| 4,334,536 A | 6/1982 | Pfleger |
| 4,343,048 A | 8/1982 | Ross et al. |
| 4,411,655 A | 10/1983 | Schreck |
| 4,419,095 A | 12/1983 | Nebergall et al. |
| 4,425,908 A | 1/1984 | Simon |
| 4,494,531 A | 1/1985 | Gianturco |
| 4,562,596 A | 1/1986 | Kornberg |
| 4,572,186 A | 2/1986 | Gould et al. |
| 4,586,501 A | 5/1986 | Claracq et al. |
| 4,588,399 A | 5/1986 | Nebergall et al. |
| 4,590,938 A | 5/1986 | Segura et al. |
| 4,611,594 A | 9/1986 | Grayhack et al. |
| 4,619,246 A | 10/1986 | Molgaard-Nielsen et al. |
| 4,643,184 A | 2/1987 | Mobin-Uddin |
| 4,655,219 A | 4/1987 | Petruzzi |
| 4,655,771 A | 4/1987 | Wallsten |
| 4,657,024 A | 4/1987 | Coneys |
| 4,665,906 A | 5/1987 | Jervis |
| 4,680,573 A | 7/1987 | Ciordinik et al. |
| 4,688,553 A | 8/1987 | Metals et al. |
| 4,710,192 A | 12/1987 | Liotta et al. |
| 4,722,344 A | 2/1988 | Cambron et al. |
| 4,727,873 A | 3/1988 | Mobin-Uddin |
| 4,735,616 A | 4/1988 | Eibl et al. |
| 4,781,177 A | 11/1988 | Lebigot et al. |
| 4,793,348 A | 12/1988 | Palmaz |
| 4,798,591 A | 1/1989 | Okada et al. |
| 4,817,600 A | 4/1989 | Herms et al. |
| 4,832,055 A | 5/1989 | Palestrant |
| 4,838,879 A | 6/1989 | Tanabe et al. |
| 4,857,062 A | 8/1989 | Russell |
| 4,863,442 A | 9/1989 | DeMello et al. |
| 4,873,978 A | 10/1989 | Ginsburg |
| 4,886,506 A | 12/1989 | Lovgren et al. |
| 4,888,506 A | 12/1989 | Umehara et al. |
| 4,898,591 A | 2/1990 | Jang et al. |
| 4,915,695 A | 4/1990 | Koobs |
| 4,922,905 A | 5/1990 | Strecker et al. |
| 4,943,297 A | 7/1990 | Saveliev et al. |
| 4,950,227 A | 8/1990 | Savin et al. |
| 4,957,501 A | 9/1990 | Lahille et al. |
| 4,969,891 A | 11/1990 | Gewertz |
| 4,990,151 A | 2/1991 | Wallsten |
| 4,990,156 A | 2/1991 | Lefebvre |
| 5,045,072 A | 9/1991 | Castillo et al. |
| 5,059,205 A | 10/1991 | El-Nounou et al. |
| 5,067,957 A | 11/1991 | Jervis |
| 5,074,867 A | 12/1991 | Wilk |
| 5,098,440 A | 3/1992 | Hillstead |
| 5,108,418 A | 4/1992 | Lefebvre et al. |
| 5,114,408 A | 5/1992 | Fleischhaker et al. |
| 5,120,308 A | 6/1992 | Hess |
| 5,133,733 A | 7/1992 | Rasmussen et al. |
| 5,147,378 A | 9/1992 | Markham |
| 5,147,379 A | 9/1992 | Sabbaghian et al. |
| 5,152,777 A | 10/1992 | Goldberg et al. |
| 5,171,232 A | 12/1992 | Castillo et al. |
| 5,188,616 A | 2/1993 | Nadal et al. |
| 5,190,546 A | 3/1993 | Jervis |
| 5,203,776 A | 4/1993 | Durfee |
| 5,219,358 A | 6/1993 | Bendel et al. |
| 5,234,416 A | 8/1993 | Macaulay et al. |
| 5,234,458 A | 8/1993 | Metais et al. |
| 5,242,462 A | 9/1993 | El-Nounou et al. |
| 5,292,331 A | 3/1994 | Boneau |
| 5,300,086 A | 4/1994 | Gory et al. |
| 5,304,156 A | 4/1994 | Sylvanowicz et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,398 A | 9/1994 | Pavcnik et al. |
| 5,358,493 A | 10/1994 | Schweich, Jr. et al. |
| 5,370,657 A | 12/1994 | Irie |
| 5,375,612 A | 12/1994 | Cottenceau et al. |
| 5,383,887 A | 1/1995 | Nadal et al. |
| 5,397,310 A | 3/1995 | Chu et al. |
| 5,397,355 A | 3/1995 | Marin et al. |
| 5,413,586 A | 5/1995 | Dibie et al. |
| 5,421,832 A | 6/1995 | Lefebvre et al. |
| 5,423,851 A | 6/1995 | Samuels |
| 5,443,497 A | 8/1995 | Venbrux |
| 5,464,408 A | 11/1995 | Duc |
| 5,485,667 A | 1/1996 | Kleshinski |
| 5,514,154 A | 5/1996 | Lau et al. |
| 5,531,788 A | 7/1996 | Dibie et al. |
| 5,545,151 A | 8/1996 | O'Connor et al. |
| 5,545,210 A | 8/1996 | Hess et al. |
| 5,549,576 A | 8/1996 | Patterson et al. |
| 5,549,626 A | 8/1996 | Miller et al. |
| 5,554,181 A | 9/1996 | Das |
| 5,558,652 A | 9/1996 | Henke |
| 5,562,698 A | 10/1996 | Parker |
| 5,562,728 A | 10/1996 | Lazarus et al. |
| 5,591,197 A | 1/1997 | Orth et al. |
| 5,593,417 A | 1/1997 | Rhodes |
| 5,593,434 A | 1/1997 | Williams |
| 5,597,378 A | 1/1997 | Jervis |
| 5,601,568 A | 2/1997 | Chevillon et al. |
| 5,601,595 A | 2/1997 | Smith |
| 5,603,721 A | 2/1997 | Lau et al. |
| 5,624,508 A | 4/1997 | Flomenblit et al. |
| 5,626,605 A | 5/1997 | Irie et al. |
| 5,630,822 A | 5/1997 | Hermann et al. |
| 5,634,942 A | 6/1997 | Chevillon et al. |
| 5,641,364 A | 6/1997 | Golberg et al. |
| 5,649,906 A | 7/1997 | Gory et al. |
| 5,669,879 A | 9/1997 | Duer et al. |
| 5,669,933 A | 9/1997 | Simon et al. |
| 5,672,153 A | 9/1997 | Lax et al. |
| 5,672,158 A | 9/1997 | Okada et al. |
| 5,674,278 A | 10/1997 | Boneau |
| 5,681,347 A | 10/1997 | Cathcart et al. |
| 5,683,411 A | 11/1997 | Kavteladze et al. |
| 5,695,518 A | 12/1997 | Laerum et al. |
| 5,695,519 A | 12/1997 | Summers et al. |
| 5,702,370 A | 12/1997 | Sylvanowicz et al. |
| 5,704,910 A | 1/1998 | Humes |
| 5,704,926 A | 1/1998 | Sutton |
| 5,704,928 A | 1/1998 | Morita et al. |
| 5,707,376 A | 1/1998 | Kavteladze et al. |
| 5,709,704 A | 1/1998 | Nott et al. |
| 5,720,762 A | 2/1998 | Bass |
| 5,720,764 A | 2/1998 | Naderlinger |
| 5,720,776 A | 2/1998 | Chuter et al. |
| 5,725,550 A | 3/1998 | Nadal et al. |
| 5,746,767 A | 5/1998 | Smith |

(56) References Cited

U.S. PATENT DOCUMENTS

| | | |
|---|---|---|
| 5,755,790 A | 5/1998 | Chevillon et al. |
| 5,759,192 A | 6/1998 | Saunders |
| 5,769,816 A | 6/1998 | Barbut et al. |
| 5,775,790 A | 7/1998 | Ohtake |
| 5,776,162 A | 7/1998 | Kleshinski |
| 5,776,181 A | 7/1998 | Lee et al. |
| 5,780,807 A | 7/1998 | Saunders |
| 5,800,457 A | 9/1998 | Gelbfish |
| 5,800,515 A | 9/1998 | Nadal et al. |
| 5,800,526 A | 9/1998 | Anderson et al. |
| 5,830,222 A | 11/1998 | Makower |
| 5,836,968 A | 11/1998 | Simon et al. |
| 5,836,969 A | 11/1998 | Kim et al. |
| 5,843,164 A | 12/1998 | Frantzen et al. |
| 5,843,167 A | 12/1998 | Dwyer et al. |
| 5,853,420 A | 12/1998 | Chevillon et al. |
| 5,879,382 A | 3/1999 | Boneau |
| 5,891,190 A | 4/1999 | Boneau |
| 5,893,867 A | 4/1999 | Bagaoisan et al. |
| 5,893,869 A | 4/1999 | Barnhart et al. |
| 5,896,869 A | 4/1999 | Maniscalco et al. |
| 5,897,497 A | 4/1999 | Fernandez |
| 5,911,704 A | 6/1999 | Humes |
| 5,919,224 A | 7/1999 | Thompson et al. |
| 5,928,261 A | 7/1999 | Ruiz |
| 5,935,162 A | 8/1999 | Dang |
| 5,938,683 A | 8/1999 | Lefebvre |
| 5,944,728 A | 8/1999 | Bates |
| 5,951,585 A | 9/1999 | Cathcart et al. |
| 5,954,741 A | 9/1999 | Fox et al. |
| 5,961,546 A | 10/1999 | Robinson et al. |
| 5,968,052 A | 10/1999 | Sullivan, III et al. |
| 5,968,071 A | 10/1999 | Chevillon et al. |
| 5,972,019 A | 10/1999 | Engelson et al. |
| 5,976,172 A | 11/1999 | Homsma et al. |
| 5,984,947 A | 11/1999 | Smith |
| 5,989,266 A | 11/1999 | Foster |
| 6,001,118 A | 12/1999 | Daniel et al. |
| 6,004,347 A | 12/1999 | McNamara et al. |
| 6,007,558 A | 12/1999 | Ravenscroft et al. |
| 6,013,093 A | 1/2000 | Nott et al. |
| 6,036,723 A | 3/2000 | Anidjar et al. |
| 6,051,015 A | 4/2000 | Maahs |
| 6,059,814 A | 5/2000 | Ladd |
| 6,059,825 A | 5/2000 | Hobbs et al. |
| 6,066,158 A | 5/2000 | Engelson et al. |
| 6,068,638 A | 5/2000 | Makower |
| 6,068,645 A | 5/2000 | Tu |
| 6,071,292 A | 6/2000 | Makower et al. |
| 6,071,307 A | 6/2000 | Rhee et al. |
| 6,077,297 A | 6/2000 | Robinson et al. |
| 6,077,880 A | 6/2000 | Castillo et al. |
| 6,080,178 A | 6/2000 | Meglin |
| 6,099,534 A | 8/2000 | Bates et al. |
| 6,099,549 A | 8/2000 | Bosma et al. |
| 6,102,932 A | 8/2000 | Kurz |
| 6,113,608 A | 9/2000 | Monroe et al. |
| 6,126,645 A | 10/2000 | Thompson |
| 6,126,673 A | 10/2000 | Kim et al. |
| 6,131,266 A | 10/2000 | Saunders |
| 6,132,388 A | 10/2000 | Fleming et al. |
| 6,146,404 A | 11/2000 | Kim et al. |
| 6,156,055 A | 12/2000 | Ravenscroft |
| 6,159,225 A | 12/2000 | Makower |
| 6,162,357 A | 12/2000 | Pakki et al. |
| 6,165,179 A | 12/2000 | Cathcart et al. |
| 6,165,200 A | 12/2000 | Tsugita et al. |
| 6,171,297 B1 | 1/2001 | Pedersen et al. |
| 6,190,353 B1 | 2/2001 | Makower et al. |
| 6,193,739 B1 | 2/2001 | Chevillon et al. |
| 6,193,748 B1 | 2/2001 | Thompson et al. |
| 6,206,888 B1 | 3/2001 | Bicek et al. |
| 6,214,025 B1 | 4/2001 | Thistle et al. |
| 6,217,600 B1 | 4/2001 | DiMatteo |
| 6,228,052 B1 | 5/2001 | Pohndorf |
| 6,231,581 B1 | 5/2001 | Shank et al. |
| 6,231,587 B1 | 5/2001 | Makower |
| 6,231,588 B1 | 5/2001 | Zadno-Azizi |
| 6,231,589 B1 | 5/2001 | Wessman et al. |
| 6,235,045 B1 | 5/2001 | Barbut et al. |
| 6,241,738 B1 | 6/2001 | Dereume |
| 6,241,746 B1 | 6/2001 | Bosma et al. |
| 6,245,012 B1 | 6/2001 | Kleshinski |
| 6,245,099 B1 | 6/2001 | Edwin et al. |
| 6,251,122 B1 | 6/2001 | Tsukernik |
| 6,254,609 B1 | 7/2001 | Vrba et al. |
| 6,254,633 B1 | 7/2001 | Pinchuk et al. |
| 6,258,026 B1 | 7/2001 | Ravenscroft et al. |
| 6,258,101 B1 | 7/2001 | Blake, III |
| 6,264,664 B1 | 7/2001 | Avellanet |
| 6,264,671 B1 | 7/2001 | Stack et al. |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,280,451 B1 | 8/2001 | Bates et al. |
| 6,280,459 B1 | 8/2001 | Doble |
| 6,282,222 B1 | 8/2001 | Wieser et al. |
| 6,283,983 B1 | 9/2001 | Makower et al. |
| 6,287,317 B1 | 9/2001 | Makower et al. |
| 6,287,332 B1 | 9/2001 | Bolz et al. |
| 6,287,335 B1 | 9/2001 | Drasler et al. |
| 6,290,710 B1 | 9/2001 | Cryer et al. |
| 6,302,875 B1 | 10/2001 | Makower et al. |
| 6,302,891 B1 | 10/2001 | Nadal et al. |
| 6,306,163 B1 | 10/2001 | Fitz |
| 6,322,541 B2 | 11/2001 | West et al. |
| 6,325,790 B1 | 12/2001 | Trotta |
| 6,328,755 B1 | 12/2001 | Marshall |
| 6,331,183 B1 | 12/2001 | Suon |
| 6,336,934 B1 | 1/2002 | Gilson et al. |
| 6,342,062 B1 | 1/2002 | Suon et al. |
| 6,342,063 B1 | 1/2002 | DeVries et al. |
| 6,344,053 B1 | 2/2002 | Boneau |
| 6,355,056 B1 | 3/2002 | Pinheiro |
| 6,361,546 B1 | 3/2002 | Khosravi |
| 6,383,193 B1 | 5/2002 | Cathcart et al. |
| 6,383,195 B1 | 5/2002 | Richard |
| 6,383,206 B1 | 5/2002 | Gillick et al. |
| 6,391,045 B1 | 5/2002 | Kim et al. |
| 6,402,771 B1 | 6/2002 | Palmer et al. |
| 6,416,530 B2 | 7/2002 | DeVries et al. |
| 6,425,909 B1 | 7/2002 | Dieck et al. |
| 6,428,559 B1 | 8/2002 | Johnson |
| 6,432,127 B1 | 8/2002 | Kim et al. |
| 6,436,120 B1 | 8/2002 | Meglin |
| 6,436,121 B1 | 8/2002 | Blom |
| 6,440,077 B1 | 8/2002 | Jung et al. |
| 6,442,413 B1 | 8/2002 | Silver |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,458,145 B1 | 10/2002 | Ravenscroft et al. |
| 6,468,290 B1 | 10/2002 | Weldon et al. |
| 6,482,222 B1 | 11/2002 | Bruckheimer et al. |
| 6,485,500 B1 | 11/2002 | Kokish et al. |
| 6,485,501 B1 | 11/2002 | Green |
| 6,485,502 B2 | 11/2002 | Don Michael et al. |
| 6,488,662 B2 | 12/2002 | Sirimanne |
| 6,497,709 B1 | 12/2002 | Heath |
| 6,506,205 B2 | 1/2003 | Goldberg et al. |
| 6,511,492 B1 | 1/2003 | Rosenbluth et al. |
| 6,511,496 B1 | 1/2003 | Huter et al. |
| 6,511,503 B1 | 1/2003 | Burkett et al. |
| 6,517,559 B1 | 2/2003 | O'Connell |
| 6,517,573 B1 | 2/2003 | Pollock et al. |
| 6,527,962 B1 | 3/2003 | Nadal |
| 6,537,294 B1 | 3/2003 | Boyle et al. |
| 6,537,295 B2 | 3/2003 | Petersen |
| 6,537,296 B2 | 3/2003 | Levinson et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,280 B1 | 4/2003 | Daniel et al. |

(56) References Cited

U.S. PATENT DOCUMENTS

| | | |
|---|---|---|
| 6,551,303 B1 | 4/2003 | Van Tassel et al. |
| 6,551,340 B1 | 4/2003 | Konya et al. |
| 6,551,342 B1 | 4/2003 | Shen et al. |
| 6,558,404 B2 | 5/2003 | Tsukernik |
| 6,558,405 B1 | 5/2003 | McInnes |
| 6,558,406 B2 | 5/2003 | Okada et al. |
| 6,563,080 B2 | 5/2003 | Shapovalov et al. |
| 6,569,183 B1 | 5/2003 | Kim et al. |
| 6,569,184 B2 | 5/2003 | Huter |
| 6,572,605 B1 | 6/2003 | Humes |
| 6,575,997 B1 | 6/2003 | Palmer et al. |
| 6,579,314 B1 | 6/2003 | Lombardi et al. |
| 6,582,447 B1 | 6/2003 | Patel et al. |
| 6,589,266 B2 | 7/2003 | Whitcher et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,602,226 B1 | 8/2003 | Smith et al. |
| 6,602,273 B2 | 8/2003 | Marshall |
| 6,607,553 B1 | 8/2003 | Healy et al. |
| 6,610,077 B1 | 8/2003 | Hancock et al. |
| 6,616,680 B1 | 9/2003 | Thielen |
| 6,616,681 B2 | 9/2003 | Hanson et al. |
| 6,620,183 B2 | 9/2003 | DiMatteo |
| 6,623,450 B1 | 9/2003 | Dutta |
| 6,623,506 B2 | 9/2003 | McGuckin, Jr. et al. |
| 6,629,993 B2 | 10/2003 | Voinov et al. |
| 6,638,293 B1 | 10/2003 | Makower et al. |
| 6,640,077 B2 | 10/2003 | Suzuki et al. |
| 6,641,590 B1 | 11/2003 | Palmer et al. |
| 6,645,152 B1 | 11/2003 | Jung et al. |
| 6,645,224 B2 | 11/2003 | Gilson et al. |
| 6,652,555 B1 | 11/2003 | VanTassel et al. |
| 6,652,556 B1 | 11/2003 | VanTassel et al. |
| 6,652,558 B2 | 11/2003 | Patel et al. |
| 6,652,692 B2 | 11/2003 | Pedersen et al. |
| 6,656,203 B2 | 12/2003 | Roth et al. |
| 6,660,021 B1 | 12/2003 | Palmer et al. |
| 6,660,031 B2 | 12/2003 | Tran et al. |
| 6,663,650 B2 | 12/2003 | Sepetka et al. |
| 6,679,902 B1 | 1/2004 | Boyle et al. |
| 6,679,903 B2 | 1/2004 | Kurz |
| 6,682,540 B1 | 1/2004 | Sancoff et al. |
| 6,685,722 B1 | 2/2004 | Rosenbluth et al. |
| 6,685,738 B2 | 2/2004 | Chouinard et al. |
| 6,689,150 B1 | 2/2004 | VanTassel et al. |
| 6,695,813 B1 | 2/2004 | Boyle et al. |
| 6,696,667 B1 | 2/2004 | Flanagan et al. |
| 6,702,834 B1 | 3/2004 | Boylan et al. |
| 6,702,843 B1 | 3/2004 | Brown et al. |
| 6,706,054 B2 | 3/2004 | Wessman et al. |
| 6,712,834 B2 | 3/2004 | Yassour et al. |
| 6,716,208 B2 | 4/2004 | Humes |
| 6,719,717 B1 | 4/2004 | Johnson et al. |
| 6,719,772 B2 | 4/2004 | Trask et al. |
| 6,726,621 B2 | 4/2004 | Suon et al. |
| 6,730,108 B2 | 5/2004 | Van Tassel et al. |
| 6,736,842 B2 | 5/2004 | Healy et al. |
| 6,752,819 B1 | 6/2004 | Brady et al. |
| 6,755,846 B1 | 6/2004 | Yadav |
| 6,761,732 B2 | 7/2004 | Burkett et al. |
| 6,773,448 B2 | 8/2004 | Kusleika et al. |
| 6,776,770 B1 | 8/2004 | Trerotola |
| 6,776,774 B2 | 8/2004 | Tansey, Jr. et al. |
| 6,783,538 B2 | 8/2004 | McGuckin, Jr. et al. |
| 6,792,979 B2 | 9/2004 | Konya et al. |
| 6,793,665 B2 | 9/2004 | McGuckin, Jr. et al. |
| 6,818,006 B2 | 11/2004 | Douk et al. |
| 6,837,898 B2 | 1/2005 | Boyle et al. |
| 6,840,950 B2 | 1/2005 | Stanford et al. |
| 6,843,798 B2 | 1/2005 | Kusleika et al. |
| 6,849,061 B2 | 2/2005 | Wagner |
| 6,852,076 B2 | 2/2005 | Nikolic et al. |
| 6,872,217 B2 | 3/2005 | Walak et al. |
| 6,881,218 B2 | 4/2005 | Beyer et al. |
| 6,884,259 B2 | 4/2005 | Tran et al. |
| 6,887,256 B2 | 5/2005 | Gilson et al. |
| 6,972,025 B2 | 12/2005 | WasDyke |
| 6,989,021 B2 | 1/2006 | Bosma et al. |
| 6,991,641 B2 | 1/2006 | Diaz et al. |
| 6,991,642 B2 | 1/2006 | Petersen |
| 7,001,424 B2 | 2/2006 | Patel et al. |
| 7,011,094 B2 | 3/2006 | Rapacki et al. |
| 7,033,376 B2 | 4/2006 | Tsukernik |
| 7,041,117 B2 | 5/2006 | Suon et al. |
| 7,052,511 B2 | 5/2006 | Weldon et al. |
| 7,056,286 B2 | 6/2006 | Ravenscroft et al. |
| 7,147,649 B2 | 12/2006 | Thomas |
| 7,163,550 B2 | 1/2007 | Boismier |
| 7,179,275 B2 | 2/2007 | McGuckin, Jr. et al. |
| 7,232,462 B2 | 6/2007 | Schaeffer |
| 7,261,731 B2 | 8/2007 | Patel et al. |
| 7,279,000 B2 | 10/2007 | Cartier et al. |
| 7,303,571 B2 | 12/2007 | Makower et al. |
| 7,314,477 B1 | 1/2008 | Ravenscroft et al. |
| 7,323,003 B2 | 1/2008 | Lowe |
| 7,331,992 B2 | 2/2008 | Randall et al. |
| 7,338,512 B2 | 3/2008 | McGuckin, Jr. et al. |
| 7,534,251 B2 | 5/2009 | WasDyke |
| 7,544,202 B2 | 6/2009 | Cartier et al. |
| 7,572,289 B2 | 8/2009 | Sisken et al. |
| 7,582,100 B2 | 9/2009 | Johnson et al. |
| 7,625,390 B2 | 12/2009 | Hendriksen et al. |
| 7,699,867 B2 | 4/2010 | Hendriksen et al. |
| 7,704,266 B2 | 4/2010 | Thinnes, Jr. et al. |
| 7,704,267 B2 | 4/2010 | Tessmer |
| 7,722,635 B2 | 5/2010 | Beyer et al. |
| 7,722,638 B2 | 5/2010 | Deyette, Jr. et al. |
| 7,736,383 B2 | 6/2010 | Bressler et al. |
| 7,736,384 B2 | 6/2010 | Bressler et al. |
| 7,749,244 B2 | 7/2010 | Brucheimer et al. |
| 7,749,246 B2 | 7/2010 | McGuckin, Jr. et al. |
| 7,766,932 B2 | 8/2010 | Melzer et al. |
| 7,794,472 B2 | 9/2010 | Eidenschink et al. |
| 7,799,049 B2 | 9/2010 | Ostrovsky et al. |
| 7,887,580 B2 | 2/2011 | Randall et al. |
| 7,967,838 B2 | 6/2011 | Chanduszko et al. |
| 7,972,353 B2 | 7/2011 | Hendriksen et al. |
| 7,993,362 B2 | 8/2011 | Lowe et al. |
| 8,029,529 B1 | 10/2011 | Chanduszko |
| 8,062,327 B2 | 11/2011 | Chanduszko et al. |
| 8,075,606 B2 | 12/2011 | Dorn |
| 8,133,251 B2 | 3/2012 | Ravenscroft et al. |
| 8,241,350 B2 | 8/2012 | Randall et al. |
| 8,333,785 B2 * | 12/2012 | Chanduszko et al. ........ 606/200 |
| 2001/0000799 A1 | 5/2001 | Wessman et al. |
| 2001/0001317 A1 | 5/2001 | Duerig et al. |
| 2001/0016770 A1 | 8/2001 | Allen et al. |
| 2001/0020175 A1 | 9/2001 | Yassour et al. |
| 2001/0023358 A1 | 9/2001 | Tsukernik |
| 2001/0027339 A1 | 10/2001 | Boatman et al. |
| 2001/0039431 A1 | 11/2001 | DeVries et al. |
| 2002/0002401 A1 | 1/2002 | McGuckin et al. |
| 2002/0004060 A1 | 1/2002 | Heublein et al. |
| 2002/0010350 A1 | 1/2002 | Tatsumi et al. |
| 2002/0022853 A1 | 2/2002 | Swanson et al. |
| 2002/0032461 A1 | 3/2002 | Marshall |
| 2002/0038097 A1 | 3/2002 | Corvi et al. |
| 2002/0042626 A1 | 4/2002 | Hanson et al. |
| 2002/0045918 A1 | 4/2002 | Suon et al. |
| 2002/0052626 A1 | 5/2002 | Gilson et al. |
| 2002/0055767 A1 | 5/2002 | Forde et al. |
| 2002/0072764 A1 | 6/2002 | Sepetka et al. |
| 2002/0116024 A1 | 8/2002 | Goldberg et al. |
| 2002/0123720 A1 | 9/2002 | Kusleika et al. |
| 2002/0138097 A1 | 9/2002 | Ostrovsky et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004540 A1 | 1/2003 | Linder et al. |
| 2003/0004541 A1 | 1/2003 | Linder et al. |
| 2003/0004946 A1 | 1/2003 | VanDenAvond et al. |
| 2003/0028241 A1 | 2/2003 | Stinson |

(56) References Cited

U.S. PATENT DOCUMENTS

| | | |
|---|---|---|
| 2003/0055812 A1 | 3/2003 | Williams et al. |
| 2003/0071285 A1 | 4/2003 | Tsukernik |
| 2003/0093106 A1 | 5/2003 | Brady et al. |
| 2003/0093110 A1 | 5/2003 | Vale |
| 2003/0097145 A1 | 5/2003 | Goldberg et al. |
| 2003/0109824 A1 | 6/2003 | Anderson et al. |
| 2003/0109897 A1 | 6/2003 | Walak et al. |
| 2003/0114735 A1 | 6/2003 | Silver et al. |
| 2003/0114880 A1 | 6/2003 | Hansen et al. |
| 2003/0130680 A1 | 7/2003 | Russell |
| 2003/0139765 A1 | 7/2003 | Patel et al. |
| 2003/0153945 A1 | 8/2003 | Patel et al. |
| 2003/0158595 A1 | 8/2003 | Randall et al. |
| 2003/0163159 A1 | 8/2003 | Patel et al. |
| 2003/0171771 A1 | 9/2003 | Anderson et al. |
| 2003/0176888 A1 | 9/2003 | O'Connell |
| 2003/0176912 A1 | 9/2003 | Chuter et al. |
| 2003/0191516 A1 | 10/2003 | Weldon et al. |
| 2003/0195554 A1 | 10/2003 | Shen et al. |
| 2003/0195556 A1 | 10/2003 | Stack et al. |
| 2003/0199918 A1 | 10/2003 | Patel et al. |
| 2003/0208227 A1 | 11/2003 | Thomas |
| 2003/0208229 A1 | 11/2003 | Kletschka |
| 2003/0208253 A1 | 11/2003 | Beyer et al. |
| 2003/0220683 A1 | 11/2003 | Minasian et al. |
| 2004/0006364 A1 | 1/2004 | Ladd |
| 2004/0006369 A1 | 1/2004 | DiMatteo |
| 2004/0059373 A1 | 3/2004 | Shapiro et al. |
| 2004/0068288 A1 | 4/2004 | Palmer |
| 2004/0073252 A1 | 4/2004 | Goldberg et al. |
| 2004/0082966 A1 | 4/2004 | WasDyke |
| 2004/0087999 A1 | 5/2004 | Bosma et al. |
| 2004/0088000 A1 | 5/2004 | Muller |
| 2004/0088001 A1 | 5/2004 | Bosma et al. |
| 2004/0088002 A1 | 5/2004 | Boyle et al. |
| 2004/0093015 A1 | 5/2004 | Ogle |
| 2004/0093064 A1 | 5/2004 | Bosma |
| 2004/0116959 A1 | 6/2004 | McGuckin et al. |
| 2004/0138693 A1 | 7/2004 | Eskuri et al. |
| 2004/0153110 A1 | 8/2004 | Kurz et al. |
| 2004/0153118 A1 | 8/2004 | Clubb et al. |
| 2004/0153119 A1 | 8/2004 | Kusleika et al. |
| 2004/0158267 A1 | 8/2004 | Sancoff et al. |
| 2004/0158273 A1 | 8/2004 | Weaver et al. |
| 2004/0158274 A1 | 8/2004 | WasDyke |
| 2004/0167568 A1 | 8/2004 | Boyle et al. |
| 2004/0172042 A1 | 9/2004 | Suon et al. |
| 2004/0176672 A1 | 9/2004 | Silver et al. |
| 2004/0186510 A1 | 9/2004 | Weaver |
| 2004/0186512 A1 | 9/2004 | Bruckheimer et al. |
| 2004/0193209 A1 | 9/2004 | Pavcnik et al. |
| 2004/0199240 A1 | 10/2004 | Dorn |
| 2004/0199270 A1 | 10/2004 | Wang et al. |
| 2004/0220610 A1 | 11/2004 | Kreidler et al. |
| 2004/0220611 A1 | 11/2004 | Ogle |
| 2004/0230220 A1 | 11/2004 | Osborne |
| 2004/0243173 A1 | 12/2004 | Inoue |
| 2005/0004596 A1 | 1/2005 | McGuckin et al. |
| 2005/0015111 A1 | 1/2005 | McGuckin et al. |
| 2005/0019370 A1 | 1/2005 | Humes |
| 2005/0021075 A1 | 1/2005 | Bonnette et al. |
| 2005/0021076 A1 | 1/2005 | Mazzocchi et al. |
| 2005/0021152 A1 | 1/2005 | Ogle et al. |
| 2005/0027314 A1 | 2/2005 | WasDyke |
| 2005/0027345 A1 | 2/2005 | Horan et al. |
| 2005/0049609 A1 | 3/2005 | Gunderson et al. |
| 2005/0055045 A1 | 3/2005 | DeVries et al. |
| 2005/0055046 A1 | 3/2005 | McGuckin et al. |
| 2005/0059990 A1 | 3/2005 | Ayala et al. |
| 2005/0059993 A1 | 3/2005 | Ramzipoor et al. |
| 2005/0065591 A1 | 3/2005 | Moberg et al. |
| 2005/0070794 A1 | 3/2005 | Deal et al. |
| 2005/0070821 A1 | 3/2005 | Deal et al. |
| 2005/0080447 A1 | 4/2005 | McGuckin et al. |
| 2005/0080449 A1 | 4/2005 | Mulder |
| 2005/0085847 A1 | 4/2005 | Galdonik et al. |
| 2005/0090858 A1 | 4/2005 | Pavlovic |
| 2005/0101982 A1 | 5/2005 | Ravenscroft et al. |
| 2005/0107822 A1 | 5/2005 | WasDyke |
| 2005/0115111 A1 | 6/2005 | Yamashita et al. |
| 2005/0131451 A1 | 6/2005 | Kleshinski et al. |
| 2005/0131452 A1 | 6/2005 | Walak et al. |
| 2005/0159771 A1 | 7/2005 | Petersen |
| 2005/0165441 A1 | 7/2005 | McGuckin et al. |
| 2005/0165442 A1 | 7/2005 | Thinnes et al. |
| 2005/0171473 A1 | 8/2005 | Gerdts et al. |
| 2005/0182439 A1 | 8/2005 | Lowe |
| 2005/0222604 A1 | 10/2005 | Schaeffer |
| 2005/0234503 A1 | 10/2005 | Ravenscroft et al. |
| 2005/0251199 A1 | 11/2005 | Osborne et al. |
| 2005/0267512 A1 | 12/2005 | Osborne et al. |
| 2005/0267513 A1 | 12/2005 | Osborne et al. |
| 2005/0267514 A1 | 12/2005 | Osborne et al. |
| 2005/0267515 A1 | 12/2005 | Oliva et al. |
| 2005/0288703 A1 | 12/2005 | Beyer et al. |
| 2005/0288704 A1 | 12/2005 | Cartier et al. |
| 2006/0004402 A1 | 1/2006 | Voeller et al. |
| 2006/0015137 A1 | 1/2006 | WasDyke et al. |
| 2006/0016299 A1 | 1/2006 | Chen |
| 2006/0030875 A1 | 2/2006 | Tessmer |
| 2006/0036279 A1 | 2/2006 | Eidenschink et al. |
| 2006/0041271 A1 | 2/2006 | Bosma et al. |
| 2006/0047300 A1 | 3/2006 | Eidenschink |
| 2006/0047341 A1 | 3/2006 | Trieu |
| 2006/0069405 A1 | 3/2006 | Schaeffer et al. |
| 2006/0069406 A1 | 3/2006 | Hendriksen et al. |
| 2006/0079928 A1 | 4/2006 | Cartier et al. |
| 2006/0079930 A1 | 4/2006 | McGuckin et al. |
| 2006/0095068 A1 | 5/2006 | WasDyke et al. |
| 2006/0106417 A1 | 5/2006 | Tessmer et al. |
| 2006/0155320 A1 | 7/2006 | Bressler et al. |
| 2006/0157889 A1 | 7/2006 | Chen |
| 2006/0203769 A1 | 9/2006 | Saholt et al. |
| 2006/0206138 A1 | 9/2006 | Eidenschink |
| 2006/0259067 A1 | 11/2006 | Welch et al. |
| 2006/0259068 A1 | 11/2006 | Eidenschink |
| 2007/0005095 A1 | 1/2007 | Osborne et al. |
| 2007/0005104 A1 | 1/2007 | Kusleika et al. |
| 2007/0005105 A1 | 1/2007 | Kusleika et al. |
| 2007/0039432 A1 | 2/2007 | Cutler |
| 2007/0043419 A1 | 2/2007 | Nikolchev et al. |
| 2007/0060944 A1 | 3/2007 | Boldenow et al. |
| 2007/0088381 A1 | 4/2007 | McGuckin et al. |
| 2007/0100372 A1 | 5/2007 | Schaeffer |
| 2007/0112373 A1 | 5/2007 | Carr et al. |
| 2007/0167974 A1 | 7/2007 | Cully et al. |
| 2007/0173885 A1 | 7/2007 | Cartier et al. |
| 2007/0185524 A1 | 8/2007 | Diaz et al. |
| 2007/0191878 A1 | 8/2007 | Segner et al. |
| 2007/0191880 A1 | 8/2007 | Cartier et al. |
| 2007/0198050 A1 | 8/2007 | Ravenscroft et al. |
| 2007/0213685 A1 | 9/2007 | Bressler et al. |
| 2007/0219530 A1 | 9/2007 | Schaeffer |
| 2007/0250106 A1 | 10/2007 | Kim |
| 2008/0014078 A1 | 1/2008 | Suciu et al. |
| 2008/0033479 A1 | 2/2008 | Silver |
| 2008/0039891 A1 | 2/2008 | McGuckin et al. |
| 2008/0091230 A1 | 4/2008 | Lowe |
| 2008/0097518 A1 | 4/2008 | Thinnes et al. |
| 2008/0103582 A1 | 5/2008 | Randall et al. |
| 2008/0119867 A1 | 5/2008 | Delaney |
| 2008/0183206 A1 | 7/2008 | Batiste |
| 2008/0221609 A1 | 9/2008 | McGuckin et al. |
| 2008/0221656 A1 | 9/2008 | Hartley et al. |
| 2008/0255605 A1 | 10/2008 | Weidman |
| 2008/0262506 A1 | 10/2008 | Griffin et al. |
| 2008/0275486 A1 | 11/2008 | Dwyer et al. |
| 2008/0275488 A1 | 11/2008 | Fleming |
| 2008/0294189 A1 | 11/2008 | Moll et al. |
| 2008/0300621 A1 | 12/2008 | Hopkins et al. |
| 2009/0005803 A1 | 1/2009 | Batiste |
| 2009/0043332 A1 | 2/2009 | Sullivan et al. |
| 2009/0069840 A1 | 3/2009 | Hallisey |
| 2009/0105747 A1 | 4/2009 | Chanduszko et al. |

(56) References Cited

U.S. PATENT DOCUMENTS

| | | |
|---|---|---|
| 2009/0131970 A1 | 5/2009 | Chanduszko et al. |
| 2009/0163926 A1 | 6/2009 | Sos |
| 2009/0192543 A1 | 7/2009 | WasDyke |
| 2009/0198270 A1 | 8/2009 | McGuckin, Jr. et al. |
| 2009/0264915 A1 | 10/2009 | WasDyke |
| 2009/0299403 A1 | 12/2009 | Chanduszko et al. |
| 2009/0299404 A1 | 12/2009 | Chanduszko et al. |
| 2009/0318951 A1 | 12/2009 | Kashkarov et al. |
| 2010/0030253 A1 | 2/2010 | Harris et al. |
| 2010/0030254 A1 | 2/2010 | Chanduszko et al. |
| 2010/0049239 A1 | 2/2010 | McGuckin, Jr. et al. |
| 2010/0063535 A1 | 3/2010 | Bressler et al. |
| 2010/0076545 A1 | 3/2010 | Kleshinski et al. |
| 2010/0160956 A1 | 6/2010 | Hendriksen et al. |
| 2010/0174310 A1 | 7/2010 | Tessmer |
| 2010/0222772 A1 | 9/2010 | Kleshinski et al. |
| 2010/0256669 A1 | 10/2010 | Harris et al. |
| 2010/0312269 A1 | 12/2010 | McGuckin, Jr. et al. |
| 2010/0318115 A1 | 12/2010 | Chanduszko et al. |
| 2011/0118823 A1 | 5/2011 | Randall et al. |
| 2011/0257677 A1 | 10/2011 | Carr, Jr. et al. |
| 2012/0065663 A1 | 3/2012 | Chanduszko et al. |
| 2012/0184985 A1 | 7/2012 | Ravenscroft et al. |

FOREIGN PATENT DOCUMENTS

| | | |
|---|---|---|
| DE | 3633527 A1 | 4/1988 |
| EP | 0145166 A2 | 6/1985 |
| EP | 0188927 A2 | 7/1986 |
| EP | 0712614 A1 | 5/1996 |
| EP | 1042996 A2 | 10/2000 |
| EP | 1092401 A1 | 4/2001 |
| EP | 1336393 A2 | 8/2003 |
| EP | 1475110 A1 | 11/2004 |
| FR | 2567405 A1 | 1/1986 |
| FR | 2718950 A1 | 10/1995 |
| FR | 2781143 A1 | 1/2000 |
| FR | 2791551 A1 | 10/2000 |
| JP | 08257031 | 10/1996 |
| JP | 2002525183 A | 8/2002 |
| JP | 2003521970 A | 7/2003 |
| JP | 2005503199 A | 2/2005 |
| JP | 4851522 B2 | 1/2012 |
| SV | 07A000025 | 4/1997 |
| WO | 9509567 A1 | 4/1995 |
| WO | 9534339 A1 | 12/1995 |
| WO | 9612448 A1 | 5/1996 |
| WO | 9617634 A2 | 6/1996 |
| WO | 9729794 A1 | 8/1997 |
| WO | 9802203 A1 | 1/1998 |
| WO | 9823322 A1 | 6/1998 |
| WO | 9925252 A1 | 5/1999 |
| WO | 0012011 A1 | 3/2000 |
| WO | 0018467 A1 | 4/2000 |
| WO | 0056390 A1 | 9/2000 |
| WO | 0076422 A1 | 12/2000 |
| WO | 0117457 A1 | 3/2001 |
| WO | 0204060 A1 | 1/2002 |
| WO | 02055125 A2 | 7/2002 |
| WO | 02102436 A2 | 12/2002 |
| WO | 03003927 A1 | 1/2003 |
| WO | 03004074 A3 | 1/2003 |
| WO | 03073961 A1 | 9/2003 |
| WO | 2004012587 A2 | 2/2004 |
| WO | 2004049973 A1 | 6/2004 |
| WO | 2004098459 A1 | 11/2004 |
| WO | 2004098460 A1 | 11/2004 |
| WO | 2005009214 A2 | 2/2005 |
| WO | 2005072645 A1 | 8/2005 |
| WO | 2005102212 A1 | 11/2005 |
| WO | 2005102437 A2 | 11/2005 |
| WO | 2005102439 A2 | 11/2005 |
| WO | 2006036457 A2 | 4/2006 |
| WO | 2006055174 A2 | 5/2006 |
| WO | 2006124405 A2 | 11/2006 |
| WO | 2007021340 A1 | 2/2007 |
| WO | 2007079410 A2 | 7/2007 |
| WO | 2007100619 A2 | 9/2007 |
| WO | 2007106378 A2 | 9/2007 |
| WO | 2007143602 A2 | 12/2007 |
| WO | 2008051294 A2 | 5/2008 |
| WO | 2008076970 A1 | 6/2008 |
| WO | 2008077067 A2 | 6/2008 |
| WO | 2008109131 A2 | 9/2008 |

OTHER PUBLICATIONS

WO95_09567, Kim et al., date: 1995.*

Gamblin, T.C. et al., "A Prospective Evaluation of a Bedside Technique for Placement of Inferior Vena Cava Filters: Accuracy and Limitations of Intravascular Ultrasound", The American Surgeon, May 2003, vol. 69, pp. 382-386.

Garcia, N. D., "Is Bilateral Ultrasound Scanning of the Legs Necessary for Patients With Unilateral Symptoms of Deep Vein Thrombosis", Journal of Vascular Surgery, 2001, 34:792-797.

Gayer, G. et al., "Congenital Anomalies of the Inferior Vena Cava Revealed on CT in Patients With Deep Vein Thrombosis", American Journal of Roentgenology, Mar. 2003, vol. 180, pp. 729-732.

Geerts, W.H., "A Prospective Study of Venous Thromboembolism After Major Trauma", Dec. 15, 1994, vol. 331, No. 24, pp. 1601-1606.

Gelbfish, G. A. et al., "Intracardiac and Intrapulmonary Greenfield Filters: A Long-Term Follow-Up", Journal of Vascular Surgery, Nov. 1991, Vo. 14, No. 5, pp. 614-617.

Gelfand, E.V. et al., "Venous Thromboembolism Guidebook, Fourth Edition", Critical Pathways in Cardiology, Dec. 2003, vol. 2, No. 4, pp. 247-265.

Georgopoulos, S.E. et al., "Paradoxical Embolism", Journal of Cardiovascular Surgery, 2001, 42:675-677.

Ginsberg, M.S. et al., "Clinical Usefulness of Imaging Performed After CT Angiography That Was Negative for Pulmonary Embolus in a High-Risk Oncologic Population", American Journal of Roentgenology, Nov. 2002, 179:1205-1208.

Girard, P. et al., Medical Literature and Vena Cava Filters, Chest, 2002, 122:963-967.

Girard, T. D. et al., "Prophylactic Vena Cava Filters for Trauma Patients: A Systematic Review of the Literature", Thrombosis Research, 2003, 112:261-267.

Goldberg, M.E., "Entrapment of an Exchange Wire by an Inferior Vena Caval Filter: A Technique for Removal", Anesth Analg., Apr. 2003, 96:4, 1235-1236.

Goldhaber, S.Z. et al., "Acute Pulmonary Embolism: Part II Risk Stratification, Treatment, and Prevention", Circulation, 2003, 108:2834-2838.

Goldhaber, S.Z., "A Free-Floating Approach to Filters", Archives of Internal Medicine, Feb. 10, 1997, vol. 157, No. 3, pp. 264-265.

Goldhaber, S.Z., "Venous Thromboembolism in the Intensive Care Unit: The Last Frontier for Pro . . . ", Chest, Jan. 1998, 113(1):5-7.

Goldman, H.B. et al., "Ureteral Injury Secondary to an Inferior Vena Caval Filter", The Journal of Urology, Nov. 1996, vol. 156, No. 5, p. 1763.

Golueke, P.J. et al., "Interruption of the Vena Cava by Means of the Greenfield Filter: Expanding the Indications", Surgery, Jan. 1988, vol. 103, No. 1, pp. 111-117.

Gonze, M.D. et al., "Orally Administered Heparin for Preventing Deep Venous Thrombosis", American Journal of Surgery, Aug. 1998, vol. 176, pp. 176-178.

Goodman, L.R. et al., "Subsequent Pulmonary Embolism: Risk After a Negative Helical CT Pulmonary Angiogram-Prospective Comparison With Scintigraphy", Radiology, 2000, 215:535-542.

Gosin, J. S., "Efficacy of Prophylactic Vena Cava Filters in High-Risk Trauma Patients", Annals of Vascular Surgery, 1997, 11:100-105.

Gottlieb, R.N., "Randomized Prospective Study Comparing Routine Versus Selective Use of Sonography of the Complete Calf in Patients With Suspected Deep Venous Thrombosis", American Journal of Roentgenology, Jan. 2003, 180:241-245.

(56) References Cited

OTHER PUBLICATIONS

Grandas, O.H. et al., "Deep Venous Thrombosis in the Pediatric Trauma Population: An Unusual Event: Report of Three Cases", The American Surgeon, Mar. 2000, vol. 66, pp. 273-276.
Grassi, C.L. et al., "Quality Improvement Guidelines for Percutaneous Permanent Inferior Vena Cava Filter Placement for the Prevention of Pulmonary Embolism", Journal of Vascular and Interventional Radiology, Sep. 2003, 14:S271-S275.
Grassi, C.L. et al., "Vena Caval Occlusion After Simon Nitinol Filter Placement: Identification With MR Imaging in Patients With Malignancy", Journal of Vascular and Interventional Radiology, 1992, 3(3):535-539.
Greene, F.L. et al., Letters to the Editor, The Journal of Trauma: Injury, Infection, and Critical Care, May 2005, vol. 5 8, No. 5, pp. 1091-1092.
Greenfield, L. J. et al., "Clinical Experience With the Kim-Ray Greenfield—Vena Caval Filter", Ann Surg, Jun. 1977, vol. 185, No. 6, pp. 692-698.
Greenfield, L. J. et al., "Experimental Embolic Capture by Asymmetric Greenfield Filters", Journal of Vascular Surgery, Sep. 1992, vol. 16, No. 3, pp. 436-444.
Greenfield, L.J. et al., "Filter Complications and Their Management", Seminars in Vascular Surgery, vol. 13, No. 3, Sep. 2000, pp. 213-216.
Greenfield, L.J. et al., "Free-Floating Thrombus and Pulmonary Embolism/Reply", Archives of Internal Medicine, Dec. 8-Dec. 22, 1997, pp. 2661-2662.
Greenfield, L.J. et al., "Limb Asymmetry in Titanium Greenfield Filters: Clinically Significant?", Journal of Vascular Surgery, 1997, 26:770-775.
Greenfield, L.J. et al., "Prophylactic Vena Caval Filters in Trauma: The Rest of the Story", Journal of Vascular Surgery, 2000, 32:490-497.
Greenfield, L.J. et al., "Recommended Reporting Standards for Vena Caval Filter Placement and Patient Follow-Up", Journal of Vascular and Interventional Radiology, 1999, 10:1013-1019.
Greenfield, L.J. et al., "Results of a Multicenter Study of the Modified Hook-Titanium Greenfield Filter" Journal of Vascular Surgery 14:253-257 (Sep. 1991).
Greenfield, L.J. et al., "The Percutaneous Greenfield Filter: Outcomes and Practice Patterns", Journal of Vascular Surgery, 2000, 32:888-893.
Greenfield, L.J. et al., "Twenty-Year Clinical Experience With the Greenfield Filter", Cardiovascular Surgery, Apr. 1995, vol. 3, No. 2, pp. 199-205.
Greenfield, L.J., "Cost vs Value in Vena Caval Filters", Chest, Jul. 1998, vol. 114, No. 1, pp. 9-10.
Greenfield, L.J., "Current Indications for and Results of Greenfield Filter Placement", Journal Vascular Surgery, May 1984, vol. 1, No. 3, pp. 502-504.
Greenfield, L.J., "Does Cervical Spinal Cord Injury Induce Higher Incidence of Complications After Prophylactic Greenfield Filter Usage?", Journal of Vascular and Interventional Radiology, Jul.-Aug. 1997, pp. 719-720.
Greenfield, L.J., "Recurrent Thromboembolism in Patients With Vena Cava Filters", Journal of Vascular Surgery, 2001, 33:510-514.
Greenfield, L.J., "Staging of Fixation and Retrievability of Greenfield Filters", Journal of Vascular Surgery, Nov. 1994, vol. 20, No. 5, pp. 744-750.
Greenfield, Lazar J. et al., "A New Intracaval Filter Permitting Continued Flow and Resolution of Emboli", Surgery, Apr. 1973, vol. 73, No. 4, pp. 599-606.
Greenfield, Lazar J. et al., "Suprarenal Filter Placement", Journal of Vascular Surgery, Sep. 1998, 28:432-438.
Greenfield, Lazar J. et al., "Vena Caval Filter Use in Patients With Sepsis", Archives of Surgery, Nov. 2003, vol. 138, No. 11, Health & Medical Complete, pp. 1245-1248.
Greenfield, Lazar J. et al., "Extended Evaluation of the Titanium Greenfield Vena Caval Filter", Journal of Vascular Surgery, Nov. 1994, vol. 20, No. 3, pp. 458-465.

Günther, Rolf W. et al., "Vena Caval Filter to Prevent Pulmonary Embolism: Experimental Study", Radiology, Aug. 1985,156:315-320.
Haage, Patrick et al., "Prototype Percutaneous Thrombolytic Device: Preclinical Testing in Subacute Inferior Vena Caval Thrombosis in a Pig Model", Radiology, Jul. 2001,220:135-141.
Hagspiel, K.D. et al., "Inferior Vena Cava Filters: An Update", Applied Radiology, Nov. 1998, pp. 20-34.
Hagspiel, K.L. et al., "Difficult Retrieval of a Recovery IVC Filter", Journal of Vascular and Interventional Radiology (Letters to the Editor), Jun. 2004, vol. 15, No. 6, pp. 645-650.
Hainaux, B. et al., "Intragastric Band Erosion After Laparoscopic Adjustable Gastric Banding for Morbid Obesity: Imaging Characteristics of an Underreported Complication", American Journal of Roentgenology, Jan. 2005, 184:109-112.
Hak, D.J., "Prevention of Venous Thromboembolism in Trauma and Long Bone Fractures", Current Opinion in Pulmonary Medicine, 2001, 7:338-343.
Hammer, Frank D. et al., "In Vitro Evaluation of Vena Cava Filters", Journal of Vascular and Interventionai Radiology, Nov.-Dec. 1994, 5:869-876.
Stecker, M. S. et al., "Evaluation of a Spiral Nitinol Temporary Inferior Vena Caval Filter", Academic Radiology, 2001, 8:484-493.
Stein, P. D. et al., "Deep Venous Thrombosis in a General Hospital", Chest, 2002, 122:960-962.
Stein, P. D., "Opinions Regarding the Diagnosis and Management of Venous Thromboembolic Disease", Chest, Feb. 1998, vol. 113, No. 2, pp. 499-504.
Still, J. et al., "Experience With the Insertion of Vena Caval Filters in Acutely Burned Patients", The American Surgeon, Mar. 2000, vol. 66, No. 3, pp. 277-279.
Stoneham G. W. et al., "Temporary Inferior Vena Cava Filters: In Vitro Comparison With Permanent IVC Filters", Journal of Vascular and Interventional Radiology, Sep.-Oct. 1995, vol. 6, pp. 731-736.
Stosslein, F. et al., "A Rare Complication With an Antheor Vena Cava Filter", Cardiovascular and Interventional Radiology, 1998, 21:165-167.
Stover, M. D. et al., "Prospective Comparison of Contrast-Enhanced Computed Tomography Versus Magnetic Resonance Venography in the Detection of Occult Deep Pelvic Vein Thrombosis in Patients With Pelvic and Acetabular Fractures", Journal of Orthopaedic Trauma, 2002, 16(9):613-621.
Streib, E. W. et al., "Complications of Vascular Access Procedures in Patients With Vena Cava Filters", The Journal of Trauma: Injury Infection, and Critical Care, Sep. 2000, vol. 49, No. 3, pp. 553-558.
Streiff, Michael B., "Vena Caval Filters: A Comprehensive Review", Blood, Jun. 15, 2000, vol. 95, No. 12, pp. 3669-3677.
Sue, L. P. et al., "Iliofemoral Venous Injuries: An Indication for Prophylactic Caval Filter Placement", The Journal of Trauma: Injury, Infection, and Critical Care, 1995, vol. 39, No. 4, pp. 693-695.
Sugerman, H. J. et al., "Risks and Benefits of Gastric Bypass in Morbidity Obese Patients With Severe Venous Stasis Disease", Annals of Surgery, 2001, vol. 234, No. 1, pp. 41-46.
Sultan, S. et al., "Operative and Endovascular Management of Extracranial Vertebral Artery Aneurysm in Ehlers-Danlos Syndrome: A Clinical Dilemma", Vascular and Endovascular Surgery, 2002, 36(5):389-392.
Taheri, S. A. et al., "Case Report: A Complication of the Greenfield Filter: Fracture and Distal Migration of Two Struts-A Case Report", Journal of Vascular Surgery, Jul. 1992, vol. 16, No. 1, pp. 96-99.
Tai, N. R. M. et al., "Modern Management of Pulmonary Embolism", British Journal of Surgery, 1999, 86:853-868.
Tardy, B. et al, "Older People Included in a Venous Thrombo-Embolism Clinical Trial: A Patients' Viewpoint", Age and Ageing, 2003, 32:149-153.
Tay, Kiang-Hiong et ai, "Repeated Gunther Tulip Inferior Vena Cava Filter Repositioning to Prolong Implantation Time", J Vasc Interv Radioi, May 2002, 13:509-512.
Taylor, Frank C. et al., "Vena Tech Vena Cava Filter: Experience and Early Follow-up", Journal of Vascular Interventional Radiology, Nov. 1991, 2:435-440.
Teitelbaum, G. P. et al., Low-Artifact Intravascular Devices: MR Imaging Evaluation, Radiology, Sep. 1988, 168:713-719.

(56) References Cited

OTHER PUBLICATIONS

Terhaar, Olaf Alfons et al., "Extended Interval for Retrieval of Gunther Tulip Filters", J Vascinterv Radioi, Nov. 2004,15:1257-1262.
The Simon Nitinol Filter, Instructions for Use, Nitnol Medical Technologies, Inc.
Thery, C. et al., "Use of a New Removable Vena Cava Filter in Order to Prevent Pulmonary Embolism in Patients Submitted to Thrombolysis", European Heart Journal, 1990, vol. 11,334-341.
Thomas, J. H. et al., "Vena Caval Occlusion After Bird's Nest Filter Placement", American Journal of Surgery, Dec. 1998, vol. 176, pp. 598-600.
Thomas, L. A. et al., "Use of Greenfield Filters in Pregnant Women at Risk for Pulmonary Embolism", Southern Medical Journal, Feb. 1997, vol. 90, Issue 2.
Tillie-Leblond, I. et al., "Risk of Pulmonary Embolism After a Negative Spiral CT Angiogram in Patients With Pulmonary Disease: 1-Year Clinical Follow-Up Study", Radiology, 2002, 223:461-467.
Tola, J. C. et al., "Bedside Placement of Inferior Vena Cava Filters in the Intensive Care Unit", The American Surgeon, Sep. 1999, vol. 65, No. 9, pp. 833-838.
Tovey, C. et al., "Diagnosis, Investigation, and Management of Deep Vein Thrombosis", British Medical Journal, May 31, 2003, vol. 326, i7400, p1180(5), 9 pages.
Trerotola, S. O. et al., "Mechanical Thrombolysis of Venous Thrombosis in an Animal Model With Use of Temporary Caval Filtration", Journal of Vascular and Interventional Radiology, Sep. 2001, 12:1075-1085.
Trerotola, S. O. et al., "Preclinical in Vivo Testing of the Arrow-Trerotola Percutaneous Thrombolytic Device for Venous Thrombosis", Journal of Vascular and Interventional Radiology, 2001, 12:95-103.
Trujillo-Santos,J. et al., "Bed Rest or Ambulation in the Initial Treatment of Patients With Acute Deep Vein Thrombosis or Pulmonary Embolism", Chest, 2005, 127:1631-1636.
Tuna, I. C. et al., "Massive Pulmonary Embolus", Texas Heart Institute Journal, 2002, vol. 29, No. 2, pp. 144-145.
Uflacker, R., "Interventional Therapy for Pulmonary Embolism", Journal of Vascular Interventional Radiology, Feb. 2001, 12:147-164.
Urena, R. et al., "Bird's Nest Filter Migration to the Right Atrium", American Journal of Roentgenology, Oct. 2004, 183:1037-1039.
U.S. Appl. No. 09/640,865, filed Aug. 18, 2000 Advisory Action dated Apr. 19, 2007.
U.S. Appl. No. 09/640,865, filed Aug. 18, 2000 Advisory Action dated Mar. 23, 2006.
U.S. Appl. No. 09/640,865, filed Aug. 18, 2000 Final Office Action dated Jan. 16, 2007.
U.S. Appl. No. 09/640,865, filed Aug. 18, 2000 Final Office Action dated Nov. 30, 2005.
U.S. Appl. No. 09/640,865, filed Aug. 18, 2000 Non-Final Office Action dated Apr. 7, 2005.
U.S. Appl. No. 09/640,865, filed Aug. 18, 2000 Non-Final Office Action dated Aug. 8, 2006.
U.S. Appl. No. 09/640,865, filed Aug. 18, 2000 Non-Final Office Action dated Jun. 5, 2003.
U.S. Appl. No. 10/079,155, filed Feb. 20, 2002 Final Office Action dated Jan. 20, 2006.
U.S. Appl. No. 10/079,155, filed Feb. 20, 2002 Non-Final Office Action dated Jul. 13, 2004.
U.S. Appl. No. 10/079,155, filed Feb. 20, 2002 Non-Final Office Action dated Mar. 7, 2007.
U.S. Appl. No. 10/079,155, filed Feb. 20, 2002 Non-Final Office Action dated Nov. 20, 2006.
U.S. Appl. No. 10/079,155, filed Feb. 20, 2002 Non-Final Office Action dated Sep. 11, 2006.
U.S. Appl. No. 11/150,661, filed Jun. 10, 2005 Final Office Action dated May 27, 2010.
U.S. Appl. No. 11/150,661, filed Jun. 10, 2005 Non-Final Office Action dated Jul. 22, 2011.
U.S. Appl. No. 11/150,661, filed Jun. 10, 2005 Non-Final Office Action dated Nov. 5, 2009.
U.S. Appl. No. 11/334,829, filed Jan. 19, 2006 Non-Final Office Action dated Aug. 18, 2008.
U.S. Appl. No. 11/429,975, filed May 9, 2006 Non-Final Office Action dated Oct. 7, 2010.
U.S. Appl. No. 11/429,975, filed May 9, 2006 Notice of Allowance dated Feb. 18, 2011.
Kazmers, A. et al., "Pulmonary Embolism in Veterans Affairs Medical Centers: Is Vena Cava Interruption Underutilized?", The American Surgeon, Dec. 1999, vol. 65, No. 12, pp. 1171-1175.
Kearon, C. et al., "Management of Anticoagulation Before and After Elective Surgery", The New England Journal of Medicine, May 22, 1997, vol. 336, No. 21, pp. 1506-1511.
Kellum, J. M., "Gastric Banding" Annals of Surgery, Jan. 2003, vol. 237, No. 1, pp. 17-18.
Kelly, J. et al., "Anticoagulation or Inferior Vena Cava Filter Placement for Patients With Primary Intracerebral Hemorrhage Developing Venous Thromboembolism?", Stroke, 2003, 34:2999-3005.
Kercher, K. et al., "Overview of Current Inferior Vena Cava Filters", The American Surgeon, Aug. 2003, vol. 69, pp. 643-648.
Kerlan, R.K., Jr. et al., "Residual Thrombus Within a Retrievable IVC Filter", Journal of Vascular and Interventional Radiology, 16:555-557.
Kerr, A. et al., "Bidirectional Vena Cava Filter Placement", Journal of Vascular Surgery, Oct. 1995, vol. 22, No. 4.
Khansarinia, S. et al., Prophylactic Greenfield Filter Placement in Selected High-Risk Trauma Patients, Journal of Vascular Surgery, 1995, 22:231-236.
Kim et al., "Insertion of the Simon Nitinol Caval Filter: Value of the Antecubital Vein Approach" AJR 157:521-522 (Sep. 1991).
Kim et al., "Perforation of the Inferior Vena Cava with Aortic and Vetebral Penetration by a Suprarenal Greenfield Filter" Radiology 172:721-723 (1989).
Kim et al., "The Simon Nitinol Filter: Evaluation by MR and Ultrasound" Angiology 43:541-548 (Jul. 1992).
Kim et al., "Vena Cava Filter Placement Via the External Jugular Vein" AJR 155:898-899 (Oct. 1990).
Kim, D. et al., "Insertion of the Simon Nitinol Caval Filter: Value of the Antecubital Vein Approach", American Journal of Roentgenology, Sep. 1991, 157:521-522.
Kim, J. et al., "Preliminary Report on the Safety of Heparin for Deep Venous Thrombosis Prophylaxis After Severe Head Injury", The Journal of Trauma: Injury, Infection, and Critical Care, Jul. 2002, vol. 53, No. 1, pp. 38-43.
Kim, V. et al., "Epidemiology of Venous Thromboembolic Disease", Emergency Medicine Clinics of North America, Nov. 2001, vol. 19, No. 4, pp. 839-859.
Kimmerly, W. S. et al., "Graduate Surgical Trainee Attitudes Toward Postoperative Thromboprophylaxis", Southern Medical Journal, Aug. 1999, vol. 92, No. 9, pp. 790-794.
King, J.N. et al., "Vena Cava Filters", The Western Journal of Medicine, Mar. 1992, vol. 156, No. 3, pp. 295-296.
Kinney, T. B. et al., "Regarding "Limb Asymmetry in Titanium Greenfield Filters: Clinically Significant?"", Journal of Vascular Surgery, Jun. 1998, vol. 27, No. 6.
Kinney, T.B. et al., "Does Cervical Spinal Cord Injury Induce a Higher Incidence of Complications After Prophylactic Greenfield Inferior Vena Cava Filter Usage?", Journal of Vascular and Interventional Radiology, 1996, 7:907-915.
Kinney, T.B. et al., "Fatal Paradoxic Embolism Occurring During IVC Filter Insertion in a Patient With Chronic Pulmonary Thromboembolic Disease", Journal of Vascular and Interventional Radiology, 2001, 12:770-772.
Kinney, T.B., "Translumbar High Inferior Vena Cava Access Placement in Patients With Thrombosed Inferior Vena Cava Filters", Journal of Vascular and Interventional Radiology, 2003, 14:1563-1567.
Kinney, T.B., "Update on Inferior Vena Cava Filters", Journal of Vascular and Interventional Radiology, 2003, 14:425-440.
Kistner, R. L., Definitive Diagnosis and Definitive Treatment in Chronic Venous Disease: A Concept Whose Time Has Come:, Journal of Vascular Surgery, Nov. 1996, vol. 24, No. 5, pp. 703-710.

(56) References Cited

OTHER PUBLICATIONS

Knudson, M. M. et al., "Prevention of Venous Thromboembolism in Trauma Patients", The Journal of Trauma, Sep. 1994, vol. 37, No. 3, pp. 480-487.
Knudson, M. M. et al., "Thromboembolism After Trauma—An Analysis of 1602 Episodes From the American College of Surgeons National Trauma Data Bank" Annals of Surgery, Sep. 2004, vol. 240, No. 3, pp. 490-498.
Knudson, M. M. et al., Thromboembolism Following Multiple Trauma, The Journal of Trauma, Jan. 1992, vol. 32, No. 1, pp. 2-11.
Knudson, M. M. et al., "Venous Thromboembolism After Trauma", Current Opinion in Critical Care, 2004, 10:539-548.
Koga, F. et al., "Deep Vein Thrombosis During Chemotherapy in a Patient With Advanced Testicular Cancer: Successful Percutaneous Thrombectomy Under Temporary Placement of Retrievable Inferior Vena Cava Filter", International Journal of Uroloty, 2001, 8:90-93.
Konya, A. et al., "New Embolization Coil Containing a Nitinol Wire Core: Preliminary in Vitro and in Vivo Experiences", Journal of Vascular and Interventional Radiology, 2001, 12:869-877.
Kozak, T.K.W. et al., "Massive Pulmonary Thromboembolism After Manipulation of an Unstable Pelvic Fracture: A Case Report and Review of the Literature", The Journal of Trauma: Injury, Infection, and Critical Care, 1995, vol. 38, pp. 366-367.
Kraimps, J. et al., "Optical Central Trapping (OPCETRA) Vena Caval Filter: Results of Experimental Studies", Journal of Vascular and Interventional Radiolory, 1992, 3:697-701.
Kreutzer J.et al., "Healing Response to the Clamshell Device for Closure of Intracardiac Defects in Humans", Catheterization and Cardiovascular Interventions, 2001, vol. 54.
Kronemyer, B., Temporary Filter Traps Pulmonary Emboly, Orthopedics Today, p. 34.
Kudsk, K. A. et al., "Silent Deep Vein Thrombosis in Immobilized Multiple Trauma Patients", The American Journal of Surgery, Dec. 1989, vol. 158, pp. 515-519.
Kupferschmid, J.P. et al., "Case Report: Small-Bowel Obstruction From an Extruded Greenfield Filter Strut: An Unusual Late Complication", Journal of Vascular Surgery, Jul. 1992, vol. 16, No. 1, pp. 113-115.
Kurgan, A. et al., "Case Reports: Penetration of the Wall of an Abdominal Aortic Aneurysm by a Greenfield Filter Prong: A Late Complication", Journal of Vascular Surgery, Aug. 1993, vol. 18, No. 2, pp. 303-306.
Kuszyk, B. et al., "Subcutaneously Tethered Temporary Filter: Pathologic Effects in Swine", Journal of Vascular and Interventional Radiology, Nov.-Dec. 1995, Vo. 6, No. 6, pp. 895-902.
Kyrle, P. A. et al., Deep Vein Thrombosis, The Lancet, Mar. 26-Apr. 1, 2005, 365(9465):1163-1174.
Langan III, E. M. et al., "Prophylactic Inferior Vena Cava Filters in Trauma Patients at High Risk: Follow-Up Examination and Risk/Benefit Assessment", Journal of Vascular Surgery, 1999, 30:484-490.
Leach, T. A. et al., "Surgical Prophylaxis for Pulmonary Embolism", The American Surgeon, Apr. 1994, vol. 60, No. 4, pp. 292-295.
Leask, R.L. et al., "Hemodynamic Effects of Clot Entrapment in the TrapEase Inferior Vena Cava Filter", Journal of Vascular and Interventional Radiology, 2004, 15:485-490.
Leask, R.L. et al., "In Vitro Hemodynamic Evaluation of a Simon Nitinol Vena Cava Filter: Possible Explanation of IVC Occlusion", Journal of Vascular and Interventional Radiology, 2001, 12:613-618.
Lemmon, G.W. et al., "Incomplete Caval Protection Following Suprarenal Caval Filter Placement", Angiology The Journal of Vascular Diseases, Feb. 2000, vol. 51, No. 2, pp. 155-159.
Leoni, C. J. et al., "Classifying Complications of Interventional Procedures: A Survey of Practicing Radiologists", Journal of Vascular and Interventional Radiology, 2001, 12:55-59.
Letai, A., "Cancer, Coagulation, and Anticoagulation", The Oncologist, 1999, 4:443-449.
Lewis-Carey, M. B. et al., "Temporary IVC Filtration Before Patent Foramen Ovale Closure in a Patient With Paradoxic Embolism", Journal of Vascular and Interventional Radiology, 2002, 13:1275-1278.

Lidagoster, M. I. et al., Superior Vena Cava Occlusion After Filter Insertion, Journal of Vascular Surgery, Jul. 1994, vol. 20, No. 1.
Lin, J. et al., "Factors Associated With Recurrent Venous Thromboembolism in Patients With Malignant Disease", Journal of Vascular Surgery, 2003, 37:976-983.
Lin, M. et al., "Successful Retrieval of Infected Gunther Tulip IVC Filter", Journal of Vascular and Interventional Radiology, 2000, 11:1341-1343.
Lin, P. H. et al., "The Regained Referral Ground and Clinical Practice of Vena Cava Filter Placement in Vascular Surgery", The American Surgeon, Oct. 2002, vol. 68, No. 10, pp. 865-870.
Linsenmaier U. et al, "Indications, Management, and Complications of Temporary Inferior Vena Cava Filters", Cardiovascular and Interventional Radiology, 1998, 21:464-469.
Lipman, J.C., "Removal of Vena Caval Filter at 224 Days", Southern Medical Journal, May 2005, vol. 98, No. 5, pp. 556-558.
Loehr, S.P. et al., "Retrieval of Entrapped Guide Wire in an IVC Filter Facilitated With Use of a Myocardial Biopsy Forceps and Snare Device", Journal of Vascular and Interventional Radiology (Letter to Editor), Sep. 2001, vol. 12, No. 9, pp. 1116-1118.
Lopez-Beret, P. et al., "Systematic Study of Occult Pulmonary Thromboembolism in Patients With Deep Venous Thrombosis", Journal of Vascular Surgery, 2001, 33:515-521.
Lorch, H. et al., "Current Practice of Temporary Vena Cava Filter Insertion: A Multicenter Registry", Journal of Vascular and Interventional Radiology, 2001, 11:83-88.
Lorch, H. et al., "In Vitro Studies of Temporary Vena Cava Filters", Cardiovascular and Interventional Radiology, 1998, 21:146-150.
Lorch, H. et al., "Temporary Vena Cava Filters and Ultrahigh Streptokinase Thrombolysis Therapy: A Clinical Study", Cardiovascular Interventional Radiology, 2000, 23:273-278.
Lujan, J. A. et al., "Laparoscopic Versus Open Gastric Bypass in the Treatment of Morbid Obesity", Annals of Surgery, Apr. 2004, vol. 239, No. 4, pp. 433-437.
Lund, G. et al., "A New Vena Caval Filter for Percutaneous Placement and Retrieval Experimental Study", Radiology, 1984, 152:369-372.
Lund, G. et al., "Retrievable Vena Caval Filter Percutaneously Introduced", Radiology, 1985, vol. 155, p. 831.
Luo, X. Y. et al., "Non-Newtonian Flow Patterns Associated With an Arterial Stenosis", Journal of Biomechanical Engineering, Nov. 1992, 114:512-514.
MacDonald, K. G. Jr., "Overview of the Epidemiology of Obesity and the Early History of Procedures to Remedy Morbid Obesity", Archives of Surgery, Apr. 2003, 138(4):357-360.
Machado, L.G. et al., "Medical Applications of Shape Memory Alloys", Brazilian Journal of Medical and Biological Research, 2003, 36:683-691.
Magnant, J.G. et al., "Current Use of Inferior Vena Cava Filters", Journal of Vascular Surgery, Nov. 1992, vol. 16, No. 5, pp. 701-706.
Malden et al., "Transvenous Retreival of Misplaced Stainless Steel Greenfield Filters" JVIR 3:703-708 (1992).
Manke, C. et al., "MR Imaging-Guided Stent Placement in Iliac Arterial Stenoses: A Feasibility Study", Radioilogy, 2001, 219:527-534.
Marston, W.A. et al., "Re: Comparison of the AngioJet Rheolytic Catheter to Surgical Thrombectomy for the Treatment of Thrombosed Hemodialysis Grafts", Journal of Vascular and Interventional Radiology (Letters to the Editor), Sep. 2000, vol. 11, No. 8, pp. 1095-1099.
Matteson, B. et al., "Role of Venous Duplex Scanning in Patients With Suspected Pulmonary Embolism", The Journal of Vascular Surgery, 1996, 24:768-773.
Matthews, B. D. et al., "Inferior Vena Cava Filter Placement: Preinsertion Inferior Vena Cava Imaging", The American Surgeon, Aug. 2003, vol. 69, No. 8, pp. 649-653.
Mattos, M.A. et al., "Prevalence and Distribution of Calf Vein Thrombosis in Patients With Symptomatic Deep Venous Thrombosis: A Color-Flow Duplex Study", Journal of Vascular Surgery, 1996, 24:738-744.
Maxwell, R.A. et al., "Routine Prophylactic Vena Cava Filtration is Not Indicated After Acute Spinal Cord Injury", The Journal of Trauma: Injury, Infection, and Critical Care, 2002, 52:902-906.

(56) References Cited

OTHER PUBLICATIONS

McCowan, T.C. et al., "Complications of the Nitinol Vena Caval Filter", Journal of Vascular and Interventional Radiology, 1992, 3:401-408.

McMurtry, A.L. et al., "Increased Use of Prophylactic Vena Cava Filters in Trauma Patients Failed to Decrease Overall Incidence of Pulmonary Embolism", Journal of the American College of Surgeons, 1999, 189:314-320.

Meissner, M.H. et al., Venous Thromoembolism in Trauma: A Local Manifestation of Systemic Hypercoagulability?, The Journal of Trauma: Injury, Infection, and Critical Care, Feb. 2003, vol. 54, No. 2, pp. 224-231.

Melinek, J. et al., "Autopsy Findings Following Gastric Bypass Surgery for Morbid Obesity", Arch Path Lab Med, 2002 126:1091-1095.

Mihara, H. et al., "Use of Temporary Vena Cava Filters After Catheter-Directed Fragmentation and Thrombolysis in Patients With Acute Pulmonary Thromboembolism", Japanese Circulartion Journal, Jun. 1998, vol. 62, pp. 462-464.

Miller, A. C., "British Thoracic Society Guidelines for the Management of Suspected Acute Pulmonary Embolism", Thorax, Jun. 2003, 58(6): 470-483.

Miller, Karl E., "Indications for Vena Cava Filters for Recurrent DVT", American Family Physician, Feb. 1, 2003, vol. 67, No. 3, p. 593.

Millward, S., "Temporary IVC Filtration Before Patent Foramen Ovale Closure in a Patient With Paradoxic Embolism", Letter to the Editor, p. 937.

Millward, S.F. et a l., "Preliminary Clinical Experience with the Gunther Temporary Inferior Vena Cava Filter", Journal of Vascular and Interventional Radiology, 1994, 5:863-868.

Millward, S.F. et al., "Gunther Tulip Filter" Preliminary Clinical Experience With Retrieval, Journal of Vascular and Interventional Radiology, 2000, 11:75-82.

Millward, S.F. et al., "Gunther Tulip Retrievable Vena Cava Filter: Results From the Registry of the Canadian Interventional Radiology Association", Journal of Vascular and Interventional Radiology, 2001, 12:1053-1058.

Millward, S.F. et al., "LGM (Vena Tech), Vena Caval Filter: Clinical Experience in 64 Patients", Journal of Vascular and Interventional Radiology, Nov. 1991, 2:429-433.

Millward, S.F. et al., "LGM (Vena Tech), Vena Caval Filter: Experience at a Single Institution", Journal of Vascular and Interventional Radiology, Mar.-Apr. 1994, 5:351-356.

Millward, S.F. et al., "Reporting Standards for Inferior Venal Caval Filter Placement and Patient Follow-Up: Supplement for Temporary and Retrievable/Optional Filters", Journal of Vascular and Interventional Radiology, Apr. 2005, 16:441-443.

Millward, S.F., "Gunther Tulip Retrievable Filter" Why, When and How?, JACR, Jun. 2001, vol. 52, No. 3, pp. 188-192.

Millward, S.F., "Temporary and Retrievable Inferior Vena Cava Filters" Current Status, Journal of Vascular and Interventional Radiology, May-Jun. 1998, vol. 9, No. 3, pp. 381-387.

Mobin-Uddin, K. et al., "Evolution of a New Device for the Prevention of Pulmonary Embolism", The American Journal of Surgery, vol. 168, Oct. 1994, pp. 330-334.

Mohan, C.R. et al., "Comparative Efficacy and Complications of Vena Caval Filters", Journal of Vascular Surgery, 1995, 21:235-236.

Montessuit, M. et al., "Screening for Patent Foramen Ovale and Prevention of Paradoxical Embolus", Ann Fasc Surg, 1997, 11:168-172.

Montgomery, K.D. et al., The Detection and Management of Proximal Deep Venous Thrombosis in Patients With Acute Acetabular Fractures: A Follow-up Report:, Journal of Orthopedic Trauma, Jul. 1997, 1(5):330-336.

Mortele, K. J. et al., "The Swedish Laparoscopic Adjustable Gastric Banding for Morbid Obesity: Radiologic Findings in 218 Patients", American Journal of Roentgenology, 2001, 177:77-84.

Munir, M.A. et al., "An In Situ Technique to Retrieve an Entrapped J-Tip Guidewire From an Inferior Vena Cava Filter", Anesth Analo, 2002, 95:308-309.

Murakami, M. et al., "Deep Venous Thrombosis Prophylaxis in Trauma: Improved Compliance With a Novel Miniaturized Pneumatic Compression Device", Journal of Vascular Surgery, 2003, 38:923-927.

Nakagawa, N. et al., "A Retrievable Nitinol Vena Cava Filter: Experimental and Initial Clinical Results", Journal of Vascular and Interventional Radiology, 1994, 5:507-512.

Nakajima, Osamu et al., "Massive Deep Vein Thrombosis After Cesarean Section Treated With a Temporary Inferior Vena Cava Filter: A Case Report", J Cardioi 2000; 36(5): pp. 337-342.

Napolitano, L. M. et al., "Asymptomatic Deep Venous Thrombosis in the Trauma Patient: Is an Aggressive Screening Protocol Justified?", The Journal of Trauma: Injury, Infection, and Critical Care, 1997, vol. 39, No. 4, pp. 651-659.

Nazario, R. et al., "Treatment of Venous Thromboembolism", Cardiology in Review, 2002, 10(4):249-259.

Neeman, Z. et al., "Metastatic Involvement of a Retrieved Inferior Vena Cava Filter", (Clinical Center) and National Cancer Institute, National Institutes of Health, Bethesda, MD), p. 1585.

Neill, A. M. et al., "Retrievable Inferior Vena Caval Filter for Thromboembolic Disease in Pregnancy", British Journal of Obstetrics and Gynaecology, Dec. 1997, vol. 104, pp. 1416-1418.

Hammond, F.M. et al., "Venous Thromboembolism in the Patient With Acute Traumatic Brain Injury: Screening, Diagnosis, Prophylaxis, and Treatment Issues", Journal of Head Trauma Rehabilitation, Feb. 1998, vol. 13, No. 1, pp. 36-48.

Hansen, James, "Metals that Remember", Science 81, vol. 2, No. 5, pp. 44-47, Jun. 1981.

Hardhammar, P.A. et al., "Reduction in Thrombotic Events With Heparin-Coated Palmaz-Schatz Stents in Normal Porcine Coronary Arteries", Circulation, Feb. 1, 1996, vol. 93, No. 3, pp. 423-430.

Harold, K.L. et al., "Laparoscopic Approach to Open Gastric Bypass", The American Journal of Surgery, 2002, 184:61-62.

Harries, S.R., "Long-Term Follow-Up of the Antheor Inferior Vena Cava Filter", Clinical Radiology, 1998, 53:350-352.

Harris, E.J. Jr. et al., "Phlegmasia Complicating Prophylactic Percutaneous Inferior Vena Caval Interruption: A Word of Caution", Journal of Vascular Surgery, 1995, vol. 22, No. 5, pp. 606-611.

Hastings, G.S. et al., "Repositioning the 12-F Over-the-Wire Greenfield Filter", Journal of Vascular and Interventional Radiology, 2000, 11:1207-1210.

Hawkins, S.P. et al., "The Simon Nitinol Inferior Vena Cava Filter: Preliminary Experience in the UK", Clinical Radiology, 1992, 46:378-380.

Headrick, J.R. et al., "The Role of Ultrasonography and Inferior Vena Cava Filter Placement in High-Risk Trauma Patients", American Surgeon, Jan. 1997, vol. 63, Issue 1.

Helfet, D., Magnetic Resonance Venography to Evaluate Deep Venous Thrombosis in Patients With Pelvic and Acetabular Trauma, The Journal of Trauma: Injury, Infection, and Critical Care, Jul. 2001, p. 178.

Heng, J.T. et al., "Occlusion of Persistent Left Superior Vena Cava to Unroofed Coronary Sinus Using Vena Cava Filter and Coils", HEARS, Jun. 1997, vol. 77, No. 6, pp. 579-580.

Henkle, G. et al., "Patterns of Referral for Inferior Vena Caval Filtration: Delays and Their Impact", American Journal of Roentgenology, Oct. 2004, 183:1021-1024.

Hicks, M.E. et al., "Prospective Anatomic Study of the Inferior Vena Cava and Renal Veins: Comparison of Selective Renal Venography With Cavography and Relevance in Filter Placement", Journal of Vascular and Interventional Radiology, 1995, 6:721-729.

Higa, K.D. et al., "Laparoscopic Roux-en-Y Gastric Bypass for Morbid Obesity", Archives of Surgery, Sep. 2000, vol. 135, No. 9, pp. 1029-1034.

Hill, S.L. et al., "Deep Venous Thrombosis in the Trauma Patient", The American Surgeon, Jun. 1994, vol. 60, pp. 405-408.

Hingorani, A. et al., "Upper Extremity Deep Venous Thrombosis and Its Impact on Morbidity and Mortality Rates in a Hospital-Based Population", Journal of Vascular Surgery, Nov. 1997, 26:853-860.

Hirsch, D. R. et al., "Prevalence of Deep Venous Thrombosis Among Patients in Medical Intensive Care", JAMA, Jul. 26, 1995, 274(4):335337.

(56) References Cited

OTHER PUBLICATIONS

Hirsch, S. B. et al., Case Reports: Accidental Placement of the Greenfield Filter in the Heart: Report of Two Cases et al., Journal of Vascular Surgery, Dec. 1987, vol. 6, No. 6.

Hoff, W. S. et al., "Early Experience With Retrievable Inferior Vena Cava Filters in High-Risk Trauma Patients", Journal of the American College of Surgeons, Dec. 2004, vol. 199, No. 6, pp. 869-874.

Holtzman, R.B. et al., "Comparison of Carbon Dioxide and Iodinated Contrast for Cavography Prior to Inferior Vena Cava Filter Placement", The American Journal of Surgery, 2003, 185:364-368.

Hosaka, J. et al., "Placement of a Spring Filter During Interventional Treatment of Deep Venous Thrombosis to Reduce the Risk of Pulmonary Embolism", Acta Radiologica, 1999, 40:545-551.

Hughes, G.C. et al., "The Use of a Temporary Vena Caval Interruption Device in High-Risk Trauma Patients Unable to Receive Standard Venous Thromboembolism Prophylaxis", Investigative Radiology, Feb. 1999, vol. 46, No. 2, pp. 246-249.

Hunter, D.W. et al., "Retrieving the Amplatz Retrievable Vena Cava Filter", Cardiovascular and Interventional Radiology, 1987, 10:32-36.

Hyers, T. M. et al., "Antithrombotic Therapy for Venous Thromboembolic Disease", Chest, Jan. 2001, 119 (1):176S-193S.

Ihnat, D. M. et al., "Treatment of Patients With Venous Thromboembolism and Malignant Disease: Should Vena Cava Filter Placement Be Routine?", Journal of Vascular Surgery, Nov. 1998, vol. 28, No. 8, pp. 800-807.

Inge, T. H. et al., "Bariatric Surgery for Severely Overweight Adolescents: Concerns and Recommendations", Pediatrics, Jul. 2004, vol. 114, No. 1, pp. 217-223.

Izutani, H. et al., "Migration of an Inferior Vena Cava Filter to the Right Ventricle and Literature Review", Can J Cardiol, Feb. 2004, vol. 20, No. 2, pp. 233-235.

Jackson Slappy, A.L. et al., "Delayed Transcaval Renal Penetration of a Greenfield Filter Presenting as Symptomatic Hydronephrosis", The Journal of Urology, Apr. 2002, vol. 167, pp. 1778-1779.

Jacobs, D. G. et al., "The Role of Vena Caval Filters in the Management of Venous Thromboembolism" The American Surgeon, Aug. 2003, vol. 69, No. 8, pp. 635-642.

Jacobs, D. G. et al., Letters to the Editor, The Journal of Trauma, Dec. 1997, vol. 43, No. 6, pp. 988-989.

Jaeger, H.J. et al., "A Physiologic In Vitro Model of the Inferior Vena Cava With a Computer-Controlled Flow System for Testing of Inferior Vena Cava Filters", Investigative Radiology, Sep. 1997, vol. 32, No. 9, pp. 511-522.

Jain, V. et al., "Preoperative Vena Caval Interruption for Venous Thrombosis Associated With Ovarian Malignancy", Acta Obstetricia et Gynecologica Scandinavica.

James Kevin V. et al., "Tricuspid Insufficiency After Intracardiac Migration of a Greenfield Filter: Case Report and Review of the Literature", Journal of Vascular Surgery, Sep. 1996, vol. 24, No. 3, pp. 494-498.

Jarrett B.P. et al., Inferior Vena Cava Filters in Malignant Disease, Journal of Vascular Surgery, 2002, 36:704-707.

Joels, C. S. et al., "Complications of Inferior Vena Cava Filters", The American Surgeon, Aug. 2003, vol. 69, No. 8, pp. 654-659.

Johnson, M.S., "Current Strategies for the Diagnosis of Pulmonary Embolus", Journal of Vascular and Interventional Radiology, 2002, 13:13-23.

Johnson, S.P. et al., "Single Institution Prospective Evaluation of the Over-The-Wire Greenfield Vena Caval Filter", Journal of Vascular and Interventional Radiology, 1998, 9:766-773.

Jones, A.L. et al., "Case Report: Use of an IVC Filter in the Management of IVC Thrombosis Occurring as a Complication of Acute Pancreatitis", Clinical Radiology, 1998, 53:462-464.

Joshi, A. et al., "Filter-Related, Thrombotic Occlusion of the Inferior Vena Cava Treated With a Gianturco Stent", Journal of Vascular and Interventional Radiology, 2003, 14:381-385.

JP 2008-543433 filed May 30, 2008 Office Action dated Jan. 11, 2012

Kaplan, S. et al., "Surgical Management of Renal Cell Carcinoma With Inferior Vena Cava Tumor Thrombus", The American Journal of Surgery, 2002, 183:292-299.

Karmy-Jones, R. et al., "Surgical Management of Cardiac Arrest Caused by Massive Pulmonary Embolism in Trauma Patients", The Journal of Trauma: Injury, Infection, and Critical Care, 2000, vol. 48, No. 3, pp. 519-520.

Kasirajan, K. et al., "Percutaneous AngioJet Thrombectomy in the Management of Extensive Deep Venous Thrombosis", Journal of Vascular and Interventional Radiology, 2001, 12:179-185.

Katsamouris, A.A. et al., "Inferior Vena Cava Filters: In Vitro Comparison of Clot Trapping and Flow Dynamics", Radiology, 1988, 166:361-366.

Kaufman, J.A. et al., "Guide-Wire Entrapment by Inferior Vena Caval Filters: In Vitro Evaluation", Radiology, 1996, 198:71-76.

Kaufman, J.A. et al., "Operator Errors During Percutaneous Placement of Vena Cava Filters", American Journal of Roentgenology, Nov. 1995, 165:1281-1287.

Kaufman, John A., "Re: Metastatic Involvement of a Retrieved Inferior Vena Cava Filter", Journal of Vascular and Interventional Radiology, Jul. 2004, vol. 15, No. 7, pp. 775-776.

Kaw, L.L., Jr. et al., "Use of Vena Cava Filters", Techniques in Orthopaedics, 2004, 19(4):327-336.

Kazmers, A. et al., "Duplex Examination of the Inferior Vena Cava", The American Surgeon, Oct. 2000, vol. 66, pp. 986-989.

Kazmers, A. et al., "Intraoperative Insertion of Greenfield Filters: Lessons Learned in a Personal Series of 152 Cases", The American Surgeon, Oct. 2002, vol. 68, pp. 877-882.

Wittenberg, G. et al., "Long-Term Results of Vena Cava Filters: Experiences With the LGM and the Titanium Greenfield Devices", Cardiovascular and Interventional Radiology, 1998, 21:225-229.

Wittich, G. R. et al., "Anchoring a Migrating Inferior Vena Cava Stent With Use of a T-Fastener", Journal of Vascular and Interventional Radiology, 2001, 12:994-996.

Wojcik, R. et al., "Long-Term Follow-Up of Trauma Patients With a Vena Caval Filter", The Journal of Trauma: Injury, Infection, and Critical Care, Nov. 2000, 49(5):839-843.

Wojtowycz, M. M. et al., "The Bird's Nest Inferior Vena Caval Filter: Review of a Single-Center Experience", Journal of Vascular and Interventional Radiology, 1997, 8:171-179.

Woodward, E. B. et al., "Delayed Retroperitoneal Arterial Hemorrhage After Inferior Vena Cava (IVC) Filter Insertion: Case Report and Literature Review of Caval Perforations by IVC Filters", Annals of Vascular Surgery, 2002, 16:193-196.

Xian, Z. Y. et al., "Multiple Emboli and Filter Function: An in Vitro Comparison of Three Vena Cava Filters", Journal of Vascular and Interventional Radiology, 1995, 6:887-893.

Xu, X.Y. et al., "Flow Studies in Canine Artery Bifurcations Using a Numerical Simulation Method", Journal of Biochemical Engineering, Nov. 1992, 114:504-511.

Yagi, A. et al., "Pulmonary Thromboembolism Evaluating the Indication and Effect of a Vena Caval Filter With Indium-111-Platelet Scintigraphy", Circulation Journal, Jun. 2004, 68:599-601.

Yavuz, Kivilcim et al., "Retrievable of a Malpositioned Vena Cava Filter With Embolic Protection With Use of a Second Filter", Journal of Vascular Interventional Radiology, 2005, 16:531-534.

Yonezawa, K. et al., "Effectiveness of an Inferior Vena Cava Filter as a Preventive Measure Against Pulmonary Thromboembolism After Abdominal Surgery", Surgery Today, 1999, 29:821-824.

Yucel, E. Kent, "Pulmonary MR Angiography: Is It Ready Now?", Radiology, 1999, 210:301-303.

Zamora, C. A. et al., "Prophylactic Stenting of the Inferior Vena Cava Before Transcatheter Embolization of Renal Cell Carcinomas: An Alternative to Filter Placement", Journal of Endovascular Therapy, 2004, 11:84-88.

Zanchetta, M. et al., "A New Permanent and Retrievable Vena Cava Filter: Its Removal After Five Months", Italian Heart Journal, Sep. 2001, 2(9):715-716.

Zeni, P. T. et al., "Use of Rheolytic Thrombectomy in Treatment of Acute Massive Pulmonary Embolism", Journal of Vascular and Interventional Radiology, 2003, 14:1511-1515.

(56) References Cited

OTHER PUBLICATIONS

Zinzindohoue, F. et al., "Laparoscopic Gastric Banding: A Minimally Invasive Surgical Treatment for Morbid Obesity—Prospective Study of 500 Consecutive Patients", Annals of Surgery, 2003, 237(1):1-9.
Zwaan et al., "Clinical Experience with Temporary Vena Cava Filters" JVIR 9:594-601 (1998).
Rose, S. C. et al., "Regarding "Bedside Vena Cava Filter Placement Guided With Intravascular Ultrasound"", Journal of Vascular Surgery, Apr. 2002, vol. 35, No. 4.
Rossi, G. et al., "Open to Critique: An Unusual Complication of Vena Cava Filter Placement", Journal of Vascular Surgery, Nov. 1996, vol. 24, No. 5.
Rousseau, Hervé et al., "The 6-F Nitinol TrapEase Inferior Vena Cava Filter: Results of a Prospective Multicenter Trial", J Vasc Interv Radiol, 2001,12:299-304.
Rubin, B. G. et al., "Care of Patients With Deep Venous Thrombosis in an Academic Medical Center: Limitations and Lessons", Journal of Vascular Surgery, 1994, 20:698-704.
Ruiz, A. J. et al., "Heparin, Deep Venous Thrombosis, and Trauma Patients", The American Journal of Surgery, Aug. 1991, 162:159-162.
Ryskamp, R. P. et al., "Utilization of Venous Thromboembolism Prophylaxis in a Medical-Surgical ICU", Chest, Jan. 1998, 113(1):162-164.
S. Raghavan et al., "Migration of Inferior Vena Cava Filter Into Renal Hilum", Nephron, Jun. 2002; 91, 2; Health & Medical Complete; pp. 333-335.
Salamipour et al., "Percutaneous Transfemoral Retrieval of a Partially Deployed Simon-Nitinol Filter Misplaced into the Ascending Lumbar Vein" JVIR 7:917-919 (1996).
Salamipour, H. et al., "Percutaneous Transfemoral Retrieval of a Partially Deployed Simon-Nitinol Filter Misplaced Into the Ascending Lumbar Vein", Journal of Vascular and Interventional Radiology, 1996, 7:917-919.
Sapala, J. A. et al., "Fatal Pulmonary Embolism After Bariatric Operations for Morbid Obesity: A 24-Year Retrospective Analysis", Obesity Surgery, 2003, 13:819-825.
Sarasin, F. P. et al., "Management and Prevention of Thromboemboli in Patients With Cancer-Related Hypercoagulable", Journal of General Internal Medicine, Sep. 1993, 8:476-485.
Savader, Scott J., Venous Interventional Radiology with Clinical Perspectives, Chapter 28: Inferior Vena Cava Filters, pp. 367-399, Apr. 2000.
Savin, M. A. et al., "Greenfield Filter Fixation in Large Vena Cavae", Journal of Vascular and Interventional Radiology, 1998, 9:75-80.
Savin, Michael A. et al., "Placement of Vena Cava Filters: Factors Affecting Technical Success and Immediate Complications", AJR, Sep. 2002, Vo. 179, pp. 597-602.
Schanzer, H. et al., "Guidewire Entrapment During Deployment of the Over-the-Guidewire Stainless Steel Greenfield Filter: A Device Design-Related Complication", Journal of Vascular Surgery, 2000, 31:607-610.
Schleich, J.-M. et al., "Long-Term Follow-up of Percutaneous Vena Cava Filters: A Prospective Study in 100 Consecutive Patients", Eur J Vasc Endovasc Surg, 2001, vol. 21, pp. 450-457.
Schultz, D. J. et al., "Incidence of Asymptomatic Pulmonary Embolism in Moderately to Severely Injured Trauma Patients", Journal of Trauma: Injury, Infection, and Critical Care, 2004, 56:727-733.
Sequeira et al., "A Safe Technique for Introduction of the Kimray-Greenfield Filter" Radiology 133:799-800 (Dec. 1979).
Shackford, S. R. et al., "Venous Thromboembolism in Patients With Major Trauma", The American Journal of Surgery, Apr. 1990, vol. 1 59, pp. 365-369.
Shaer, J. et al., "An Unusual Cause of Low Back Pain?: A Case Report", Spine, Jun. 15, 1998, 23(12):1349-1350.
Shahmanesh, Maryam et al., "Inferior Vena Cava Filters for HIV Infected Patients With Pulmonary Embolism and Contraindications to Anticoagulation", Sex Transm INF, 2000, 76:395-397.
Sharafuddin, M. J. et al., "Endovascular Management of Venous Thrombotic and Occlusive Diseases of the Lower Extremities", Journal of Vascular and Interventional Radiology, Apr. 2003, 14:405-423.
Sharpe, R. P. et al., "Incidence and Natural History of Below-Knee Deep Venous Thrombosis in High-Risk Trauma Patients", The Journal of Trauma: Injury, Infection, and Critical Care, Dec. 2002, 53:1048-1052.
Sheikh, M. A. et al., "Images in Vascular Medicine", Vascular Medicine 2001, 6:63-64.
Sheikh, M. A. et al., "Isolated Internal Jugular Vein Thrombosis: Risk Factors and Natural History", Vascular Medicine, 2002, 7:177-179.
Shellock, F. G. et al., "MR Procedures: Biologic Effects, Safety, and Patient Care", Radiology, 2004, 232:635-652.
Siddique, R. M. et al., "Thirty-Day Case-Fatality Rates for Pulmonary Embolism in the Elderly", Archives of Internal Medicine, Nov. 11, 1996, 156:2343-2347.
Siegel and Robertson, "Percutaneous Tranfemoral Retrieval of a Free-Floating Titanium Greenfield Filter with an Amplatz Goose Neck Snare" JVIR 4:565-568 (1993).
Simon et al., "Transvenous Devices for the Management of Pulmonary Embolism", CardioVascular and Interventional Radiology, 3:308-313, 1980, pp. 112-120.
Simon Nitinol Filter SNF/SL Filter Sets, C. R. Bard, Inc. PK5014851 Rev. 01 09/02 (2002).
Simon Nitinol Filter, Nitinol Medical Technologies, Inc., p. 290.
Simon, M. et al., "Comparative Evaluation of Clinically Available Inferior Vena Cava Filters With an In Vitro Physiologic Simulation of the Vena Cava", Radiology, 1993, 189:769-774.
Simon, M. et al., "Paddle-Wheel CT Display of Pulmonary Arteries and Other Lung Structures: A New Imaging Approach", American Journal of Roentgenology, Jul. 2001, pp. 195-198.
Simon, M., "Vena Cava Filters: Prevalent Misconceptions", Journal of Vascular and Interventional Radiology, 1999, 10:1021-1024.
Simon, Morris et al., "Simon Nitinol Inferior Vena Cava Filter: Initial Clinical Experience", Radiology, vol. 172, No. 1, DO 99-103, Jul. 1989.
Simon,M. et al., "A Vena Cava Filter Using Thermal Shape Memory Alloy", Radiology, Oct. 1977, 125:89-94.
Sing, R. F. et al., "Bedside Carbon Dioxide (CO2) Preinsertion Cavagram for Inferior Vena Cava Filter Placement: Case Report", Journal of Trauma, Dec. 1999, 47(6):1140-1142.
Sing, R. F. et al., "Bedside Carbon Dioxide Cavagrams for Inferior Vena Cava Filters: Preliminary Results", Journal of Vascular Surgery, 2000, 32:144-147.
Sing, R. F. et al., "Bedside Insertion of Inferior Vena Cava Filters in the Intensive Care Unit", Journal of American College of Surgeons, May 2001, 192(5):570-575.
Sing, R. F. et al., "Bedside Insertion of Inferior Vena Cava Filters in the Intensive Care Unit", Journal of Trauma, Dec. 1999, 47(6):1104-1109.
Sing, R. F. et al., "Bedside Insertion of the Inferior Vena Cava Filter in the Intensive Care Unit", The American Surgeon, Aug. 2003, 69:660-662.
Sing, R. F. et al., "Guidewire Incidents With Inferior Vena Cava Filters", JAOA, Apr. 2001, 101(4):231-233.
Sing, R. F. et al., "Preliminary Results of Bedside Inferior Vena Cava Filter Placement", Chest, Jul. 1998, 114(1):315.
Sing, R. F. et al., "Regarding "Bedside Vena Cava Filter Placement Guided With Intravascular Ultrasound, Journal of Vascular Surgery, May 2002, vol. 25, No. 5.
Sing, Ronald F., "Safety and Accuracy of Bedside Carbon Dioxide Cavography for Insertion of Inferior Vena Cava Filters in the Intensive Care Unit", American College of Surgeons, Feb. 2, 2001, vol. 192, pp. 168-171.
Smith, T. P. et al., "Acute Pulmonary Thromboembolism-Comparison of the Diagnostic Capabilities of Convention Film-Screen and Digital Angiography", Chest, 2002, 122:968-972.
Smith, T. P., "Pulmonary embolism: What's Wrong With This Diagnosis", American Journal of Roentgenology, Jun. 2000, 174:1489-1498.
Spain, D. A. et al., "Venous Thromboembolism in the High-Risk Trauma Patient: Do Risks Justify Aggressive Screening and Prophy-

(56) References Cited

OTHER PUBLICATIONS laxis?", The Journal of Trauma: Injury, Infection, and Critical Care, 1997, vol. 42, No. 3, pp. 463-469.
Spence, Liam D. et al., "Acute Upper Extremity Deep Venous Thrombosis, Safety and Effectiveness of Superior Vena Caval Filters", Radiology, Jan. 1999, vol. 210, DO 53-58.
Stavropoulos, S. W. et al., "In Vitro Study of Guide Wire Entrapment in Currently Available Inferior Vena Cava Filters", Journal of Vascular and Interventional Radiology, 2003, 14:905-910.
Dabbagh, A. et al., "Late Complication of a Greenfield Filter Associating Caudal Migration and Perforation of the Abdominal Aorta by a Ruptured Strut", Journal of Vascular Surgery, Aug. 1995, vol. 22, No. 2, pp. 182-187.
Dake, M.D. et al., "Thrombolytic Therapy in Venous Occlusive Disease", Journal of Vascular and Interventional Radiology, 1995, 6:73S-77S.
Dalman, R. et al., "Cerebrovascular Accident After Greenfield Filter Placement for Paradoxical Embolism", Journal of Vascular Surgery, Mar. 1989, vol. 9, No. 3, pp. 452-454.
Danetz, J. S. et al., "Selective Venography Versus Nonselective Venography Before Vena Cava Filter Placement: Evidence for More, Not Less", Journal of Vascular Surgery, Nov. 2003, Vo. 38, No. 5, pp. 928-934.
Danikas, Dimitrios et al., "Use of a Fogarty Catheter to Open an Incompletely Expanded Vena Tech-LGM Vena Cava Filter", Angiology, Apr. 2001, vol. 52, No. 4, pp. 283-286.
Darcy, M.D. et al., "Short-Term Prophylaxis of Pulmonary Embolism by Using a Retrievable Vena Cava Filter", American Journal of Roentgenology, 1986, 147:836-838.
Dardik, Alan et al., "Vena Cava Filter Ensnarement and Delayed Migration: An Unusual Series of Cases", Journal of Vascular Surgery, Nov. 1997, vol. 26, No. 5.
David, W. et al., "Pulmonary Embolus After Vena Cava Filter Placement", The American Surgeon, Apr. 1999, vol. 65, pp. 341-346.
Davidson, B.L., "DVT Treatment in 2000: State of the Art", Orthopedics, Jun. 2000, 23(6):pp. S651-S654.
Davison, Brian D. et al., "TrapEase Inferior Vena Cava Filter Placed Via the Basilic Arm Vein: A New Antecubital Access", J Vasc Interv Radioi, Jan. 2002, 13:107-109.
de Godoy, José Maria Pereira et al., "In-Vitro Evaluation of a New Inferior Vena Cava Filter—The Stent-Filter", Vascular and Endovascular Surgery, Nov. 3, 2004, vol. 38, pp. 225-228.
de Gregorio, M.A. "Inferior Vena Cava Filter Update", Arch Bronconeumol, 2004, vol. 40, No. 5, pp. 193-195.
De Gregorio, M.A. et al., "Animal Experience in the Gunther Tulip Retrievable Inferior Vena Cava Filter", Cardiovascular and Interventional Radiology, Nov. 2001, 24:413-417.
De Gregorio, M.A. et al., "Mechanical and Enzymatic Thrombolysis for Massive Pulmonary Embolism", Journal of Vascular and Interventional Radiology, 2002, 13:163-169.
de Gregorio, Miguel Angel et al., "The Gunther Tulip Retrievable Filter: Prolonged Temporary Filtration by Repositioning Within the Inferior Vena Cava", J Vasc Interv Radioi, Oct. 2003, 14:1259-1265.
De Gregorio, Miguel Angel et al., "Retrievability of Uncoated Versus Paclitaxel-Coated Gunther-Tulip IVC Filters in an Animal Model", J Vasc Interv Radio, Jul. 2004,15:719-726.
Debing, E. et al., "Popliteal Venous Aneurysm With Pulmonary Embolism", Journal of Cardiovascular Surgery, Oct. 1998, vol. 39, No. 5, pp. 569-572.
Decousus, H. et al., "A Clinical Trial of Vena Caval Filters in the Prevention of Pulmonary Embolism in Patients With Proximal Deep-Vein Thrombosis", The New England Journal of Medicine, Feb. 12, 1998, vol. 338, No. 7, pp. 409-415.
DeMaria, E.J. et al., "Results of 281 Consecutive Total Laparoscopic Roux-en-Y Gastric Bypasses to Treat Morbid Obesity", Annals of Surgery, 2002, vol. 235, No. 5 pp. 640-647.
Dennis, J. W. et al., "Efficacy of Deep Venous Thrombosis Prophylaxis in Trauma Patients and Identification of High-Risk Groups",The Journal of Trauma, 1993, vol. 35, No. 1, pp. 132-137.

Denny, D.F. Jr., "Errant Percutaneous Greenfield Filter Placement Into the Retroperitoneum" Journal of Vascular Surgery Jun. 1991, vol. 13, No. 6.
Dewald, C.L. et al., Vena Cavography With CO2 Versus With Iodinated Contrast Material for Inferior Vena Cava Filter Placement: A Prospective Evaluation, Radiology, 2000, 216:752-757.
Dibie, A. et al., "In Vivo Evaluation of a Retrievable Vena Cava Filter—The Dibie-Musset Filter: Experimental Results", Cardiovascular and Interventional Radiology, 1998, 21:151-157.
Dick, A. et al., "Declotting of Embolized Temporary Vena Cava Filter by Ultrasound and the Angiojet: Comparative Experimental In Vitro Studies", Investigative Radiology, Feb. 1998, vol. 33(2), pp. 91-97.
Doherty, C., "Special Problems of Massive Obesity", Primary Care Physician'S Resource Center, file:// D:\Special%20Problems%20of%20Massive%20Obesity.htm, retrieved Jul. 26, 2005.
Dotter et al., "Transluminal Expandable Nitinol Coil Stent Grafting: Preliminary Report" Radiology 147:259-260 (Apr. 1983).
Duperier, T. et al., "Acute Complications Associated With Greenfield Filter Insertion i High-Risk Trauma Patients", The Journal of Trauma: Injury, Infection, and Critical Care, Mar. 2003, vol. 54, No. 3, pp. 545-549.
Ebaugh, James L. et al., "Bedside Vena Cava Filter Placement Guided With Intravascular Ultrasound", Journal of Vascular Surgery, Jul. 2001,34:21-26.
Edlow, J.A., "Emergency Department Management of Pulmonary Embolism", Emergency Medicine Clinics of North America, Nov. 2001, vol. 19, No. 4, pp. 995-1011.
Egermayer, P., "Follow-Up for Death or Recurrence Is Not a Reliable Way of Assessing the Accuracy of Diagnostic Tests for Thromboembolic Disease", Chest 1997, 111:1410-1413.
Ekim, N. et al., "Pulmonary Thromboembolism With Massive Vaginal Bleeding Due to Thrombolytic Therapy", Respirology, 2003, 8:246-248.
Engmann, E. et al., "Clinical Experience With the Antecubital Simon Nitinol IVC Filter", Journal of Vascular and Interventional Radiology, 1998, 9:774-778.
EP 99951426 European Search Report dated Mar. 18, 2003.
Epstein et al., "Experience with the Amplatz Retrievable Vena Cava Filter" Radiology 175:105-110 (1989).
Fava, M. et al., "Massive Pulmonary Embolism: Percutaneous Mechanical Thrombectomy During Cardiopulmonary Resuscitation", Journal of Vascular and Intervention Radiology, 2005, 16:119-123.
Fava, M. et al., "Massive Pulmonary Embolism: Treatment With the Hydrolyser Thrombectomy Catheter", Journal of Vascular and Intervention Radiology, 2000, 11:1159-1164.
Feezor, R.J. et al., "Duodenal Perforation With an Inferior Vena Cava Filter: An Unusual Cause of Abdominal Pain", Journal of Vascular Surgery, 2002, pp. 1-3.
Fernandez, A.Z. Jr. et al., "Multivariate Analysis of Risk Factors for Death Following Gastric Bypass for Treatment of Morbid Obesity", Annals of Surgery, May 2004, vol. 239, No. 5, pp. 698-703.
Ferral, H., "Regarding "Lessons Learned From a 6-Year Clinical Experience With Superior Vena Cava Greenfield Filters"", Journal of Vascular Surgery, Apr. 2001, vol. 33, No. 4.
Ferraro, F. et al., "Thromboembolism in Pregnancy: A New Temporary Caval Filter", Miverva Anestesiologica, 2001, vol. 67, No. 5, pp. 381-385.
Ferris, E.J. et al., "Percutaneous Inferior Vena Caval Filters: Follow-Up of Seven Designs in 320 Patients", Radiology 1993, 188:851-856.
Fink, S. et al., "Pulmonary Embolism and Malpractice Claims", Southern Medical Journal, Dec. 1998, vol. 91, No. 12, pp. 1149-1152.
Fobbe, Franz et al., "Gunther Vena Caval Filter: Results of Long-Term Follow-Up", AJR, Nov. 1988,151:1031-1034.
Foley, M. et al., "Pulmonary Embolism After Hip or Knee Replacement: Postoperative Changes on Pulmonary Scintigrams in Asymptomatic Patients", Radiology, 1989, 172:481-485.
Fraser, J.D. et al., "Deep Venous Thrombosis: Recent Advances and Optimal Investigation With US", Radiology, 1999, 211:9-24.

(56) References Cited

OTHER PUBLICATIONS

Frezza, E.E. et al., "Entrapment of a Swan Ganz Catheter in an IVC Filter Requiring Caval Exploration", Journal of Cardiovascular Surgery, 1999, 40:905-908.
Friedell, M.L. et al., "Case Report: Migration of a Greenfield Filter to the Pulmonary Artery: Case Report", Journal of Vascular Surgery, Jun. 1986, vol. 3, No. 6, pp. 929-931.
Friedland, M. et al., "Vena Cava Duplex Imaging Before Caval Interruption", Journal of Vascular Surgery, Oct. 1995, vol. 24, No. 4, pp. 608-613.
Gabelmann, A. et al., "Percutaneous Retrieval of Lost of Misplaced Intravascular Objects", American Journal of Radiology, Jun. 2001, 176:1509-1513.
Galus, Maria et al., "Indications for inferior vena cava filters," Internal Medicine, Aug. 11, 1997; 157, 15; Health and Medical Complete, pp. 1770-1771.
Bovyn, G. et al., "The Tempofilter®: A Multicenter Study of a New Temporary Caval Filter Implantable for up to Six Weeks", Annals of Vascular Surgery, 1997, 11:520-528.
Bracale, G. et al., "Spontaneous Rupture of the Iliac Vein", The Journal of Cardiovascular Surgery, 1999, 40:871-875.
Brasel, K.J. et al., "Cost-Effective Prevention of Pulmonary Embolus in High-Risk Trauma Patients", The Journal of Trauma: Injury, Infection, and Critical Care, Mar. 1997, vol. 42, No. 3, pp. 456-462.
Bravo, S. M. et al., "Percutaneous Venous Interventions", Vascular Medicine, 1998, 3:61-66.
Bridges, G.G. et al., "Expedited Discharge in Trauma Patients Requiring Anticoagulation for Deep Venous Thrombosis Prophylaxis: The LEAP Program", The Journal of Trauma: Injury, Infection and Critical Care, Feb. 2003, vol. 54, No. 2, pp. 232-235.
Brolin, R.E., "Laparoscopic Verses Open Gastric Bypass to Treat Morbid Obesity", Annals of Surgery, Apr. 2004, vol. 239, No. 4, pp. 438-440.
Brountzos, E N. et al., "A New Optional Vena Cava Filter: Retrieval at 12 Weeks in an Animal Model", Journal of Vascular and Interventional Radiology, Jun. 2003, 14:763-772.
Brown, D. R. et al., "Gadolinium, Carbon Dioxide, and Iodinated Contrast Material for Planning Inferior Vena Cava Filter Placement: A Prospective Trial", Journal of Vascular and Interventional Radiology, Aug. 2003, 14:1017-1022.
Browne, R. J. et al., "Guidewire Entrapment During Greenfield Filter Deployment", Journal of Vascular Surgery, Jan. 1998, 27:174-176.
Bruckheimer, E. et al., "In Vitro Evaluation of a Retrievable Low-Profile Nitinol Vena Cava Filter", Journal of Vascular and Interventional Radiology, Apr. 2003, 14:469-474.
Bucker, A. et al., "Real-Time MR Guidance for Inferior Vena Cava Filter Placement in an Animal Model", Journal of Vascular and Interventional Radiology, Jun. 2001, 12:753-756.
Buerger, P.M. et al., "Risk of Pulmonary Emboli in Patients With Pelvic Fractures", The American Surgeon, Aug. 1993, vol. 59, pp. 505-508.
Burbridge, B. E. et al., "Incorporation of the Gunther Temporary Inferior Vena Cava Filter into the Caval Wall", Journal of Vascular and Interventional Radiology, Mar.-Apr. 1996, 7:289-290.
C.R. Bard Simon Nitinol Filter: For Use in the Vena Cava: Instructions for Use (1995, 1997).
CA 2648325 filed Sep. 23, 1999 Office Action dated Apr. 26, 2011.
Cahn, M. D. et al., "Long Term Follow-up of Greenfield Inferior Vena Cava Filter Placement in Children", Journal of Vascular Surgery, Nov. 2001, 34:820-825.
Cain Jr., J.E. et al., "The Morbidity of Heparin Therapy After Development of Pulmonary Embolus in Patients Undergoing Thoracolumbar or Lumbar Spinal Fusion", Spine, vol. 20, No. 14, 1995, pp. 1600-1603.
Campbell, J. J. et al., "Aortic Pseudoaneurysm From Aortic Penetration With a Bird's Nest Vena Cava Filter", Journal of Vascular Surgery, Sep. 2003, 38:596-599.
Capella, J.F. et al., An Assessment of Vertical Banded Gastroplasty-Roux-en-Y Gastric Bypass for the Treatment of Morbid Obesity.

Carabasi III, R. A. et al., "Complications Encountered With the Use of the Greenfield Filter", The American Journal of Surgery, Aug. 1987, Vo. 154, pp. 163-168.
Carlin, A. M. et al., "Prophylactic and Therapeutic Inferior Vena Cava Filters to Prevent Pulmonary Emboli in Trauma Patients", Archives of Surgery, May 2002, vol. 137, p. 521.
Carman, Teresa L. et al., Outpatient treatment of deep venous thrombosis, Chest; Nov. 1999; 116, 5; Health & Medical Complete, pp. 1492-1493.
Carter, Y. et al., "Deep Venous Thrombosis and ABO Blood Group Are Unrelated in Trauma Patients", The Journal of Trauma: Injury, Infection, and Critical Care, 2002, 52:112-116.
Castaneda, F. et al., "Catheter-Directed Thrombolysis in Deep Venous Thrombosis With Use of Reteplase: Immediate Results and Complications From a Pilot Study", Journal of Vascular and Interventional Radiology, 2002, 13:577-580.
Ceelen, W. et al., "Surgical Treatment of Severe Obesity With a Low-Pressure Adjustable Gastric Band, Experimental Data and Clinical Results in 625 Patients", Annals of Surgery, 2003, 237(1):10-16.
Chanduszko, A., "Determination of Nitinol Transition Temperatures Using a Dynamical Mechanical Analyzer", The International Conference on Shape Memory and Superelastic Technology, 2000 Conference Proceedings, 2001, pp. 375-381.
Chaturvedi, R. R. et al., "Intraoperative Apical Ventricular Septal Defect Closure Using a Modified Rashkind Double Umbrella", Heart, Oct. 1996, vol. 76, No. 4, pp. 367-369.
Chengelis, D.L. et al., "Progression of Superficial Venous Thrombosis to Deep Vein Thrombosis", Journal of Vascular Surgery, 1996, 24:745-749.
Cherian, J. et al., "Recurrent Pulmonary Embolism Despite Inferior Vena Cava Filter Placement in Patients With the Antiphospholipid Syndrome", Journal of Clinical Rheumatology, Feb. 2005, vol. 11, No. 1, pp. 56-58.
Cho, K. J. et al., "Evaluation of a New Percutaneous Stainless Steel Greenfield Filter", Journal of Vascular and Interventional Radiology, Mar.-Apr. 1997, 8:181-187.
Choban, P.S. et al., "The Impact of Obesity on Surgical Outcomes: A Review, "Journal of the American College of Surgeons, Dec. 1997, vol. 185, pp. 593-603.
Chung, J.W. et al., "Acute Iliofemoral Deep Vein Thrombosis: Evaluation of Underlying Anatomic Abnormalities by Spiral CT Venography", Journal of Vascular and Interventional Radiology, 2004, 15:249-256.
Clarke, C.S. et al., "Puerperal Ovarian Vein Thrombosis With Extension Into the Inferior Vena Cava", The American Surgeon, Feb. 1999, vol. 65, No. 2, pp. 147-150.
Conners III, M. S et al., "Duplex Scan-Directed Placement of Inferior Vena Cava Filters: A Five-year Institutional Experience", Journal of Vascular Surgery, Feb. 2002, vol. 35, No. 2, pp. 286-291.
Consensus Conference, "Prevention of Venous Thrombosis and Pulmonary Embolism", JAMA, Aug. 8, 1986, vol. 256, No. 6, pp. 744-749.
Cook "Bird's Nest" Vena Cava Filter, Cook Incorporated, a Cook Group Company, Nov. 1982.
Cook, "Gunther Tulip Vena Cava Mreye.TM. Filter" Sales Brochure (2001).
Cooper, S.G. et al., "Distal Retraction and Inversion of the Simon Nitinol Filter During Surgical Venous Procedures: Report of Two Cases", Journal of Vascular and Interventional Radiology, 1997, 8:433-435.
Cottam, D.R. et al., "Laparoscopic Era of Operations for Morbid Obesity", Archives of Surgery, Apr. 2003, 138 (4):367-375.
Couch, G. G. et al., "An In Vitro Comparison of the Hemodynamics of Two Inferior Vena Cava Filters", Journal of Vascular Surgery, Mar. 2000, 31:539-549.
Couch, G. G. et al., "In Vitro Assessment of the Hemodynamic Effects of a Partial Occlusion in a Vena Cava Filter", Journal of Vascular Surgery, Apr. 1997, vol. 25, No. 4, pp. 663-672.
Cragg et al., "Nonsurgical Placement of Arterial Endoprostheses: A New Technique Using Nitinol Wire" Radiology 147:261-263 (Apr. 1983).

(56) References Cited

OTHER PUBLICATIONS

Cragg, A. et al., "A New Percutaneous Vena Cava Filter", American Journal of Roentgenology, Sep. 1983, 141:601-604.
Criado, Enrique, Letters to the Editor, Journal of the American College of Surgeons, Mar. 1996, vol. 182, pp. 279-280.
Critical Care Medicine, vol. 32, No. 12 (Suppl.), pp. A181-A188, 2004.
Crochet, D. et al., "Evaluation of the LGM Vena-Tech Infrarenal Vena Cava Filter in an Ovine Venous Thromboembolism Model", Journal of Vascular Interventional Radiology, Jun. 2001, 12:739-745.
Crochet, D. P. et al., "Long-Term Follow-Up of Vena Tech-LGM Filter: Predictors and Frequency of Caval Occlusion", Journal of Vascular Interventional Radiology, Feb. 1999, 10:137-142.
Crochet, D. P. et al., "Vena Tech-LGM Filter: Long-Term Results of a Prospective Study", Radiology, 1993, 188:857-860.
Cvoro, V. et al., "Inferior Vena Caval Filters or Anticoagulation for Patients With Haemorrhagic Stroke Complicated by Venouse Thromboembolism?", Age and Ageing, Mar. 2002, vol. 32, No. 2, Research Library, pp. 85-86.
Cynamon et al., "Percutaneous Removal of a Titanium Greenfield Filter" AJR 159:777-778 (Oct. 1992).
Neri, E. et al., "Protected Iliofemoral Venous Thrombectomy in a Pregnant Woman With Pulmonary Embolism and Ischemic Venous Thrombosis", Texas Heart Institute Journal, 2002, vol. 29, No. 2, pp. 130-132.
Neuerburg et al., "New Retrievable Percutaneous Vena Cava Filter: Experimental In Vitro and In Vivo Evaluation" Cardiovasc. Intervent. Radiol. 16:224-229 (1993).
Neuerburg, J.M. et al., "Percutaneous Retrieval of the Tulip Vena Cava Filter: Feasibility, Short-and long-Term Changes—An Experimental Study in Dogs", Cardiovascular and Interventionai Radiology, 2001, 24:418-423.
Neuerburg, Jorg et al., "Developments in Inferior Vena Cava Filters: A European Viewpoint", Seminars in Interventional Radiology, vol. 11, No. 4, Dec. 1994, pp. 349-357.
Nguyen, N. T. et al., "A Comparison Study of Laparoscopic Versus Open Gastric Bypass for Morbid Obesity", Journal of the American College of Surgeons, Aug. 2000, vol. 191, No. 2, pp. 149-155.
Nguyen, N. T. et al., "Comparison of Pulmonary Function and Post-operative Pain After Laparoscopic Versus Open Gastric Bypass: A Randomized Trial", Journal of Americal College of Surgeons, 2001, 192:469-477.
Norwood, S. H. et al., "A Potentially Expanded Role for Enoxaparin in Preventing Venous Thromboembolism in High Risk Blunt Trauma Patients", Journal of the American College of Surgeons, 2001, 192:161-167.
Nunn, C. R. et al., "Cost-Effective Method for Bedside Insertion of Vena Caval Filters in Trauma Patients, "The Journal of Trauma, Nov. 1997, vol. 43, No. 5, pp. 752-758.
Nutting, Charles et al., "Use of a TrapEase Device as a Temporary Caval Filter", Journal of Vascular Interventional Radiology, Aug. 2001, 12:991-993.
O'Brien, P. E. et al., "Laparoscopic Adjustable Gastric Banding in the Treatment of Morbid Obesity", Archives of Surgery, Apr. 2003, 138(4):376-382.
O'Malley, K. F. et al., "Prevention of Pulmonary Embolism After Pelvic Fracture: Rational Use of Inferior Vena Caval Filters", (Cooper Hospital/University Medical Center), Jan. 1996, vol. 40.
O'Sullivan, G. J. et al., "Endovascular Management of Iliac Vein Compression (May-Thurner) Syndrome", Journal of Vascular and Interventional Radiology, 2000, 11:823-836.
Offner, P. J. et al., "The Role of Temporary Inferior Vena Cava Filters in Critically Ill Surgical Patients", Archives of Surgery, Jun. 2003, vol. 138, pp. 591-595.
Olearchyk, A. S., "Insertion of the Inferior Vena Cava Filter Followed by Iliofemoral Venous Thrombectomy for Ischemic Venous Thrombosis", Journal of Vascular Surgery, Apr. 1987, vol. 5, No. 4, pp. 645-647.
Olin, J. W., "Pulmonary Embolism", Reviews in Cardiovascular Medicine, 2002, 3(2):S68-S75.
Oppat, W. F. et al., "Intravascular Ultrasound-Guided Vena Cava Filter Placement", Journal of Endovascular Surgery, 1999, 6:285-287.
Ornstein, D. L. et al., "Cancer, Thrombosis, and Anticoagulants", Current Opinion in Pulmonary Medicine, 2000, 6:301-308.
Ortega, M. et al., "Efficacy of Anticoagulation Post-Inferior Vena Caval Filter Placement", American Surgeon, May 1998, vol. 64, Issue 5, pp. 419-423.
Ortiz-Saracho, J. et al., "An Unusual Cause of Pulmonary Artery Thrombosis", Chest, 1998, 114:309-310.
Owings, J. T. et al., "Timing of the Occurrence of Pulmonary Embolism in Trauma Patients", Archives of Surgery, Aug. 1997, 132(8):862-867.
Padberg, F. T. et al, "Hemodynamic and Clinical Improvement After Superficial Vein Ablation in Primary Combined Venous Insufficiency With Ulceration", Journal of Vascular Surgery, 1996, 24:711-718.
Pais, S. O. et al., "Percutaneous Insertion of the Greenfield Inferior Vena Cava Filter: Experience With Ninety-Six Patients", Journal of Vascular Surgery, Oct. 1988, vol. 8. No. 4.
Palastrant et al., "Comparative In Vitro Evaluation of the Nitinol Inferior Vena Cava Filter" Radiology 145:351-355 (Nov. 1982).
Palestrant, Aubrey M. et al., "Comparative In Vitro Evaluation of the Nitinollnferior Vena Cava Filter", Radiology, Nov. 1982,145:351-355.
Participants in the Vena Caval Filter Consensus Conference, "Recommended Reporting Standards for Vena Caval Filter Placement and Patient Follow-Up", Journal of Vascular and Interventional Radiology, 2003, 14:S427-S432.
Participants in the Vena Caval Filter Consensus Conference, "Recommended Reporting Standards for Vena Caval Filter Placement and Patient Follow-Up", Journal of Vascular Surgery, 1999, 30:573-579.
Partsch, H. et al., "Frequency of Pulmonary Embolism in Patients Who Have Iliofemoral Deep Vein Thrombosis and Are Treated With Once- or Twice-Daily Low-Molecular Weight Heparin", Journal of Vascular Surgery, 1996, 24:774-782.
Passman, M. A. et al., "Pulmonary Embolism is Associated With the Combination of Isolated Calf Vein Thrombosis and Respiratory Symptoms", Journal of Vascular Surgery, 1997, 25:39-45.
Patterson, R. B. et al., "Case Reports: Repositioning of Partially Dislodged Greenfield Filters From the Right Atrium by Use of a Tip Deflection Wire", Journal of Vascular Surgery, Jul. 1990, vol. 12, No. 1, pp. 70-72.
Patton, J. H. Jr., et al., "Prophylactic Greenfield Filters: Acute Complications and Long-Term Follow-Up", The Journal of Trauma: Injury, Infection, and Critical Care, 1996, vol. 41, No. 2, pp. 231-237.
Pavcnik, Dusan et al., "Retrievable IVC Square Stent Filter: Experimental Study", Cardiovascular Interventional Radiology, 1999,22:239-245.
PCT/US03/05385 filed Feb. 20, 2003 International Search Report dated Jun. 17, 2003.
PCT/US07/09215 filed Apr. 16, 2007 International Preliminary Report on Patentability dated Sep. 23, 2008.
PCT/US07/09215 filed Apr. 16, 2007 International Search Report dated Sep. 23, 2008.
PCT/US1999/020883 filed Sep. 23, 1999 Search Report dated Jan. 20, 2000.
PCT/US2006/017889 filed May 9, 2006 International Preliminary Report on Patentability dated Jul. 14, 2009.
PCT/US2006/017889 filed May 9, 2006 International Search Report dated Jul. 1, 2009.
PCT/US2006/017889 filed May 9, 2006 Written Opinion dated Jul. 1, 2009.
PCT/US2006/017890 filed May 9, 2006 Preliminary Report on Patentability dated Feb. 12, 2008.
PCT/US2006/017890 filed May 9, 2006 Search Report dated Nov. 2, 2006.
PCT/US2006/017890 filed May 9, 2006 Written Opinion dated Nov. 2, 2006.
PCT/US2006/044826 filed Nov. 17, 2006 International Preliminary Report on Patentability and Written Opinion dated Apr. 10, 2008.
PCT/US2006/044826 filed Nov. 17, 2006 International Search Report dated Apr. 10, 2008.

(56) References Cited

OTHER PUBLICATIONS

PCT/US2006/045738 filed Nov. 11, 2006 Search Report dated Oct. 9, 2007.
PCT/US2006/045738 filed Nov. 11, 2006 Written Opinion dated Oct. 9, 2007.
PCT/US2007/009186 filed Apr. 16, 2007 International Preliminary Report on Patentability and Written Opinion dated Nov. 4, 2008 and Sep. 29, 2008.
PCT/US2007/009186 filed Apr. 16, 2007 International Search Report dated Sep. 29, 2008.
PCT/US2010/043787 filed Jul. 29, 2010 Search Report dated Dec. 3, 2010.
PCT/US2010/043787 filed Jul. 29, 2010 Written Opinion dated Dec. 3, 2010.
Peck, K. E. et al., "Postlaparoscopic Traumatic Inferior Vena Caval Thrombosis", Heart & Lung, Jul./Aug. 1998, vol. 27, No. 4, pp. 279-281.
Pelage, J. et al., "Re: Leiomyoma Recurrence After Uterine Artery Embolization", Journal of Vascular and Interventional Radiology, Jul. 2004, vol. 15, No. 7, pp. 773-776.
Peskin, Gerald R. (ed.), Papers of the Western Surgical Association, "Directed Parathyroidectomy—Feasibility and Performance in 100 Consecutive Patients With Primary Hyperparathyroidism", Archives of Surgery, Jun. 2003, vol. 138, p. 581.
Peterson, D. A. et al., "Computed Tomographic Venography is Specific But Not Sensitive for Diagnosis of Acute Lower-Extremity Deep Venous Thrombosis in Patients With Suspected Pulmonary Embolus", Journal of Vascular Surgery, 2001, 34:798-804.
Podnos, Y. D. et al., "Complications After Laparoscopic Gastric Bypass", Archives of Surgery, Sep. 2003, 138:957-961.
Poletti, P.A. et al., "Long-Term Results of the Simon Nitinol Inferior Vena Cava Filter", Eur. Radiol., 1998, vol. 8, pp. 289-294.
Ponchon, M. et al., "Temporary Vena Caval Filtration Preliminary Clinical Experience With Removable Vena Caval Filters", Acta Clinica Belgica, 1999, vol. 54, pp. 223-228.
Porcellini, Massimo et al., "Intracardiac Migration of Nitinol TrapEase™ Vena Cava Filter and Paradoxical Embolism", European Journal of Cardio-Thoracic Surgery, vol. 22, 2002, pp. 460-461.
Porter, J. M. et al., "Reporting Standards in Venous Disease: An Update", Journal of Vascular Surgery, 1995, 21:635-645.
Poster: Clinical Science: Pulmonary Disease or Dysfunctional/Mechanical Ventilation/Weaning (Adult), Critical Care Medicine, vol. 32, No. 12 (Suppl.), pp. A111-A120, 2004.
Prince et al., "Local Intravascular Effects of the Nitinol Wire Blood Clot Filter" Investigative Radiology 23:294-390 (Apr. 1988).
Prince, M. R. et al., "The Diameter of the Inferior Vena Cava and Its Implications for the Use of Vena Caval Filters", Radiology, 1983, 149:687-689.
Proctor, M. C. et al., "Assessment of Apparent Vena Caval Penetration by the Greenfield Filter", Journal of Endovascualr Surgery, 1998, 5:251-258.
Proctor, M. C., "Indications for Filter Placement", Seminars in Vascular Surgery, Sep. 2000, vol. 13, No. 3, pp. 194-198.
Putnam et al., "Placement of Bilateral Simon Nitinol Filters for an Inferior Vena Cava Duplication through a Single Groin Access" JVIR 10:431-433 (1999).
Putterman, Daniel et al., "Aortic Pseudoaneurysm After Penetration by a Simon Nitinol Inferior Vena Cava Filter", J Vasc Interv Radiol, 2005, 16:535-538.
Qanadli, S. D. et al., "Pulmonary Embolism Detection: Prospective Evaluation of Dual-Section Helical CT Versus Selective Pulmonary Arteriography in 157 Patients", Radiology, 2000, 217:447-455.
Qian et al., "In Vitro and In Vivo Experimental Evaluation of a New Vena Caval Filter" JVIR 5:513-518 (1994).
Quality Improvement Guidelines for Percutaneous Inferior Vena Cava Filter Placement for the Prevention of Pulmonary Embolism (European Standards adopted and Modified by CIRSE in Cooperation With SCVIR Standards of Practice Committee), http:www.cirse.org/vena_cava_filter_crise.htm, retrieved May 17, 2002, 11 pages.
Questions and Answers: Vena Caval filters and anticoagulants, JAMA; Oct. 20, 1993; 270, 15; pp. 1867-1868.
Quirke, T. E. et al., "Inferior Vena Caval Filter Use in U.S. Trauma Centers" A Practitioner Survey, The Journal of Trauma: Injury, Infection, and Critical Care, 1997, vol. 43, No. 2, pp. 333-337.
Rabkin, D. J. et al., "Nitinol Properties Affecting Uses in Interventional Radiology", Journal of Vascular and Interventional Radiology, 2000, 11:343-350.
Radke, P. W. et al., "Thrombosis in Behcet's Disease: Report of a Case Followed by a Systematic Review Using the Methodology of Evidence-Based Medicine", Journal of Thrombosis and Thrombolysis, Apr. 2001, 11(2):137-141.
Rajan, Dheeraj K. et al., "Retrieval of the Bard Recovery Filter from the Superior Vena Cava," JVIR, Letters to the Editor, vol. 15, No. 10, Oct. 2004, pp. 1169-1171.
Raju, N. L. et al., "Case 37: Juxtacaval Fat Collection—Mimic of Lipoma in the Subdiaphragmatic Inferior Vena Cava", Radiology, 2001, 220:471-474.
Rascona, D. A. et al., "Pulmonary Embolism-Treatment vs Nontreatment", Chest, Jun. 1999, vol. 115, No. 6, p. 1755.
Ray Jr., C. E. et al., "Complications of Inferior Vena Cava Filters", Abdominal Imaging, 1996, 21:368-374.
Razavi, M. K. et al., "Chronically Occluded Inferior Venae Cavae: Endovascular Treatment", Radiology, 2000, 214:133-138.
RD Heparin Arthroplasty Group, "RD Heparin Compared With Warfarin for Prevention of Venous Thromboembolic Disease Following Total Hip or Knee Arthroplasty", The Journal of Bone and Joint Surgery, Incorporation, Aug. 1994, vol. 76-A, No. 8, pp. 1174-1185.
Reddy, K. et al., "Insertion of an Inferior Venocaval Filter in a Pregnant Woman at Risk for Pulmonary Embolism—A Challenging Management", Departments of Obstetrics and Gynaecology and Radiology, Wexham Park Hospital, Slough, UK, 2003, p. 198.
Reed, Ricahrd A., "The Use of Inferior Vena Cava Filters in Pediatric Patients for Pulmonary Embolus Prophylaxis", Cardiovascular and Interventional Radiology, 1996,19:401-405.
Reekers, J. A. et al., "Evaluation of the Retrievability of the OptEase IVC Filter in an Animal Model", Journal of Vascular and Interventional Radiology, 2004, 15:261-267.
Reekers, Jim A., "Re Current Practice of Temporary Vena Cava Filter Insertion: A Multicenter Registry", Journal of Vascular Interventional Radiology, Nov.-Dec. 2000, pp. 1363-1364.
Ricco, Jean Baptiste et al., "Percutaneous Transvenous Caval Interruption with the LGM Filter", Ann Vasc Surg, 1988,3:242-247.
Ricotta, J. J., "Regarding Recurrent Thromboembolism in Patients With Vena Cava Filters", Journal of Vascular Surgery, 2001, vol. 33, p. 657.
Riedel, M., "Acute Pulmonary Embolism 2: Treatment", Heart, Mar. 2001, 85(3):351-360.
Robinson, Jeffrey D. et al., "In Vitro Evaluation of Caval Filters", Cardiovascular and Interventionalradiology, 1988, 11 :346-351.
Robrer, M. J. et al., "Extended Indications for Placement of an Inferior Vena Cava Filter", Journal of Vascular Surgery, Jul. 1990, vol. 12, No. 1.
Rodrigues, H. L. et al., "Update of the Management of Venous Thromboembolism [16]", Rev Port Cardiol, 2002, 21(2):183-199.
Rodriguez, J. L. et al., "Early Placement of Prophylactic Vena Caval Filters in Injured Patients at High Risk for Pulmonary Embolism", The Journal of Trauma, Injury, Infection, and Critical Care, 1996, vol. 40, No. 5, pp. 797-804.
Roehm Jr., John O. F. et al., "The Bird's Nest Inferior Vena Cava Filter: Progress Report", Radiology, Sep. 1988,168:745-749.
Roehm Jr., John O. F., "The Bird's Nest Filter: A New Percutaneous Transcatheter Inferior Vena Cava Filter", Journal of Vascular Surgery, Oct. 1984, vol. 1, No. 3.
Rogers, F. B. et al., "Five-Year Follow-Up of Prophylactic Vena Cava Filters in High-Risk Trauma Patients", Archives of Surgery, Apr. 1998, 133:406-411.
Rogers, F. B. et al., "Immediate Pulmonary Embolism After Trauma: Case Report", Journal of Trauma: Injury, Infection, and Critical Care, vol. 48, No. 1, pp. 146-148.
Rogers, F. B. et al., "Practice Management Guidelines for the Prevention of Venous Thromboembolism in Trauma Patients: The East

(56) References Cited

OTHER PUBLICATIONS

Practice Management Guidelines Work Group", The Journal of Trauma: Injury, Infection, and Critical Care, Jul. 2002, 53:142-164.
Rogers, F. B. et al., "Prophylactic Vena Cava Filter Insertion in Selected High-Risk Orthopaedic Trauma Patients", Journal of Orthopaedic Trauma, 1997, 11(4):267-272.
Rogers, F. B. et al., "Prophylactic Vena Cava Filter Insertion in Severely Injured Trauma Patients: Indications and Preliminary Results", The Journal of Trauma, Oct. 1993, 35(4):637-642.
Rogers, F. B. et al., "Routine Prophylactic Vena Cava Filter Insertion in Severely Injured Trauma Patients Decreases the Incidence of Pulmonary Embolism", Journal of the American College of Surgeons, Jun. 1995 180 (6):641-647.
Rogers, F. B., "Venous Thromboembolism in Trauma Patients: A Review", Surgery, Jul. 2001, vol. 130, No. 1, pp. 1-12.
Rohrer, M. J. et al., "Extended Indications for Placement of an Inferior Vena Cava Filter", Journal of Vascular Surgery, Jul. 1989, vol. 10. No. 1, pp. 44-50.
Rose, S. C. et al., "Placement of Inferior Vena Caval Filters in the Intensive Care Unit", Journal of Vascular and Interventional Radiology, 1997, 8:61-64.
U.S. Appl. No. 11/966,203, filed Dec. 28, 2007 Final Office Action dated Dec. 4, 2009.
U.S. Appl. No. 11/966,203, filed Dec. 28, 2007 Non-Final Office Action dated Aug. 17, 2009.
U.S. Appl. No. 11/997,832, filed Aug. 20, 2008 Non-Final Office Action dated Aug. 16, 2010.
U.S. Appl. No. 11/997,832, filed Aug. 20, 2008 Non-Final Office Action dated Feb. 23, 2011.
U.S. Appl. No. 12/093,814, filed Jun. 8, 2009 Non-Final Office Action dated Jul. 10, 2012.
U.S. Appl. No. 12/095,700, filed Jun. 17, 2010 Non-Final Office Action dated Jun. 11, 2012.
U.S. Appl. No. 12/095,991, filed Jul. 31, 2008 Final Office Action dated May 4, 2012.
U.S. Appl. No. 12/095,991, filed Jul. 31, 2008 Non-Final Office Action dated Nov. 14, 2011.
U.S. Appl. No. 12/299,300, filed Feb. 24, 2009 Non-Final Office Action dated Apr. 30, 2012.
U.S. Appl. No. 12/299,300, filed Feb. 24, 2009 Notice of Allowance dated Aug. 17, 2012.
U.S. Appl. No. 12/299,304, filed Jun. 16, 2009 Non-Final Office Action dated Jun. 21, 2012.
U.S. Appl. No. 12/303,545, filed Jun. 29, 2009 Non-Final Office Action dated Jun. 8, 2012.
U.S. Appl. No. 12/336,454, filed Dec. 12, 2008 Non-Final Office Action dated Jan. 24, 2011.
U.S. Appl. No. 12/727,116, filed Mar. 18, 2010 Non-Final Office Action dated Jul. 18, 2012.
U.S. Appl. No. 12/846,680, filed Jul. 29, 2010 Non-Final Office Action dated May 7, 2012.
U.S. Appl. No. 13/009,727, filed Jan. 19, 2011 Notice of Allowance dated Apr. 27, 2012.
U.S. Appl. No. 13/170,054, filed Jun. 27, 2011 Non-Final Office Action dated Jul. 2, 2012.
Valji, K., "Evolving Strategies for Thrombolytic Therapy of Peripheral Vascular Occlusion", Journal of Vascular and Interventional Radiology, 2000, 11:411-420.
Van Ha, Thuong G. et al., "Removal of Gunther Tulip Vena Cava Filter Through Femoral Vein Approach", Journal of Vascular and Interventional Radiology, 2005, 16:391-394.
Van Natta, Timothy L. et al., "Elective Bedside Surgery in Critically Injured Patients is Safe and Cost-Effective", American Surgery, May 1998, 227(5):618-626.
Vedantham, S. et al., "Endovascular Recanalization of the Thrombosed Filter-Bearing Inferior Vena Cava", Journal of Vascular and Interventional Radiology, 2003, 14:893-903.
Vedantham, S. et al., "Lower Extremity Venous Thrombolysis With Adjunctive Mechanical Thrombectomy", Journal of Vascular and Interventional Radiology, 2002, 13:1001-1008.
Vedantham, S. et al., "Pharmacomechanical Thrombolysis and Early Stent Placement for Iliofemoral Deep Vein Thrombosis", Journal of Vascular and Interventional Radiology, 2004, 15:565-574.
Velmahos, G. C. et al., "Inability of an Aggressive Policy of Thromboprophylaxis to Prevent Deep Venous Thrombosis (DVT) in Critically Injured Patients: Are Current Methods of DVT Prophylaxis Insufficient?", Journal of the American College of Surgeons, 1998, 187:529-533.
Velmahos, G. C. et al., "Prevention of Venous Thromboembolism After Injury: An Evidence-Based Report-Part 1: Analysis of Risk Factors and Evaluation of the Role of Vena Caval Filters", The Journal of Trauma: Injury, Infection, and Critical Care, Jul. 2000, 49:132-139.
Velmahos, G. C. et al., "Prevention of Venous Thromboembolism After Injury: An Evidence—Based Report-Part II: Analysis of Risk Factors and Evaluation of the Role of Vena Caval Filters", The Journal of Trauma: Injury, Infection, and Critical Care, Jul. 2000, 49:140-144.
Velmahos, G. C. et al., "Spiral Computed Tomography for the Diagnosis of Pulmonary Embolism in Critically Ill Surgical Patients", Archives of Surgery, May 2001, 136(5):505-511.
Venbrux, Anthony C., "Protection Against Pulmonary Embolism: Permanent and Temporary Caval Filters" Department of Radiology-CVDL, The Johns Hopkins Medical Institutions, Baltimore MD, 7 pages.
Vesely, T. M. et al., "Preliminary Investigation of the Irie Inferior Vena Caval Filter", Journal of Vascular and Interventional Radiology, 1996, 7:529-535.
Vorwerk, D. et al., "Use of a Temporary Caval Filter to Assist Percutaneous Iliocaval Thrombectomy: Experimental Results", Journal of Vascular and Interventional Radiology, Sep.-Oct. 1995, 6(5):737-740.
Vos, Louwerens D. et al., "The Gunther Temporary Inferior Vena Cava Filter for Short-Term Protection Against Pulmonary Embolism", Cardiovascular and Interventionai Radiology, 1997, 20:91-97.
Vrachliotis, T. G. et al., "Percutaneous Management of Extensive Clot Trapped in a Temporary Vena Cava Filter", Journal of Endovascular Therapy, 2003, 10:1001-1005.
Wakefield, T. W., Treatment Options for Venous Thrombosis, Journal of Vascular Surgery, Mar. 2000, 31(3):613-620.
Wallace, M. J. et al., "Inferior Vena Caval Stent Filter", AJR, Dec. 1986, 147:1247-1250.
Wallace, M. J., "Transatrial Stent Placement for Treatment of Inferior Vena Cava Obstruction Secondary to Extension of Intracardiac Tumor Thrombus From Hepatocellular Carcinoma", Journal of Vascular Interventional Radiology, 2003, 14:1339-1343.
Wang, W. Y. et al., "Use of a Nitinol Gooseneck Snare to Open an Incompletely Expanded Over-the-Wire Stainless Steel Greenfield Filter", American Journal of Roentgenology, Feb. 1999, 172:499-500.
Watanabe, N. et al., "Images in Cardiology: Large Thrombus Entrapped in a Patent Foramen Ovale of the Atrial Septum, Which Apparently "Disappeared" Without Embolic Events", Heart, Nov. 2002, 88(5):474.
Watanabe, S. et al., "Superior Vena Caval Placement of a Temporary Filter: A Case Report", Vascular Surgery, Jan./Feb. 2001, vol. 35, Issue 1.
Watanabe, Shun-ichi et al., "Clinical Experience With Temporary Vena Cava Filters", Vascular Surgery, vol. 35, No. 4, 2001, pp. 285-291.
Weeks, S. M. et al., "Primary Gianturco Stent Placement for Inferior Vena Cava Abnormalities Following Liver Transplantation", Journal of Vascular and Interventional Radiology, Feb. 2000, 11:177-187.
Welch, H. J. et al., "Duplex Assessment of Venous Reflux and Chronic Venous Insufficiency: The Significance of Deep Venous Reflux", Journal of Vascular Surgery, 1996, 24:755-762.
Wellons, E. D. et al., "Bedside Intravascular Ultrasound-Guided Vena Cava Filter Placement", Journal of Vascular Surgery, 2003, 38:455-458.
Wells, J. L. et al., "Diagnosing Pulmonary Embolism: A Medical Masquerader", Clinician Reviews, 2001, 11(2):66-79.

(56) References Cited

OTHER PUBLICATIONS

Westling, A. et al., "Incidence of Deep Venous Thrombosis in Patients Undergoing Obesity Surgery", World Journal of Surgery, 2002, 26:470-473.
White, R. H. et al., "A Population-Based Study of the Effectiveness of Inferior Vena Cava Filter Use Among Patients With Venous Thromboembolism", Archives of Internal Medicine, Jul. 10, 2000, 160(13):2033-2041.
Whitehill, T. A., "Current Vena Cava Filter Devices and Results", Seminars in Vascular Surgery, Sep. 2000, 13(3):204-212.
Wholey, M. et al., "Technique for Retrieval of a Guidewire Lodged in a Vena Cava Filter", Vascular and Endovascular Surgery, 2002, 36(5):385-387.
Wiles, C. E., Letters to Editor, Journal of Trauma, Aug. 1999, 47(2):438.
Wilson, J. T. et al., "Prophylactic Vena Cava Filter Insertion in Patients With Traumatic Spinal Cord Injury: Preliminary Results", Neurosurgery, 1994, 35:234-239.
Winchell, R. J. et al., "Risk Factors Associated With Pulmonary Embolism Despite Routine Prophylaxis: Implications for Improved Protection", The Journal of Trauma, 1994, 37(4):600-606.
"Staff Development Special, Get the Edge on Deep Vein Thrombosis", Nursing Management, Jan. 2004, pp. 21-29.
AbuRahma, A.F. et al., "Endovascular Caval Interruption in Pregnant Patients With Deep Vein Thrombosis of the Lower Extremity", Journal of Vascular Surgery, 2001, 33:375-378.
AbuRahma, A.F. et al., "Management of Deep Vein Thrombosis of the Lower Extremity in Pregnancy: A Challenging Dilemma", The American Surgeon, Feb. 1999, vol. 65, No. 2, pp. 164-167A.
AbuRahma, F. et al., "Etiology of Peripheral Arterial Thromboembolism in Young Patients", The American Journal of Surgery, vol. 176, Aug. 1998, pp. 158-161.
Adams, E. et al., "Retrievable Inferior Vena Cava Filter for Thrombolic Disease in Pregnancy", British Journal of Obstetrics and Gynaecology, Sep. 1998, vol. 105, pp. 1039-1042.
Adye, B. A., "Case Report: Errant Percutaneous Greenfield Filter Placement Into The Retroperitoneum", Journal of Vascular Surgery, Jul. 1990, vol. 12, No. 1.
Ahearn, G.S. et al., "Massive Pulmonary Embolism During Pregnancy Successfully Treated With Recombinant Tissue Plasminogen Activator", Archives of Interal Medicine, Jun. 10, 2002, 162(11):1221-1227.
Aklog, L. et al., "Acute Pulmonary Embolectomy", Circulation, 2002, 105:1416-1419.
Alexander, J. J. et al., "Is the Increasing Use of Prophylactic Percutaneous IVC Filters Justified?", The American Journal of Surgery, Aug. 1994, vol. 168, pp. 102-106.
Allen, T.L. et al., "Retrievable Vena Cava Filters in Trauma Patients for High-Risk Prophylaxis and Prevention of Pulmonary Embolism", The American Journal of Surgery, 2005, 189:656-661.
American Gastroenterological Association Clinical Practice Committee, "Technical Review on Obesity," Sep. 2002 123:883-932.
Anderson, J.T. et al., "Bedside Noninvasive Detection of Acute Pulmonary Embolism in Critically Ill Surgical Patients", Archives of Surgery, Aug. 1999, 134(8):869-875.
Andrews, R. T. et al., "Entrapment of J-Tip Guidewires by Venatech and Stainless-Steel Greenfield Vena Cava Filters During Central Venous Catheter Placement: Percutaneous Management in Four Patients", Correspondence to R.T. Andrews, M.D., The Dotter Interventional Institute, Oregon Heal Sciences University, Portland, OR, pp. 424-427.
Anthone, G.J. et al., The Duodenal Switch Operation for the Treatment of Morbid Obesity, Annals of Surgery, Oct. 2003, 238(4):618-628.
Arcasoy, S.M. et al., "Thrombolytic Therapy of Pulmonary Embolism", Chest, 1999, 115:1695-1707.
Arcelus, J.I. et al, "The Management and Outcome of Acute Venous Thromboembolism: A Prospective Registry Including 4011 Patients", Journal of Vascular Surgery, 2003, 38:916-922.

Arjomand, H. et al., "Right Ventricular Foreign Body: Percutaneous Transvenous Retrieval of a Greenfield Filter From the Right Ventricle", Angiology, 2003, vol. 54, No. 1, pp. 109-113.
Arnold, D.M. et al., "Missed Opportunities for Prevention of Venous Thromboembolism", Chest, 2001, 120:1964-1971.
Ascer, E. et al., "Superior Vena Caval Greenfield Filters: Indications, Techniques, and Results", Journal of Vascular Surgery, Mar. 1996, vol. 23, No. 3.
Asch, M. R., "Initial Experience in Humans With a New Retrievable Inferior Vena Cava Filter", Radiology, 2002, 225:835-844.
Ascher, E. et al., "Lessons Learned From a 6-Year Clinical Experience With Superior Vena Cava Greenfield Filters", Journal of Vascular Surgery, Nov. 2000, 32:881-887.
Ashley, D.W. et al., "Accurate Deployment of Vena Cava Filters: Comparison of Intravascular Ultrasound and Contrast Venography", The Journal of Trauma Injury, Infection, and Critical Care, Jun. 2001, vol. 50, No. 6, pp. 975-981.
Aswad, M. A. et al., "Early Duplex Scan Evaluation of Four Venal Interruption Devices", Journal of Vascular Surgery, 1996, 24:809-818.
Athanasoulis, C.A. et al., "Inferior Venal Caval Filters: Review of a 26-Year Single-Center Clinical Experience", Radiology, 2000, 216:54-66.
Authors' Abstract, "Abstracts of Current Literature", Journal of Vascular and Interventional Radiology, Mar. 2000, vol. 11, No. 3, pp. 401-407.
Authors' Abstract, "Abstracts of Current Literature", Journal of Vascular and Interventional Radiology, Oct. 2003, vol. 14, No. 10, pp. 1351-1357.
Authors' Abstract, "Abstracts of Current Literature," Journal of Vascular and Interventional Radiology, Oct. 2002, 13(10):1062-1068.
Authors' Abstracts, "Abstracts of Current Literature", Journal of Vascular and Interventional Radiology, Apr. 2002, vol. 13, No. 4, pp. 433-440.
Authors' Abstracts, "Abstracts of Current Literature", Journal of Vascular and Interventional Radiology, Apr. 2004, pp. 408-415.
Avery, M. et al., "Reverse Engineering of Nitinol Vena Cava Filters", Material Science 102 Semester Project, Nov. 21, 2000.
Baker, R. J., "Treatment Considerations for Inherited Thrombophilia and Pulmonary Embolus", Archives of Surgery, Feb. 2001, 136,2:237.
Balshi, J. D. et al., "Original Articles" Complications of Caval Interruption by Greenfield Filter in Quadriplegics, Journal of Vascular Surgery, Apr. 1989, vol. 9, No. 4.
Barraco, R. D. et al., "Dislodgment of Inferior Vena Cava Filters During Central Line Placement: Case Report", The Journal of Trauma, Injury, Infection and Critical Care, 2000, vol. 48, No. 1, pp. 140-142.
Barreras, J. R. et al., "Recurrent Pulmonary Embolism Despite the Use of a Greenfield Filter", Clinical Nuclear, Dec. 2001, vol. 26, No. 12, pp. 1040-1041.
Barton, A. L. et al., "Caval Filter Placement for Pulmonary Embolism in a Patient With a Deep Vein Thrombosis and Primary Intracerebral Haemorrhage", Age and Ageing, Mar. 2002, 31,2:144-146.
Bass, B.L., "What's New in General Surgery: Gastrointestinal Conditions",The Journal of American College Surgeons, Dec. 2002, vol. 195, No. 6, pp. 835-854.
Becker, D. M. et al., "Inferior Vena Cava Filters", Archives of Internal Medicine, Oct. 1992, vol. 152, pp. 1985-1994.
Bendick, P.J. et al., Serial Duplex Ultrasound Examination for Deep Vein Thrombosis in Patients With Suspected Pulmonary Embolism, Journal of Fascular Surgery, Nov. 1996, vol. 24, No. 5, pp. 732-737.
Benjamin, M. E. et al., Duplex Ultrasound Insertion of Inferior Vena Cava Filters in Multitrauma Patients:, American Journal of Surgery, Aug. 1999, vol. 178, pp. 92-97.
Bessoud, B. et al., Experience at a Single Institution With Endovascular Treatment of Mechanical Complications Caused by Implanted Central Venous Access Devices in Pediatric and Adult Patients, American Journal of Roentgenology, Feb. 2003, 180:527-532.
Bevoni, L., "Management of Adult Obesity", Clinician Reviews, May 2003, 13(5):56-62.

(56) References Cited

OTHER PUBLICATIONS

Biertho, L. et al., "Laparoscopic Gastric Bypass Versus Laparoscopic Adjustable Gastric Banding: A Comparative Study of 1,200 Cases", Journal of the American Colloge of Surgeons, Oct. 2003, vol. 197, No. 4, pp. 536-545.

Binkert, C. A. et al., "Inferior Vena Cava Filter Removal After 317-Day Implantation", Journal of Vascular Radiology, Mar. 2005, 16:393-398.

Bjarnason, H. et al., "In Vitro Metal Fatigue Testing of Inferior Vena Cava Filters", Investigative Radiology, 1994, vol. 29, No. 9, pp. 817-821.

Blachar A. et al., "Gastrointestinal Complications of Laparoscopic Roux-en-Y Gastric Bypass Surgery in Patients Who Are Morbidly Obese: Findings on Radiography and CT", American Journal of Roentgenology, Dec. 2002, 179:1437-1442.

Blachar, A. et al., "Gastrointestinal Complications of Laparoscopic Roux-en-Y Gastric Bypass Surgery: Clinical and Imaging Findings", Radiology, 2002, 223:625-632.

Blaszyk, H. et al., "Factor V Leiden and Morbid Obesity in Fatal Postoperative Pulmonary Embolism", Archives of Surgery, Dec. 2000, 135(12):1410-1413.

Blebea J. et al., "Deep Venous Thrombosis After Percutaneous Insertion of Vena Caval Filters", Journal of Vascular Surgery, Nov. 1999, 30:821:829.

Bochenek, K. M. et al., "Right Atrial Migration and Percutaneous Retrieval of a Gunther Tulip Inferior Vena Cava Filter", Journal of Vascular Interventional Radiology, Sep. 2003, 14:1207-1209.

Bochicchio, G. V. et al., "Acute Caval Perforation by an Inferior Vena Cava Filter in a Multitrauma Patient: Hemostatic Control With a New Surgical Hemostat", The Journal of Trauma Injury, Infection and Critical Care, 2001, 51:991-993.

\* cited by examiner

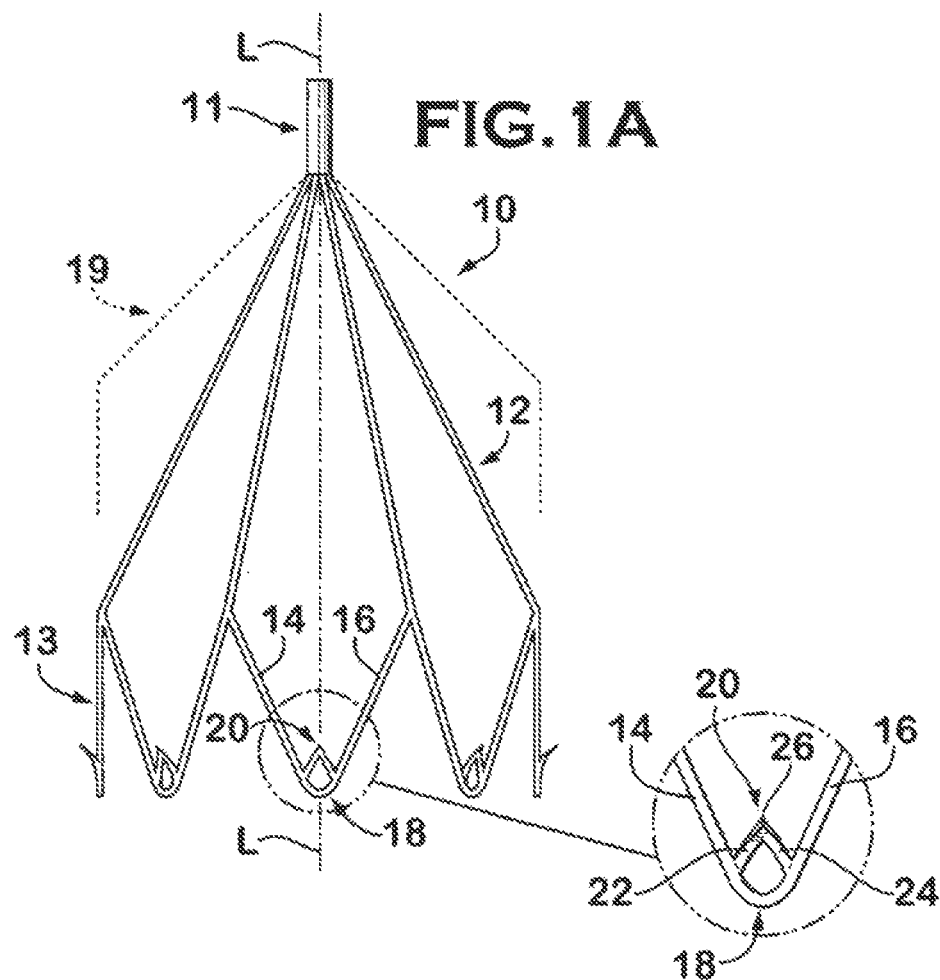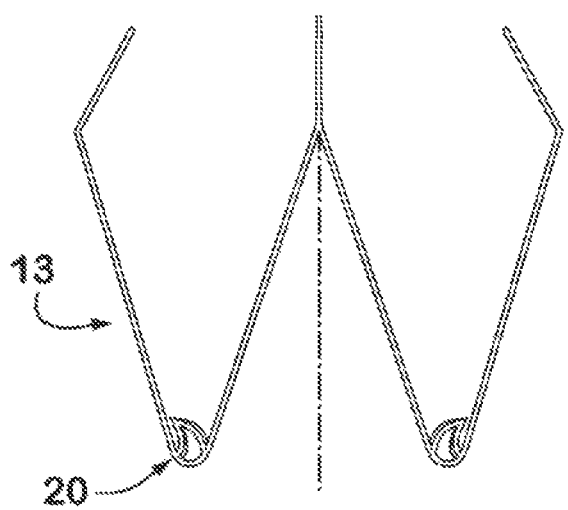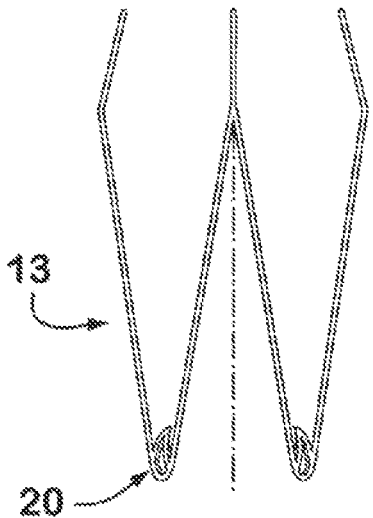

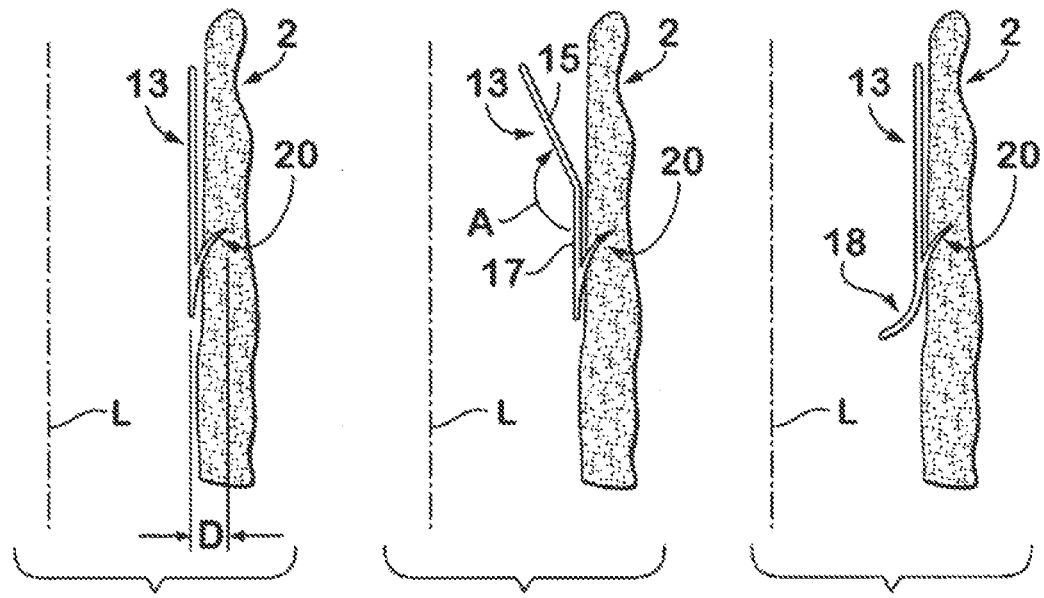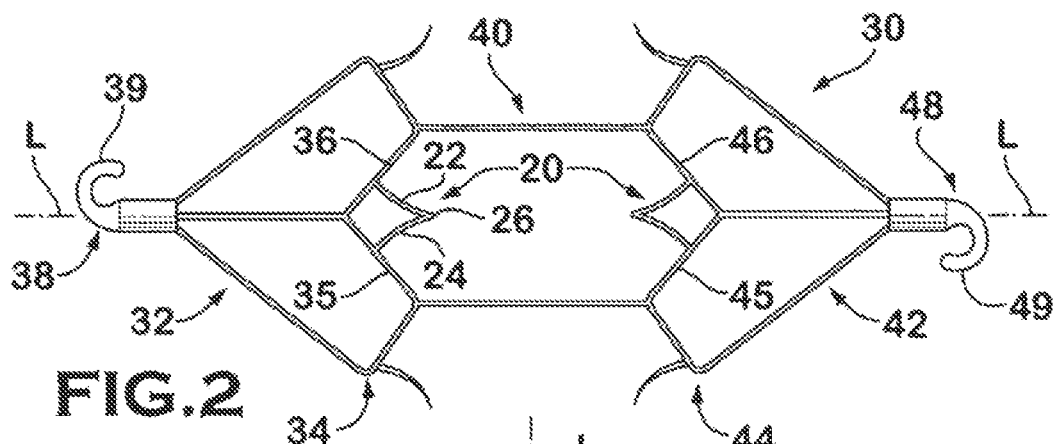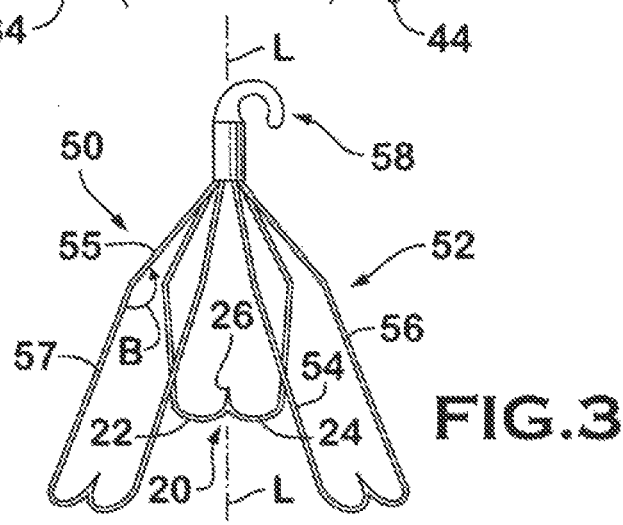

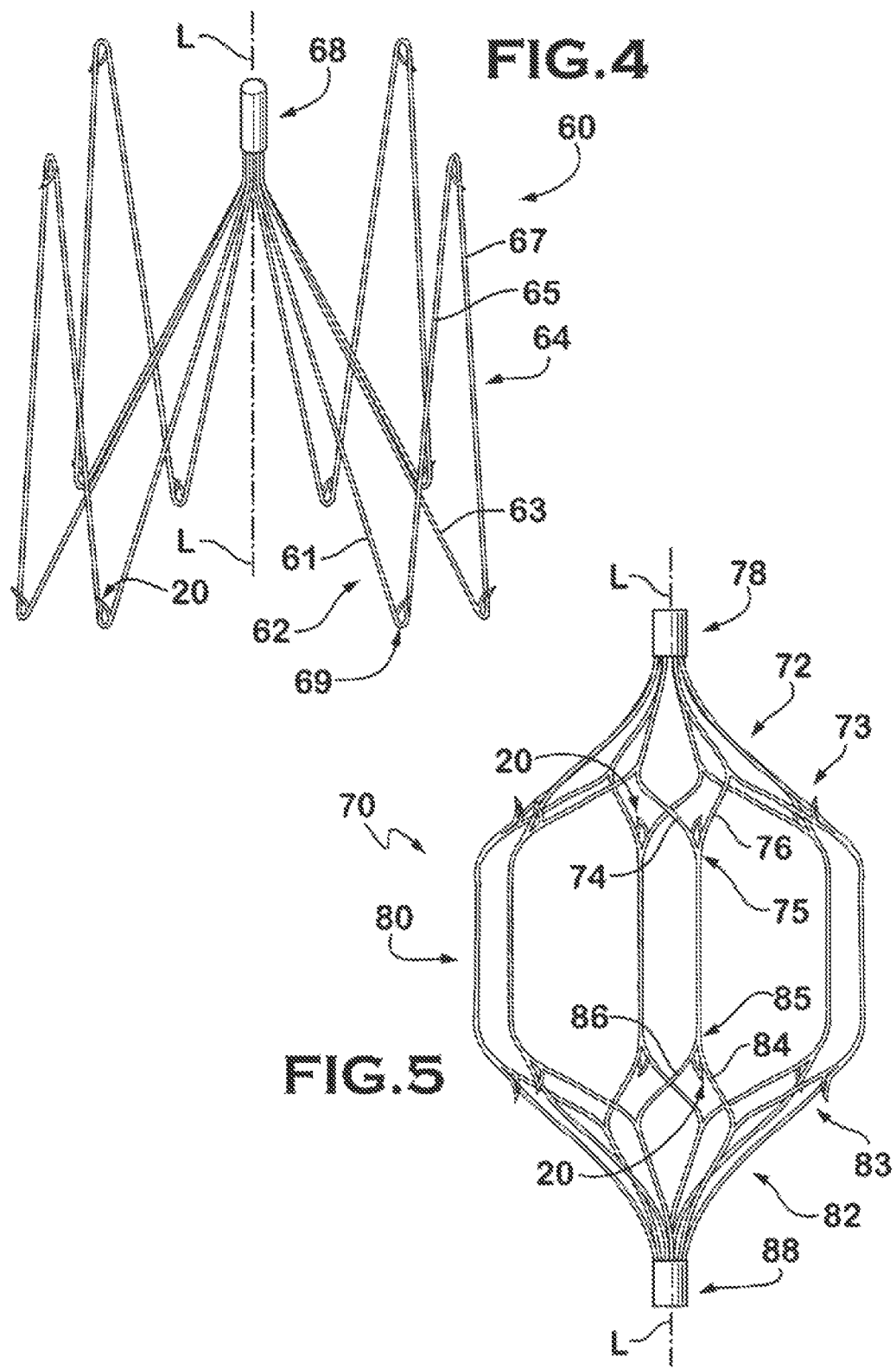

IVC FILTER WITH TRANSLATING HOOKS

PRIORITY

This application is a continuation-in-part of U.S. patent application Ser. No. 12/299,300, filed Apr. 16, 2007 as a U.S. national stage application under 35 U.S.C. §371 of International Application No. PCT/US2007/009215, claiming the benefit of priority to U.S. Provisional Application No. 60/797,006, filed May 2, 2006. This application is also a continuation-in-part of U.S. patent application Ser. No. 13/009,727, filed Jan. 19, 2011, now U.S. Pat. No. 8,241,350, which is a continuation of U.S. patent application Ser. No. 11/966,203, filed Dec. 28, 2007, now U.S. Pat. No. 7,887,580, which is a continuation of U.S. patent application Ser. No. 10/079,155, filed Feb. 20, 2002, now U.S. Pat. No. 7,331,992. Each of the aforementioned applications is incorporated by reference into this application as if fully set forth herein.

BACKGROUND OF THE INVENTION

Inferior vena cava (IVC) filters are devices configured for insertion into the inferior vena cava to capture particles that may be present in the blood stream which, if transported to, for example, the lungs could result in serious complications and even death. Typically, IVC filters are utilized in patients who have a contraindication to anticoagulation or in patients developing clinically apparent deep vein thrombosis (DVT) and/or pulmonary embolism (PE). Patients who have recently suffered from trauma, have experienced a heart attack (myocardial infarction), or who have undergone major surgical procedure (e.g., surgical repair of a fractured hip, etc.) may develop clinically apparent DVT. When a thrombus clot loosens from the site of formation and travels to the lung, it may cause PE, a life-threatening condition. An IVC filter may be placed in the circulatory system to intercept one or more clots and prevent them from entering the lungs. IVC filters are either permanent or retrievable.

There are many different configurations for IVC filters, including those that include a central hub from which extend a plurality of struts that form filter baskets having a conical configuration, such as disclosed in U.S. Pat. No. 6,258,026, which is incorporated by reference in its entirety into this application. Other IVC filter configurations utilize wires and/or frame members to form straining devices that permit flow of blood while trapping larger particles. IVC filters are generally configured for compression into a small size to facilitate delivery into the inferior vena cava and subsequent expansion into contact with the inner wall thereof. The IVC filter may later be retrieved from the deployed site by compressing the legs, frame members, etc., depending on the filter configuration. Typically, an IVC filter will include hooks or anchoring members for anchoring the filter in position within the inferior vena cava. The hooks may be more elastic than the legs or frame members to permit the hooks to straighten in response to withdrawal forces, which facilitate withdrawal from the endothelium layer of the blood vessel without risk of significant injury to the vessel wall.

One type of hook or anchoring device for an endoprosthesis is shown in U.S. Pat. No. 5,843,167, in the form of an assembly that is attached to a graft. The assembly includes anchors which are attached to a graft on either end and which are connected by wire struts that extend along the length of the graft. These anchors have hooks that are formed on the end of short segments of wire that are secured to the anchor. The hooks are adapted to protrude radially outwardly upon deployment of the endoprosthesis, extending a short distance beyond the bends of the anchor. U.S. Pat. No. 5,843,164 discloses an anchoring system that includes hooks to penetrate a vessel wall. The hooks are generally provided at each end of a stent graft, each hook having one or more barbs thereon. U.S. Pat. No. 5,591,197 discloses a different type of anchor in the form of deformable connecting members that attach cylindrical elements which together form a stent. Upon balloon expansion of the connecting members, a notched, weakened area is forced outward to form a barb to penetrate a vessel wall. U.S. Pat. No. 5,593,434 discloses a plurality of projections or teeth cut away from a sheet of material, which is curled into a cylinder to form a stent. One possible drawback to these and other anchoring systems is that the teeth or hooks attached or integrated into the grafts or stents have a tendency to catch on the delivery sheaths or catheters during deployment. This creates problematic situations in the deployment process as the teeth or hooks tear the sheath material, preventing the necessary precision required in percutaneous delivery into a body lumen.

The following references relate to filters: U.S. Pat. No. 5,324,304; U.S. Pat. No. 6,972,025; U.S. Patent Application Publication No. 2003/0176888; U.S. Patent Application Publication No. 2004/0193209; U.S. Patent Application Publication No. 2005/0267512; and U.S. Patent Application Publication No. 2005/0267515, each of which is incorporated by reference in its entirety into this application.

Applicants have recognized that it would be desirable to provide an IVC filter that incorporates translating hooks, such that delivery to and from a body vessel is facilitated. Embodiments of such IVC filters are described herein.

BRIEF SUMMARY OF THE INVENTION

Accordingly, described herein is a filter incorporating translating hooks. In one embodiment, a filter includes a body including a plurality of strut members disposed about a central axis to define an outer perimeter, each of the strut members including a first strut and a second strut, the body having a first outer perimeter in a first configuration and a second outer perimeter larger than the first outer perimeter in a second configuration, and a hook disposed between the first and second struts of at least one of the strut members, the hook having a first elongate member connected to a second elongate member to define a tip, the first elongate member having an end portion coupled to the first strut and the second elongate member having an end portion coupled to the second strut so that in the first configuration, the tip is oriented toward the central axis in a first direction, and in the second configuration, the tip is oriented away from the central axis in a second direction.

In another embodiment, a filter includes a body having a plurality of struts, each strut having a proximal end connected to a head and a distal end, with adjacent struts connected at their distal end by a connecting portion such that the body includes a plurality of distal connecting portions, and at least one of the plurality of distal connecting portions including a hook having an apex formed by the joining of a first elongate member and a second elongate member, the first elongate member attached to a first of said adjacent struts and the second elongate member attached to a second of said adjacent struts.

In one embodiment, a method of anchoring and recovering a filter in a blood vessel includes introducing the filter into a blood vessel, the filter comprising at least one hook including first and second portions that are joined together at one end thereof to form a tip and that are attached respectively to different portions of a filter body at an opposite end thereof, and expanding the first and second portions to direct the tip of the hook away from a central axis defined by the filter body such that the tip of the hook engages a wall of the blood vessel.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

FIG. 1A is front perspective view of one embodiment of a filter with translating hooks in an expanded configuration and an enlarged view of a translating hook.

FIGS. 1B-1C are illustrations of a strut member of the filter of FIG. 1A, shown respectively in an expanded and collapsed position.

FIG. 1D is a side view of an embodiment of a strut member for a filter, shown with a hook embedded in a blood vessel wall.

FIG. 1E is a side view of another embodiment of a strut member for a filter, shown with a hook embedded in a blood vessel wall.

FIG. 1F is a side view of yet another embodiment of a strut member for a filter, shown with a hook embedded in a blood vessel wall.

FIG. 2 is a side perspective view of a symmetrical filter with translating hooks, including dual retrieval members.

FIG. 3 is a front perspective view of one embodiment of a filter with translating hooks, including a retrieval member.

FIG. 4 is a perspective view of another embodiment of a filter with translating hooks.

FIG. 5 is a side perspective view of another embodiment of a filter with translating hooks.

DETAILED DESCRIPTION OF THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

While the examples provided herein are discussed with respect to IVC filters, it should be appreciated that the filter embodiments described herein could be used for filter applications that do not involve placing a filter device in the inferior vena cava. In other words, the filters described herein are not limited to IVC applications.

Further, as used herein the term "bio-resorbable" includes a suitable biocompatible material, mixture of various biocompatible materials or partial components of biocompatible material being altered into other materials by an agent present in the environment (e.g., a biodegradable material that degrades via a suitable mechanism such as hydrolysis when placed in biological tissue); such materials being removed by cellular activity or incorporated into the cellular structure (i.e., bioresorption, bioresorping, bioabsorption, or bioresorbable), such materials being degraded by bulk or surface degradation (i.e., bioerosion such as, for example, a water insoluble polymer that turns water-soluble in contact with biological tissue or fluid), or such materials being altered by a combination of one or more of biodegradable, bioerodable or bioresorbable activity when placed in contact with biological tissue or fluid.

Possible materials for the filters, or portions thereof, described herein include a suitable biocompatible material such as, for example, stainless steel, noble metals and their alloys, shape memory metals, shape memory alloys, super elastic metal, super elastic shape memory metal alloys, linear elastic shape memory metal, metal alloys, Phynox, Conichrome, titanium, stainless steel, shape memory polymers, polymers, bio-materials (e.g., metal alloys such as those shown and described in U.S. Pat. No. 6,287,332 and U.S. Patent Application Publication No. 2002/0004060, each of which is incorporated by reference in its entirety into this application), and combinations thereof. The filters, or portions thereof, described herein may include an anti-stick material on one or more surfaces. Examples of anti-stick materials, include, for example, fluorinated polytetrafluoroethylene (PTFE), polyurethane, and combinations thereof.

Where the filter is to be utilized with bio-active agents to control the formation of emboli, bio-active agents can be coated to a portion or the entirety of the filter for controlled release of the agents once the filter is implanted. The bio-active agents can include, but are not limited to, vasodilator, anti-coagulants, such as, for example, warfarin and heparin. Other bio-active agents can include, but are not limited to, agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b$/$III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Referring now to FIG. 1A, a filter 10 is shown, including a hub 11, a set of legs 12 and a set of strut members 13. The filter 10 is illustrated in FIG. 1A in an expanded configuration, defining an expanded perimeter. The hub 11 may include a retrieval member (e.g., a hook-like member) to facilitate retrieval of the filter 10 from the blood vessel. Optionally, shown in phantom, the filter 10 may also include a set of arms 19, which in one embodiment are shorter in length than the legs 12. The arms in one embodiment have a proximal end joined at the hub 11, extending first outwardly with respect to the central axis L of the filter 10 when the filter is in the expanded configuration to a shoulder and then distally with respect to the hub 11 and angularly with respect to the shoulder. The arms 19 may provide a centering function to the filter 10 and may include hooks or vessel-engaging members on their distal ends. Each leg 12 has a proximal end joined at the hub 11, extending radially outward from a central axis L when the filter 10 is in an expanded or deployed configuration, while each strut member 13 is positioned generally parallel to the central axis L when the filter 10 is in an expanded configuration. In this embodiment, there are an even number of legs 12, preferably eight, although any number of legs is possible and within the scope of the invention. For delivery of the filter 10 to a blood vessel, the filter 10 is compressed to a collapsed configuration, defining a collapsed perimeter smaller than the expanded perimeter, the set of legs 12 and set of strut members 13 being positioned generally parallel to the central axis L when the filter is in the collapsed configuration.

Each of the strut members 13 include a first strut 14 and a second strut 16 that have a proximal end connected to a distal end of adjacent legs 12 (i.e., the proximal end of the first strut 14 is connected to a distal end of one leg 12 and the proximal end of the second strut 16 is connected to the distal end of an adjacent leg 12). The first strut 14 and second strut 16 are connected at a distal end thereof by a connecting portion 18, which in the embodiment shown in FIG. 1A is a rounded, semi-circular shape, but which in other embodiments can be various other shapes. The connecting portion 18 can be a separate piece of material attached to the first and second struts 14, 16, but in the preferred embodiment, the first strut 14, second strut 16 and connecting portion 18 are one continuous member, created through processes known to one skilled in the art (e.g., molding, laser cutting of a tube or a sheet, etching, electro-discharge-machining). A hook 20 is disposed between the first strut 14 and second strut 16, the hook 20 including a first elongate member 22, connected at a distal end to the first strut 14, and a second elongate member 24, connected at a distal end to the second strut 16, the first and second elongate members 22, 24 connected together at a proximal end thereof to define a tip or apex 26 as best seen in the enlarged view of FIG. 1A. Although a hook 20 is shown in FIG. 1A between each of the strut members 13, in other embodiments only select strut members 13 include a hook 20 (e.g., in a filter including eight strut members 13, only four strut members 13 include a hook with no two adjacent strut members 13 including hooks, etc.).

The hook 20 is configured such that the tip 26 is oriented away from the central axis L of the filter 10 in an expanded configuration (FIG. 1B), but oriented toward the central axis L of the filter 10 in a collapsed configuration (FIG. 1C), such that depending on the configuration of the filter 10, the tip 26 of the hook 20 can be oriented in different directions. The characteristic of the hook 20, in which the tip 26 is oriented in a different direction depending on the configuration of the filter, can be established, for example, through material properties of the hook 20, positioning of the hook 20 with respect to the first and second struts 14, 16, and/or shape of the elongate members 22, 24 (e.g., thickness, width, curvature, etc.) that form the hook 20. For instance, the angle formed between the first elongate member 22 and second elongate member 24, coupled with the stiffness of the material of the elongate members 22, 24 and the shape of thereof (e.g., slightly curved, tapered, decreasing thickness from the attachment end of the elongate members to the tip, etc.) can contribute to the directional orientation of the tip 26 in the expanded and collapsed configurations of the filter 10. Thus, the included angle defined by the tip between the expanded and collapsed configurations of the filter 10 can be equal to, greater than, or less than 180 degrees, although the presently preferred embodiment is less than 180 degrees. The change in orientation of the hook 20 depending on the configuration of the filter (i.e., expanded or collapsed) is described herein as "translation" of the hook, such that the filter 10 includes one or more "translating hooks." Examples of embodiments of a translating hook 20 can be found in U.S. Patent Application Publication No. 2003/0158595, which is incorporated by reference in its entirety into this application. The potential materials for the hook 20 are the same as those discussed herein as possible materials for the filter.

As shown in FIG. 1D, the orientation of the tip 26 of the hook 20 away from the central axis L when the filter 10 is in the expanded configuration results in the hook 20 becoming at least partially embedded into a blood vessel wall 2 when the filter 10 is deployed in the blood vessel. As shown, the depth penetration limit of the hook 20 is the distance D between the tip 26 and the distal end of the elongate members 24, 26 attached to the first and second struts 14, 16, respectively. FIG. 1F illustrates an embodiment for strut members 13 in which the connecting portion 18 is formed with a curvature that is oriented in a direction toward the central axis L. By orienting the connection portion 18 away from the blood vessel wall 2, tissue ingrowth into the strut members 13 is believed to be prevented, which facilitates removal of the filter 10 from the blood vessel. FIG. 1E illustrates an embodiment for strut members 13 in which an angle A is formed between a proximal section 15 and distal section 17 of the strut member 13 (i.e., a proximal and distal section of both of first and second struts 14, 16), such that the proximal section 15 of the strut member 13 is not in contact with the blood vessel wall 2, imparting a limited contact area (i.e., distal section 17) to the strut member 13. As a result, tissue ingrowth into the proximal section 15 is believed to be prevented, facilitating removal of the filter 10 from the blood vessel. In the example shown, the distal section 17 is generally parallel to the central axis L when the filter 10 is in the expanded configuration and the proximal section 15 is oriented in a direction toward the central axis L. The angle A between the proximal section 15 and distal section 17 of the strut member 13 is in the range of approximately 95 degrees to approximately 150 degrees, preferably in the range of approximately 110 degrees to approximately 130 degrees.

FIG. 2 illustrates a symmetrical retrievable filter 30, including a first hub 38 and a second hub 48, each hub containing a retrieval member 39, 49 with a hook-like configuration. The filter 30 is illustrated in an expanded configuration, defining an expanded perimeter. A first set of legs 32 extends from the first hub 38 radially outward from a central axis L, each leg 32 joined at a proximal end thereof to the first hub 38 and at a distal end to the first set of strut members 34. In the embodiment shown, each of the strut members 34 includes a first strut 35 and a second strut 36 that are proximally connected at the intersection of the leg 32 with the strut member 34. Thus, as shown, each leg 32 and strut member 34 together form a "Y" shape. The distal ends of the first and second struts 35, 36 are connected to adjacent struts 36, 35, respectively, of strut members 34 at the intersection of a connecting member 40, which lies approximately parallel to the central axis L and connects the first strut members 34 to the second strut members 44. Each of the second strut members 44 includes a first strut 45 and a second strut 46 that are proximally connected at the intersection of a leg 42 with the strut member 44 (also forming a "Y" shape with the leg 42). The distal ends of the first and second struts 45, 46 are connected to adjacent struts 46, 45, respectively, of strut members 44 at the intersection of the connecting member 40. A second set of legs 42 extends from the second hub 48 radially outward from a central axis L, each leg 42 joined at a proximal end thereof to the second hub 48 and at a distal end to the second set of strut members 44 as described.

Translating hooks 20 are attached to each of the strut members 34, 44 such that a first elongate member 22 is connected at a distal end to a first strut 35, 45 and a second elongate member 24 is connected to a second strut 36, 46, the elongate members 22, 24 connected together at a proximal end thereof to define a tip 26. The hooks 20 may be attached to each strut member 34, 44 or select strut members 34, 44. As shown in FIG. 2, the configuration of the filter 30 is such that the hooks 20 attached to the first strut members 34 are oriented toward the hooks 20 attached to the second strut members 44 and vice versa. This orientation facilitates withdrawal of the filter 30 from a blood vessel as it permits retrieval of the filter 30 from either a jugular or femoral approach by using a suitable recovery device, such as, for example, a cone type similar to the device shown and described in U.S. Pat. No. 6,156,055, which is incorporated by reference in its entirety into this application. The translating hook 20 is configured such that the tip 26 is oriented away from the central axis L of the filter 30 in an expanded configuration, but oriented toward the central axis L of the filter 30 in a collapsed configuration, such that depending on the configuration of the filter 30, the tip 26 of the hook 20 can be oriented in different directions, as discussed above.

Filter 30 in one embodiment is cut from a tube of material, such as Nitinol. The particulars of cutting a filter from a tube of material, along with exemplary embodiments of such is shown and described in International Patent Application No. PCT/US2007/06003, filed Mar. 8, 2007, claiming priority to U.S. Provisional Patent Application No. 60/782,019, filed Mar. 14, 2006, each of which is incorporated by reference in its entirety into this application.

Referring now to FIG. 3, a filter 50 includes a set of strut members 52, each of the strut members including a first strut 54 and a second strut 56. The first and second struts 54, 56 are joined at a proximal end to a hub 58, which can include a retrieval member as shown. The strut members 52 can be arranged, such as shown in FIG. 3, to overlap one another such that the outer surface of one strut member 52 is adjacent an inner surface of an adjacent strut member 52. The distal ends of the first and second struts are connected to a translating hook 20, including a first elongate member 22 and a second elongate member 24. The first strut 54 is connected to the distal end of the first elongate member 22 and the second strut 56 is connected to the distal end of the second elongate member 24, the elongate members 22, 24 connected together at a proximal end thereof to define a tip 26. Thus, in this embodiment, the hook 20 connects the first strut 54 to the second strut 56. The elongate members 22, 24 have a curved configuration in the embodiment shown in FIG. 3, together with the struts 54, 56 forming a lobed configuration. The translating hook 20 is configured such that the tip 26 is oriented away from the central axis L of the filter 50 in an expanded configuration, but oriented toward the central axis L of the filter 50 in a collapsed configuration, such that depending on the configuration of the filter 50, the tip 26 of the hook 20 can be oriented in different directions, as discussed above.

The first strut 54 and second strut 56 can include a proximal section 55 and a distal section 57 that are angled with respect to one another such that an angle B is formed therebetween. Proximal section 55 extends from the hub 58, while distal section 57 is connected to the hook 20. Angle B can be different for the first and second struts 54, 56, or angle B can be the same for the first and second struts 54, 56 in one strut member 52, but different for the first and second struts 54, 56 in an adjacent strut member. The angle B between the proximal section 55 and distal section 57 is in the range of approximately 95 degrees to approximately 170 degrees, preferably in the range of approximately 120 degrees to approximately 150 degrees.

FIG. 4 illustrates a filter 60, including four appendages 62 connected proximally to a hub 68. Although not shown in FIG. 4, the hub 68 can include a retrieval member. Also, although four appendages 62 are shown in this embodiment, the filter 60 could instead have two, three, five, six, etc. appendages. The appendages 62 include a first leg 61 and a second leg 63, each of which have a proximal end joined at the hub 68, and extend radially outward from a central axis L when the filter 60 is in an expanded configuration (as shown). Connected to the distal ends of each of the legs 61, 63 is a strut member 64, including a first strut 65 and a second strut 67. The proximal end of the first strut 65 is connected via a connecting portion 69 to the first leg 61, while the proximal end of the second strut 67 is connected via a connecting portion 69 to the second leg 63. The distal ends of the first strut 65 and the second strut 67 are also connected together via a connecting portion 69. The connecting portions 69 can be separate members attached to the legs and struts and can be of different shapes and sizes; however, in the preferred embodiment, the legs, struts and connecting portions are one continuous member, created through processes known to one skilled in the art (e.g., molding, laser cutting of a tube or a sheet, etc.). Thus, each appendage 62 includes three connecting portions 69, which as shown in FIG. 4, are adjacent the outer perimeter of the filter 60 in the expanded configuration.

Disposed adjacent each of the connecting portions 69 are translating hooks 20, including elongate members 22, 24 connected together at a proximal end thereof to define a tip 26. The distal ends of the elongate members 22, 24 are attached respectively to first and second struts 65, 67, to first leg 61 and first strut 65 and to second leg 63 and second strut 67 as shown. In other embodiments, translating hooks 20 are disposed only between first and second struts 65, 67 of each appendage 62, or select appendages 62. In still other embodiments, translating hooks 20 are disposed only between legs and struts of each appendage 62 or select appendages. The translating hooks 20 are configured such that the tips 26 are oriented away from the central axis L of the filter 60 in an expanded configuration, but are oriented toward the central axis L of the filter 60 in a collapsed configuration, such that depending on the configuration of the filter 60, the tips 26 of the hooks 20 can be oriented in different directions, as discussed above. In addition to the translating hooks 20, one or more vessel engaging members may be positioned along the length of the appendages 62.

FIG. 5 illustrates a filter 70, including a first hub 78 and a second hub 88. Although not shown, in some embodiments, one or both of the hubs 78, 88 may include a retrieval member. Extending from the first hub 78 is a first set of legs 72 connected to a first set of strut members 73, the strut members 73 including a first strut 74 and a second strut 76 that each have an end connected to an end of adjacent legs 72 (i.e., the end of the first strut 74 of a strut member 73 is connected to an end of one leg 72 and the end of the second strut 76 of a strut member 73 is connected to an end of an adjacent leg 72). The end of a first strut 74 of one strut member 73 is connected to the same leg 72 as that of a second strut 76 of an adjacent strut member 73, as shown, such that a plurality of connected cells are formed. The opposite ends of the first and second struts 74, 76 of a strut member 73 are connected together to form the shape of a spade when the filter 70 is in an expanded configuration (as shown) with an end 75 that is connected to a connecting member 80. Disposed adjacent the tips 75 are translating hooks 20, including elongate members 22, 24 connected together at a proximal end thereof to define a tip 26. The translating hooks 20 are configured such that the tips 26 are oriented away from the central axis L of the filter 70 in an expanded configuration (as shown), but are oriented toward the central axis L of the filter 70 in a collapsed configuration, such that depending on the configuration of the filter 70, the tips 26 of the hooks 20 can be oriented in different directions, as discussed above.

Extending from the second hub 88 is a second set of legs 82 connected to a second set of strut members 83, the strut members 83 including a first strut 84 and a second strut 86 that each have an end connected to an end of adjacent legs 82 (i.e., the end of the first strut 84 of a strut member 83 is connected to an end of one leg 82 and the end of the second strut 86 of a strut member 83 is connected to an end of an adjacent leg 82). The end of a first strut 84 of one strut member 83 is connected to the same leg 82 as that of a second strut 86 of an adjacent strut member 83, as shown, such that a plurality of connected cells are formed. The opposite ends of the first and second struts 84, 86 of a strut member 83 are connected together to form the shape of a spade when the filter 70 is in an expanded configuration (as shown) with an end 85 that is connected to a connecting member 80. Disposed adjacent the tips 85 are translating hooks 20, including elongate members 22, 24 connected together at a proximal end thereof to define a tip 26, the tips 26 of the hooks 20 configured to be oriented in different directions depending on the configuration of the filter 70, as discussed above. The connecting members 80 connect the tips 75 to the tips 85 and are lie generally parallel to the longitudinal axis in both the expanded and collapsed configurations of filter 70. Details of the filters shown in FIGS. 4 and 5 are further shown and described in U.S. Pat. Nos. 6,517,573 and 6,443,972, each of which is incorporated by reference in its entirety into this application.

One particular advantage recognized by applicants of incorporating one or more translating hooks into a filter is that during delivery of the filter to a blood vessel or other bodily cavity, the tips of the hooks are oriented toward the central axis of the filter such that the risk of engaging the hooks with the introducer catheter is greatly minimized. More particularly, because the tips of the hooks are retracted completely away from a sheath or delivery catheter used to introduce the filter into a body lumen, any relative movement of the sheath and the filter will not result in undesirable events, such as tearing of the sheath or catching of the filter on the sheath, which could potentially lead to misalignment of the filter in the vessel, release of sheath material into the body, or other potentially dangerous outcomes. In one particular embodiment, the filter is collapsed for inserting in a delivery catheter having an inside surface defining an inside diameter (ID) of less than 9 French, such that the translating hooks are spaced apart from the inside surface of the catheter. In the same way, recovery of a filter with translating hooks avoids the aforementioned undesirable events; when the filter is compressed to a collapsed configuration from an expanded deployed configuration of the filter in a vessel, the translating hooks bend toward the central axis of the filter for safe retraction from the vessel.

The use of a shape memory material, such as Nitinol, for the arms, legs, or hooks facilitates collapsing the filter radially inward from its normally expanded (i.e., unconstrained) configuration toward its longitudinal axis into a collapsed configuration for insertion into a body vessel. The properties of Nitinol allow the filter members to withstand enormous deformations (e.g., eight times as much as stainless steel) without having any effect of the filter ability to recover to the pre-determined shape. This is due to the crystal phase transitions between rigid austenite and softer martensite, which phenomenon enables the implant to be loaded into a very small diameter sheath for delivery, significantly reducing the potential trauma and complications to the insertion site. Transition between the martensitic and austenitic forms of the shape memory material can be achieved by increasing or decreasing the material deformation above and below the transition stress level while the material remains above the transition temperature range, specifically Af. This is particularly important in the case of the hooks, as they may be deformed significantly (hence, becoming martensitic) while the filter is challenged by clots. The super-elastic properties will allow the hooks to re-assume their intended shape as soon as the load is released (e.g. the clot breaks down).

The hooks may be retrieved from the Inferior Vena Cava ("IVC") wall during the filter removal when longitudinal force is applied to the hub in the direction of the blood flow. Under this concentrated stress, the hooks will deform and transition to the martensitic state, thereby becoming super-elastic. Thus, the hooks are designed to bend when a specific retrieval force is applied and spring back to their original shape once the retrieval force is removed. Alternatively, a reduction in temperature below the Af temperature can be applied to the shape memory material to cause a change in the crystalline phase of the material, thereby rendering the material malleable during loading or retrieval of the filter. Various techniques can be used to cause a change in crystalline phase such as, for example, cold saline, low temperature fluid or thermal conductor.

By virtue of the characteristics of thermal shape memory material, the filter members can be cooled below the martensitic-to-austenitic transition temperature, and then straightened and held in a collapsed, straight form that can pass through a length of fine plastic tubing with an internal diameter of approximately 2 millimeters (mm), e.g., a #8 French catheter. In its high temperature form (as in a mammalian body), the filter recovers to a preformed filtering shape. Alternatively, the legs or arms may be made of wires of spring metal which can be straightened and compressed within a catheter or tube and will diverge into a deployed shape when the tube is removed.

The deployed shapes and configurations of the filter members can be set (imprinted with a memory shape) by annealing the members at high temperature (e.g. 500° C.) while holding them in the desired shape. Thereafter, whenever the filter is in the austenitic form (i.e., at a temperature above the martensitic-to-austenitic transition temperature or Af temperature), the members return to the memory shape. Example methods for setting the high-temperature shape of filters are disclosed in U.S. Pat. No. 4,425,908, which is incorporated by reference in its entirety into this application.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A filter with an assembly comprising:
    a hub;
    and
    hollow, kite-shaped arms comprising:
        a three- or four-sided inner leaf comprising two wire-arm segments with first segment ends connected to the hub;
        a triangular outer leaf comprising two wire-arm segments with first segment ends connected together forming an outer leaf vertex with a tip;
        wherein the second, inner-leaf segment ends connect to the second, outer-leaf segment ends to form two joining vertices between the leaves with the bases of the leaves formed from a line connecting the joined vertices, but not containing a wire;
        and
        a hook having two members wherein the members connect at first ends into a tip,
        and
        connect at second ends to the wire segments adjacent a joining vertex or an outer leaf vertex and near to and bridging the vertex
        and
    wherein
        the filter has two states a retracted state having a first diameter and length and an expanded state having a second diameter larger than the first diameter
        and
        hook bias causes the hook tip to point inward in the retracted state and causes the hook tip to rotate outward in the expanded state.

2. The filter of claim 1 wherein hooks bridge each of the joining vertices.

3. The filter of claim 1 having two or more arms.

4. The filter of claim 3 wherein hooks bridge each of the outer leaf vertices.

5. The filter of claim 4 wherein inner-leaf wire-arm segments of adjacent inner leaves are fused into a single wire-arm.

6. The filter of claim 5 having an even number of arms wherein hooks bridge alternate outer-leaf vertices forming bridged tips on the bridged outer-leaf vertices and unbridged tips on the outer leaves without bridged tips.

7. The filter of claim 6 comprising a second assembly inverted from the first assembly such that the hubs lay opposite each other wherein the unbridged tips of the outer leaves on the first assembly connect to the unbridged tips of the outer leaves on the second assembly by wire segments.

8. The filter of claim 5 wherein the length of inner-leaf wire segments is greater that the length of outer-leaf wire segments.

9. The filter of claim 8 having an even number of arms wherein hooks bridge alternate outer-leaf vertices forming bridged tips on the bridged outer-leaf vertices and unbridged tips on the outer leaves without bridged tips.

10. The filter of claim 9 comprising a second assembly inverted from the first assembly such that the hubs lay opposite each other wherein the unbridged tips of the outer leaves on the first assembly connect to the unbridged tips of the outer leaves on the second assembly by wire segments.

11. The filter of claim 8 wherein the hub further comprises a central axis and the tip of the outer leaf points toward the central axis.

12. The filter of claim 1 wherein the hub further comprises a central axis and the tip of the outer leaf points toward the central axis.

13. A method comprising:
    anchoring the filter of claim 7 by introducing the filter in the retracted state into a blood vessel lumen;
    and
    expanding the filter to the expanded state rotating a hook tip outward into the blood vessel wall.

14. The method of claim 13 further comprising retrieving the filter by compressing the filter back into the retracted state to rotate the hook tip inward out of the wall.

15. The method of claim 14 wherein compressing comprises moving the filter into a recovery catheter.

16. The method of claim 15 wherein introducing comprises supplying the filter inside of a delivery catheter having a less-than-9-French inside diameter.

17. A method comprising:
    anchoring the filter of claim 1 by introducing the filter in the retracted state into a blood vessel lumen;
    and
    expanding the filter to the expanded state rotating a hook tip outward into the blood vessel wall.

18. The method of claim 17 further comprising retrieving the filter by compressing the filter back into the retracted state to rotate the hook tip inward out of the wall.

19. The method of claim 18 wherein compressing comprises moving the filter into a recovery catheter.

20. The method of claim 19 wherein introducing comprises supplying the filter inside of a delivery catheter having a less-than-9-French inside diameter.

* * * * *